United States Patent
Helgason et al.

(10) Patent No.: US 11,591,471 B2
(45) Date of Patent: Feb. 28, 2023

(54) ENGINEERED SKIN EQUIVALENT, METHOD OF MANUFACTURE THEREOF AND PRODUCTS DERIVED THEREFROM

(71) Applicants: VitroLabs Inc, South San Francisco, CA (US); King's College London, London (GB)

(72) Inventors: Ingvar Helgason, South San Francisco, CA (US); Dusko Ilic, London (GB)

(73) Assignees: VitroLabs Inc, Milpitas, CA (US); King's College London, London (GB)

( * ) Notice: Subject to any disclaimer, the term of this patent is extended or adjusted under 35 U.S.C. 154(b) by 0 days.

(21) Appl. No.: 17/751,440

(22) Filed: May 23, 2022

(65) Prior Publication Data
US 2022/0403172 A1 Dec. 22, 2022

Related U.S. Application Data

(63) Continuation of application No. 17/366,550, filed on Jul. 2, 2021, now Pat. No. 11,377,559, which is a
(Continued)

(51) Int. Cl.
*C08L 89/00* (2006.01)
*C08L 89/06* (2006.01)
(Continued)

(52) U.S. Cl.
CPC ............ *C08L 89/06* (2013.01); *C12N 5/0625* (2013.01); *C12N 5/0629* (2013.01);
(Continued)

(58) Field of Classification Search
CPC ..... C08L 89/06; C12N 5/0625; C12N 5/0629; C12N 5/0698; C12N 11/02; C12N 2501/155; C12N 2501/385; C12N 2502/091; C12N 2502/094; C12N 2502/13; C12N 2506/45; C12N 2533/30; C12N 2533/54; C14C 3/02; C14C 13/00
(Continued)

(56) References Cited

U.S. PATENT DOCUMENTS

| 4,485,096 A | 11/1984 | Bell |
| 6,497,875 B1 | 12/2002 | Sorrell et al. |

(Continued)

FOREIGN PATENT DOCUMENTS

| CN | 1468634 A | 1/2004 |
| CN | 1528253 A | 9/2004 |

(Continued)

OTHER PUBLICATIONS

Baxter. Welcome to the TISSEEL [Fibrin Sealant] Sealing Stops Bleeding. © 2017 Baxter Healthcare Corporation. 1 page. URL: <http://www.tisseel.com/us/index.html>.

(Continued)

*Primary Examiner* — Eisa B Elhilo
(74) *Attorney, Agent, or Firm* — Wilson Sonsini Goodrich & Rosati

(57) ABSTRACT

Disclosed herein are synthetic leathers, artificial epidermal layers, artificial dermal layers, layered structures, products produced therefrom and methods of producing the same.

20 Claims, 13 Drawing Sheets

Related U.S. Application Data continuation of application No. 16/892,839, filed on Jun. 4, 2020, now Pat. No. 11,091,639, which is a continuation of application No. 16/299,734, filed on Mar. 12, 2019, now Pat. No. 10,711,136, which is a continuation of application No. 15/493,083, filed on Apr. 20, 2017, now Pat. No. 10,273,549.

(60) Provisional application No. 62/325,819, filed on Apr. 21, 2016.

(51) Int. Cl.
  C12N 5/071   (2010.01)
  C12N 11/02   (2006.01)
  C14C 3/02    (2006.01)
  C14C 13/00   (2006.01)

(52) U.S. Cl.
  CPC ............ C12N 5/0698 (2013.01); C12N 11/02 (2013.01); C14C 3/02 (2013.01); C14C 13/00 (2013.01); *C12N 2501/155* (2013.01); *C12N 2501/385* (2013.01); *C12N 2502/091* (2013.01); *C12N 2502/094* (2013.01); *C12N 2502/13* (2013.01); *C12N 2506/45* (2013.01); *C12N 2533/30* (2013.01); *C12N 2533/54* (2013.01)

(58) Field of Classification Search
  USPC ...................................... 424/93.7; 8/94.19 R
  See application file for complete search history.

(56) References Cited

U.S. PATENT DOCUMENTS

| | | | |
|---|---|---|---|
| 9,428,817 | B2 | 8/2016 | Greene et al. |
| 10,066,209 | B2 | 9/2018 | Phan |
| 10,273,549 | B2 | 4/2019 | Helgason et al. |
| 2001/0048917 | A1 | 12/2001 | Hoeffler et al. |
| 2006/0105454 | A1 | 5/2006 | Son et al. |
| 2007/0116676 | A1* | 5/2007 | Kida ............... C12N 5/00 435/372 |
| 2007/0148138 | A1 | 6/2007 | Barrows et al. |
| 2008/0095748 | A1* | 4/2008 | Kharazi ............ C12N 5/0698 424/443 |
| 2009/0162896 | A1 | 6/2009 | Scheibel |
| 2010/0062041 | A1 | 3/2010 | Dai et al. |
| 2010/0255059 | A1 | 10/2010 | Marquez et al. |
| 2011/0052693 | A1 | 3/2011 | Kao et al. |
| 2011/0165130 | A1 | 7/2011 | Guenou |
| 2012/0214236 | A1 | 8/2012 | Bhatia et al. |
| 2013/0025003 | A1 | 1/2013 | Trieu et al. |
| 2013/0177648 | A1* | 7/2013 | O'Brien ............ A61K 47/42 424/484 |
| 2013/0255003 | A1* | 10/2013 | Forgacs ............ C12N 5/0698 8/94.2 |
| 2014/0178346 | A1 | 6/2014 | Byrne et al. |
| 2015/0250925 | A1* | 9/2015 | Akashi ............. A61L 27/3633 435/373 |
| 2016/0097109 | A1* | 4/2016 | Forgacs ............ C14C 13/00 435/70.3 |
| 2016/0097154 | A1 | 4/2016 | Dumbrique et al. |
| 2016/0102289 | A1 | 4/2016 | Yu et al. |
| 2016/0348078 | A1* | 12/2016 | Forgacs ............ C12N 5/0698 |
| 2016/0354447 | A1 | 12/2016 | Schmuck et al. |
| 2019/0201579 | A1 | 7/2019 | Tsuji et al. |

FOREIGN PATENT DOCUMENTS

| | | | | |
|---|---|---|---|---|
| CN | 101264344 | A | 9/2008 | |
| CN | 101330935 | A | 12/2008 | |
| CN | 101538555 | A | 9/2009 | |
| CN | 101792735 | A | 8/2010 | |
| CN | 101802172 | A | 8/2010 | |
| CN | 103893831 | A | 7/2014 | |
| CN | 101385871 | B | 1/2015 | |
| EP | 1334714 | A1 | 8/2003 | |
| EP | 1589098 | A1 | 10/2005 | |
| EP | 2103687 | A1 | 9/2009 | |
| EP | 2297299 | A1 | 3/2011 | |
| EP | 3473705 | A1 | 4/2019 | |
| EP | 3690029 | A1 * | 5/2020 | ............... C12N 5/00 |
| EP | 4067478 | A1 * | 10/2022 | ............... C12N 5/00 |
| JP | 2010100750 | A | 5/2010 | |
| JP | 2016016267 | A | 2/2016 | |
| JP | 6218238 | B2 | 10/2017 | |
| KR | 100648405 | B1 | 11/2006 | |
| RU | 2342164 | C2 | 12/2008 | |
| RU | 2568059 | C1 | 11/2015 | |
| WO | WO-9945770 | A1 | 9/1999 | |
| WO | WO-2009156398 | A1 | 12/2009 | |
| WO | WO-2014201406 | A1 | 12/2014 | |
| WO | WO 2014201406 | A1 * | 12/2014 | ............... C14C 5/00 |
| WO | 2016073453 | A1 * | 5/2016 | ............ C14C 13/00 |
| WO | WO-2017184967 | A1 | 10/2017 | |

OTHER PUBLICATIONS

Bellas, et al. In vitro 3D full-thickness skin-equivalent tissue model using silk and collagen biomaterials. Macromol Biosci. Dec. 2012;12(12):1627-36. doi: 10.1002/mabi.201200262. Epub Nov. 19, 2012.

Bilousova, et al. Differentiation of mouse induced pluripotent stem cells into a multipotent keratinocyte lineage. J Invest Dermatol. Apr. 2011;131(4):857-64.

British Search and Examination Report dated Oct. 13, 2021 for United Kingdom Application Serial No. GB1706380.1.

Buchholz, et al. Derivation of functional retinal pigmented epithelium from induced pluripotent stem cells. Stem Cells. Oct. 2009;27(10):2427-34.

Burke, et al. Successful use of a physiologically acceptable artificial skin in the treatment of extensive burn injury. Ann Surg. Oct. 1981; 194(4): 413-428.

Bye, et al. Development of a Basement Membrane Substitute Incorporated Into an Electrospun Scaffold for 3D Skin Tissue Engineering. Journal of Biomaterials and Tissue Engineering, vol. 4, No. 9, Sep. 2014, pp. 686-692(7).

Carlson, et al. Three-dimensional tissue models of normal and diseased skin. Curr Protoc Cell Biol. Dec. 2008;Chapter 19:Unit 19.9. doi: 10.1002/0471143030.cb1909s41.

CELLnTEC. Full Thickness Skin Models. CELLnTEC: Advanced Cell Systems. www.cellntec.com. Accessed Apr. 22, 2016. 3 pages.

CELLnTEC. Proliferation/Differentiation. CELLnTEC: Advanced Cell Systems. Accessed Apr. 22, 2016. 3 pages. URL: <http://cellntec.com/products/resources/protocols/culture/>.

Chen, et al., "Differetiation of Mouse Induced Pluripotent Stem Cells into a Multipotent Keratinocyte Lineage" Journal of Investigative Dermatology, 131(4), 857-864.

Chen Y., et al. "Highly Rapid and Efficient Conversion of Human Fibroblasts to Keratinocyte-Like Cells", Journal of Investigative Dermatology. 2014; 134(2):335-344; abstract.

De Breij, et al. Three-dimensional human skin equivalent as a tool to study Acinetobacter baumannii colonization. Antimicrob Agents Chemother. May 2012;56(5):2459-64. doi: 10.1128/AAC.05975-11. Epub Jan. 30, 2012.

Gledhill, et al. Melanin Transfer in Human 3D Skin Equivalents Generated Exclusively from Induced Pluripotent Stem Cells. Pios One. Published: Aug. 26, 2015. https://doi.org/10.1371/journal.pone.0136713.

Hansbrough, et al. Evaluation of Graftskin Composite Grafts on Full-Thickness Wounds on Athymic Mice. J. Burn Care Rehabil., 15:346-53 (1994).

International Search Report and Written Opinion dated Sep. 22, 2017 for International PCT Patent Application No. PCT/US2017/028819.

Itoh, et al. Generation of 3D skin equivalents fully reconstituted from human induced pluripotent stem cells (iPSCs). PLoS One. Oct. 11, 2013;8(10):e77673. doi: 10.1371/journal.pone.0077673. eCollection 2013.

(56) References Cited

OTHER PUBLICATIONS

Kellouche S., et al., Tissue engineering for full-thickness burns: a dermal substitute from bench to bedside. Biochem Biophys Res Commun. Nov. 23, 2007;363(3):472-8.

Kogut, et al. Differentiation of human induced pluripotent stem cells into a keratinocyte lineage. Methods Mol Biol. 2014;1195:1-12. doi: 10.1007/7651_2013_64.

Krugluger, et al. Reorganization of hair follicles in human skin organ culture induced by cultured human follicle-derived cells. Exp Dermatol. Aug. 2005;14(8):580-5.

Petrova, et al. 3D In vitro model of a functional epidermal permeability barrier from human embryonic stem cells and induced pluripotent stem cells. Stem Cell Reports. Apr. 24, 2014;2(5):675-89. doi: 10.1016/j.stemcr.2014.03.009. eCollection May 6, 2014.

Quan T. et al. Enhancing structural support of the dermal microenvironment activates fibroblasts, endothelial cells, and keratinocytes in aged human skin in vivo. J Invest Dermatol. Mar. 2013;133(3):658-667. doi: 10.1038/jid.2012.364.

Randall, et al. A comparison of the culture and growth of dermal papilla cells from hair follicles from non-balding and balding (androgenetic alopecia) scalp. Br J Dermatol 1996: 134: 437-444.

SearchReport dated Aug. 17, 2020 for Application No. 2018140838 (3 pages).

Sekar et al., "A novel cross-linked human amniotic membrane for corneal implantations", Nov. 15, 2012, Institution of Mechanical Engineers—Journal of Engineering Medicine, vol. 3, Issue 227, pp. 221-228 (Year:2012).

Shamis Y., et al. "Fibroblasts Derived from Human Pluripotent Stem Cells Activate Angiogenic Responses In Vitro and In Vivo", PLoS ONE.2013; 8(12): e83755; DOI: 10.1371/journal.pone.0083755; abstract.

Souto, et al. Model for Human Skin Reconstructed in Vitro Composed of Associated Dermis and Epidermis. Sao Paulo Med J 124 (2), 71-76. Mar. 2, 2006.

Stratatech. Core Technology. © 2017 Stratatech a Mallinckrodt Company. 2 pages. URL: <http://www.stratatechcorp.com/science/index.php>.

Sun, et al. Lowered Humidity Produces Human Epidermal Equivalents with Enhanced Barrier Properties. Tissue Eng Part C Methods. Jan. 1, 2015; 21(1): 15-22. Published online Jun. 16, 2014. doi: 10.1089/ten.tec.2014.0065.

Supplementary Partial European Search Report dated Nov. 6, 2019 for Application Serial No. EP 17 78 6708, (11 pages).

Takahashi et al. Induction of pluripotent stem cells from adult human fibroblasts by defined factors. Cell 131(5):861-72 (2007).

U.S. Appl. No. 16/095,308 Final Office Action dated Oct. 30, 2020.

U.S. Appl. No. 16/095,308 Non-Final Office Action dated Aug. 8, 2019.

Varani J. Preservation of human skin structure and function in organ culture. Histol Histopathol. Jul. 1998;13(3):775-83. doi: 10.14670/HH-13.775. Abstract.

Verkhovskaya L.Z et al., The effect of glycerol alkoxy-derivatives on morphological and functional properties of continuous cell culture, Cryobiology, 1990.

Wang Y., et al. "Biomimetic fibroblast-loaded artificial dermis with "sandwich" structure and designed gradient pore sizes promotes wound healing by favoring granulation tissue formation and wound re-epithelialization", Acta Biomaterialia. (Jan. 15, 2016); 30:246-257; DOI: 10.1016/j.actbio.2015.11.035; abstract, pp. 246-254.

Xie L., et al. "CD10 expressed by fibroblasts and melanoma cells degrades endothelin-1 secreted by human keratinocytes", Eur JDermatol. 2011;21(4):505-509; DOI: 10.1684/ejd.2011.1371; abstract.

Yang, et al. Generation of folliculogenic human epithelial stem cells from induced pluripotent stem cells. Nat Commun. 2014; 5: 3071. Author manuscript; available in PMC Jul. 1, 2014.

Yu, et al. Induced pluripotent stem cell lines derived from human somatic cells. Science. Dec. 21, 2007;318(5858):1917-20. Epub Nov. 20, 2007.

\* cited by examiner

| |
|---|
| 1. Grow dermal layer and epidermal layer separately |
| 2. Place stratified and quality control-verified epidermal layer atop of dermal layer (14+1 days) |
| 3. Add natural and synthetic supplements to induce ECM production and assembly (e.g. dextran sulphate, carrageenan) |

FIG. 3

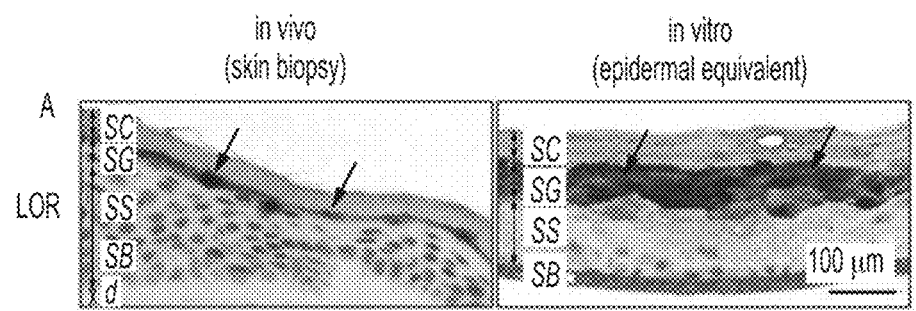
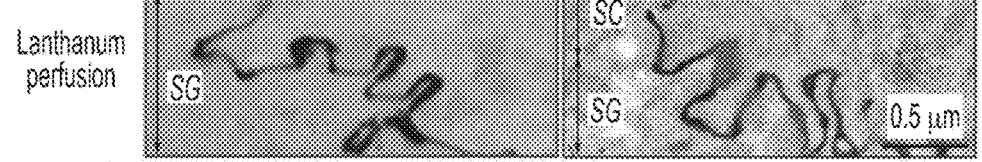
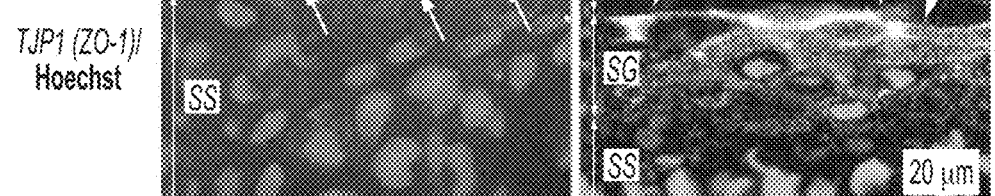
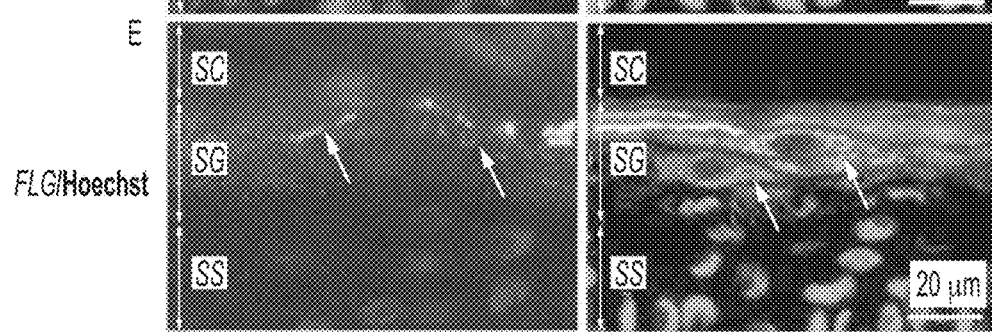
FIG. 6A
FIG. 6B
FIG. 6C
FIG. 6D
FIG. 6E

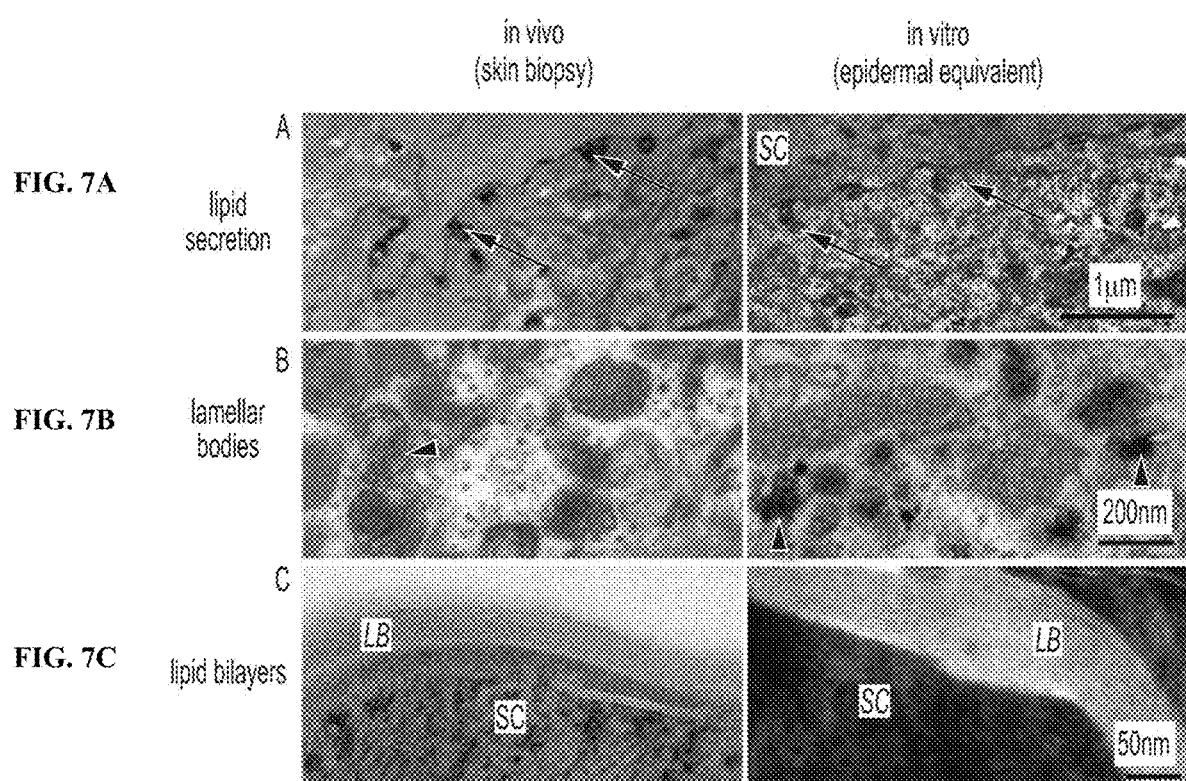

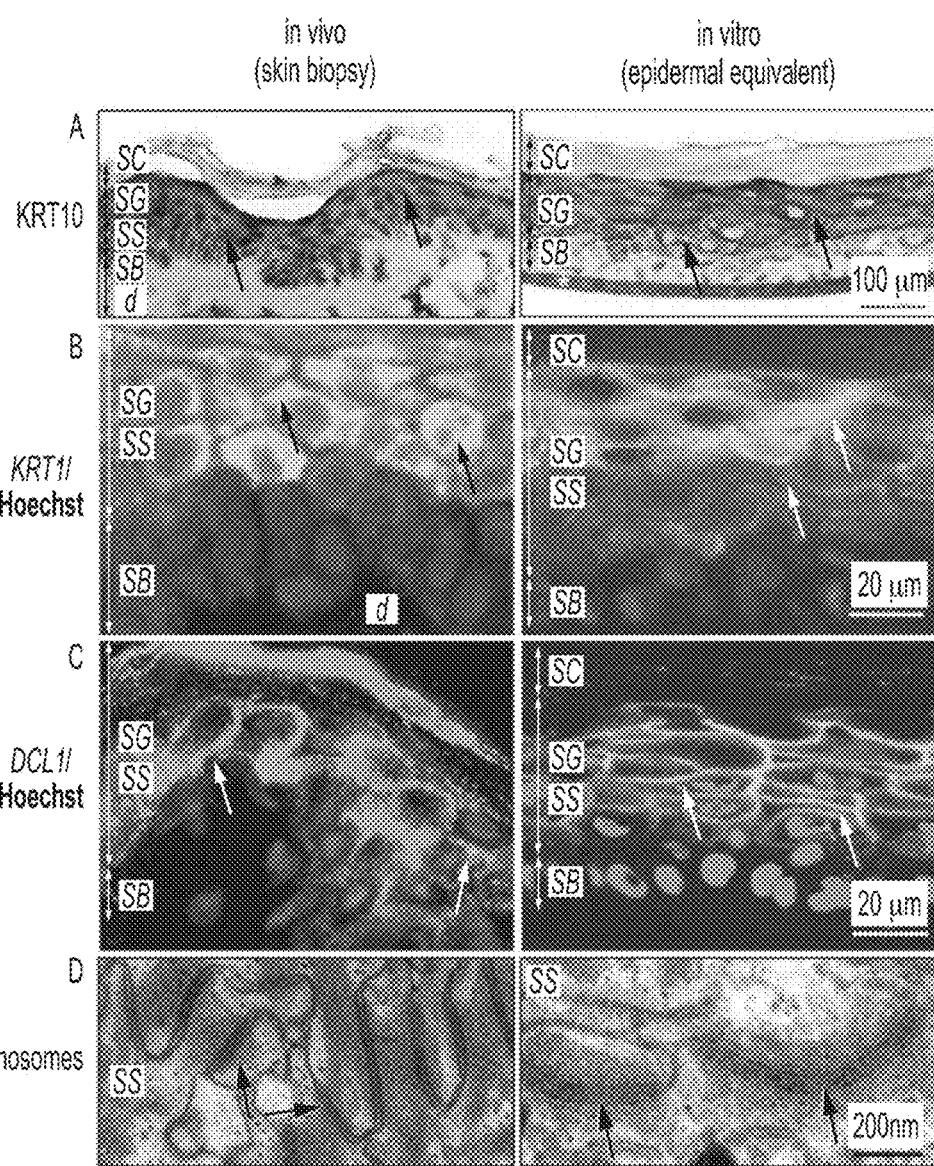

Day 2

ENGINEERED SKIN EQUIVALENT, METHOD OF MANUFACTURE THEREOF AND PRODUCTS DERIVED THEREFROM

CROSS REFERENCE

This application is a continuation of U.S. application Ser. No. 17/366,550, filed Jul. 2, 2021, which is a continuation of U.S. application Ser. No. 16/892,839, now U.S. Pat. No. 11,091,639, filed Jun. 4, 2020, which is a continuation of U.S. application Ser. No. 16/299,734, now U.S. Pat. No. 10,711,136, filed Mar. 12, 2019, which is a continuation of U.S. application Ser. No. 15/493,083, filed Apr. 20, 2017, now U.S. Pat. No. 10,273,549, issued Apr. 30, 2019 which claims priority to U.S. Provisional Application No. 62/325,819, filed on Apr. 21, 2016, each of which are incorporated herein by reference in their entirety.

GOVERNMENT SUPPORT

This invention was made with the support of National Institutes of Health (NIH) Grant Number R21 AR061583 and RO1 AR051930, Medical Research Council (UK) Grant Number G0801061, Research Service of the Department of Veterans Affairs and Dystrophic Epidermolysis Bullosa Research Association.

SUMMARY OF THE DISCLOSURE

Disclosed herein are methods of making a synthetic leather. In some embodiments, the method can comprise forming an artificial dermal layer comprising a fibroblast. In some embodiments, the method can comprise tanning at least a portion of a dermal layer, thereby forming a synthetic leather. In some embodiments, a fibroblast can be differentiated from an induced pluripotent stem cell. In some embodiments, the method can further comprise forming an artificial epidermal layer. In some embodiments, an epidermal layer can comprise a keratinocyte. In some embodiments, the method can comprise placing an epidermal layer upon a dermal layer thereby forming a layered structure. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can comprise a pigment. In some embodiments, a melanocyte can be a mammalian melanocyte. In some embodiments, a mammal can be a human. In some embodiments, a fibroblast can express CD10, CD73, CD44, CD90, type I collagen, type III collagen, prolyl-4-hydroxylase beta, or a combination thereof. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer can further comprise collagen. In some embodiments, an epidermal layer can be subjected to further processing. In some embodiments, a layered structure can further comprise collagen. In some embodiments, a layered structure can be subjected to further processing. In some embodiments, a dermal layer can further comprise collagen. In some embodiments, a dermal layer can be subjected to further processing. In some embodiments, processing can be selected from a group consisting of preserving, soaking, bating, pickling, depickling, thinning, retanning, lubricating, crusting, wetting, sammying, shaving, rechroming, neutralizing, dyeing, fatliquoring, filling, stripping, stuffing, whitening, fixating, setting, drying, conditioning, milling, staking, buffing, finishing, oiling, brushing, padding, impregnating, spraying, roller coating, curtain coating, polishing, plating, embossing, ironing, glazing, tumbling and any combination thereof. In some embodiments, collagen can be produced at least in part by a collagen producing cell, can be separately added, or any combination thereof. In some embodiments, a collagen producing cell can comprise an epithelial cell, a keratinocyte, a fibroblast, a corneocyte, a melanocyte, a Langerhans cell, a basal cell, or a combination thereof. In some embodiments, a collagen producing cell can comprise a epithelial cell wherein the epithelial cell can comprise a squamous cell, a cuboidal cell, a columnar cell, a basal cell, or a combination thereof. In some embodiments, a collagen producing cell can comprise a keratinocyte wherein the keratinocyte can comprise an epithelial keratinocyte, basal keratinocyte, proliferating basal keratinocyte, differentiated suprabasal keratinocyte, or a combination thereof. In some embodiments, a collagen producing cell can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be placed upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can further comprise a basement membrane substitute. In some embodiments, a basement membrane substitute can be between an epidermal layer and a dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a synthetic leather. In some embodiments, a dermal layer or an epidermal layer can be cultured in vitro. In some embodiments, a dermal layer can be cultured in vitro. In some embodiments, a dermal layer can be cultured with a supplement. In some embodiments, a supplement can comprise one or more of collagen, fibrin, growth factors, ascorbic acid, dextran sulphate, or carrageenan. In some embodiments, a supplement can be a natural supplement. In some embodiments, a supplement can be a synthetic supplement. In some embodiments, an induced pluripotent stem cell can be produced through the induced gene expression of Oct3, Oct4, Sox2, Klf4, c-Myc or a combination thereof in an adult somatic cell. In some embodiments, at least a portion of a leather article can be formed from the methods disclosed herein. In some embodiments, a leather article can comprise one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a leather article can be a watch strap. In some embodiments, a leather article can be a belt. In some embodiments, a leather article can be a bag. At least about 2% of cells comprised in a synthetic leather can be differentiated from an induced pluripotent stem cell. At least about 10% of cells comprised in synthetic leather can be differentiated from an induced pluripotent stem cell. At least about 50% of cells comprised in a synthetic leather can be differentiated from an induced pluripotent stem cell.

Disclosed herein are methods of making a synthetic leather. In some embodiments, the method can comprise placing an artificial epidermal layer upon an artificial dermal layer thereby forming a layered structure. In some embodiments, an epidermal layer can comprise a keratinocyte and a dermal layer can comprise a fibroblast. In some embodiments, the method can comprise tanning at least a portion of a layered structure, thereby forming a synthetic leather. In some embodiments, a fibroblast or a keratinocyte can be differentiated from an induced pluripotent stem cell. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can comprise a pigment. In some embodiments, a melanocyte can be a mammalian melanocyte. In some embodiments, a mammal can be a human. In some embodiments, a fibroblast can be differentiated from an induced pluripotent stem cell. In some embodiments, a fibroblast can express CD10, CD73, CD44, CD90, type I collagen, type III collagen, prolyl-4-hydroxylase beta, or a combination thereof. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer can further comprise collagen. In some embodiments, an epidermal layer can be subjected to further processing. In some embodiments, a layered structure can further comprise collagen. In some embodiments, a layered structure can be subjected to further processing. In some embodiments, a dermal layer can further comprise collagen. In some embodiments, a dermal layer can be subjected to further processing. In some embodiments, processing can be selected from a group consisting of preserving, soaking, bating, pickling, depickling, thinning, retanning, lubricating, crusting, wetting,sammying, shaving, rechroming, neutralizing, dyeing, fatliquoring, filling, stripping, stuffing, whitening, fixating, setting, drying, conditioning, milling, staking, buffing, finishing, oiling, brushing, padding, impregnating, spraying, roller coating, curtain coating, polishing, plating, embossing, ironing, glazing, tumbling and any combination thereof. In some embodiments, collagen can be produced at least in part by a collagen producing cell, can be separately added, or any combination thereof. In some embodiments, a collagen producing cell can comprise an epithelial cell, a keratinocyte, a fibroblast, a corneocyte, a melanocyte, a Langerhans cell, a basal cell, or a combination thereof. In some embodiments, a collagen producing cell can comprise a epithelial cell wherein the epithelial cell can comprise a squamous cell, a cuboidal cell, a columnar cell, a basal cell, or a combination thereof. In some embodiments, a collagen producing cell can comprise a keratinocyte wherein the keratinocyte can comprise an epithelial keratinocyte, basal keratinocyte, proliferating basal keratinocyte, differentiated suprabasal keratinocyte, or a combination thereof. In some embodiments, a collagen producing cell can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be placed upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can further comprise a basement membrane substitute. In some embodiments, a basement membrane substitute can be between an epidermal layer and a dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a synthetic leather. In some embodiments, a dermal layer or an epidermal layer can be cultured in vitro. In some embodiments, a dermal layer can be cultured in vitro. In some embodiments, a dermal layer can be cultured with a supplement. In some embodiments, a supplement can comprise one or more of collagen, fibrin, growth factors, ascorbic acid, dextran sulphate, or carrageenan. In some embodiments, a supplement can be a natural supplement. In some embodiments, a supplement can be a synthetic supplement. In some embodiments, an induced pluripotent stem cell can be produced through the induced gene expression of Oct3, Oct4, Sox2, Klf4, c-Myc or a combination thereof in an adult somatic cell. In some embodiments, at least a portion of a leather article can be formed from the methods disclosed herein. In some embodiments, a leather article can comprise one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a leather article can be a watch strap. In some embodiments, a leather article can be a belt. In some embodiments, a leather article can be a bag. At least about 2% of cells comprised in a synthetic leather can be differentiated from an induced pluripotent stem cell. At least about 10% of cells comprised in synthetic leather can be differentiated from an induced pluripotent stem cell. At least about 50% of cells comprised in a synthetic leather can be differentiated from an induced pluripotent stem cell.

Disclosed herein are methods of making a synthetic leather. In some embodiments, the method can comprise placing an artificial epidermal layer upon an artificial dermal layer thereby forming a layered structure. In some embodiments, an epidermal layer can comprise a keratinocyte and a dermal layer can comprise a fibroblast. In some embodiments, the method can comprise removing at least a portion of an epidermal layer from a layered structure to form a removed product. In some embodiments, the method can comprise tanning at least a portion of a removed product, thereby forming a synthetic leather. In some embodiments, a fibroblast or a keratinocyte can be differentiated from an induced pluripotent stem cell. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can comprise a pigment. In some embodiments, a melanocyte can be a mammalian melanocyte. In some embodiments, a mammal can be a human. In some embodiments, a fibroblast can be differentiated from an induced pluripotent stem cell. In some embodiments, a fibroblast can express CD10, CD73, CD44, CD90, type I collagen, type III collagen, prolyl-4-hydroxylase beta, or a combination thereof. In some embodiments, a removed product can further comprise collagen. In some embodiments, a removed product can be subjected to further processing. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer can further comprise collagen. In some embodiments, an epidermal layer can be subjected to further processing. In some embodiments, a layered structure can further comprise collagen. In some embodiments, a layered structure can be subjected to further processing. In some embodiments, a dermal layer can further comprise collagen. In some embodiments, a dermal layer can be subjected to further processing. In some embodiments, processing can be selected from a group consisting of preserving, soaking, bating, pickling, depickling, thinning, retanning, lubricating, crusting, wetting, sammying, shaving, rechroming, neutralizing, dyeing, fatliquoring, filling, stripping, stuffing, whitening, fixating, setting, drying, conditioning, milling, staking, buffing, finishing, oiling, brushing, padding, impregnating, spraying, roller coating, curtain coating, polishing, plating, embossing, ironing, glazing, tumbling and any combination thereof. In some embodiments, collagen can be produced at least in part by a collagen producing cell, can be separately added, or any combination thereof. In some embodiments, a collagen producing cell can comprise an epithelial cell, a keratinocyte, a fibroblast, a corneocyte, a melanocyte, a Langerhans cell, a basal cell, or a combination thereof. In some embodiments, a collagen producing cell can comprise a epithelial cell wherein the epithelial cell can comprise a squamous cell, a cuboidal cell, a columnar cell, a basal cell, or a combination thereof. In some embodiments, a collagen producing cell can comprise a keratinocyte wherein the keratinocyte can comprise an epithelial keratinocyte, basal keratinocyte, proliferating basal keratinocyte, differentiated suprabasal keratinocyte, or a combination thereof. In some embodiments, a collagen producing cell can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be placed upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can further comprise a basement membrane substitute. In some embodiments, a basement membrane substitute can be between an epidermal layer and a dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a synthetic leather. In some embodiments, a dermal layer or an epidermal layer can be cultured in vitro.

In some embodiments, a dermal layer can be cultured in vitro. In some embodiments, a dermal layer can be cultured with a supplement. In some embodiments, a supplement can comprise one or more of collagen, fibrin, growth factors, ascorbic acid, dextran sulphate, or carrageenan. In some embodiments, a supplement can be a natural supplement. In some embodiments, a supplement can be a synthetic supplement. In some embodiments, an induced pluripotent stem cell can be produced through the induced gene expression of Oct3, Oct4, Sox2, Klf4, c-Myc or a combination thereof in an adult somatic cell. In some embodiments, at least a portion of a leather article can be formed from the methods disclosed herein. In some embodiments, a leather article can comprise one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a leather article can be a watch strap. In some embodiments, a leather article can be a belt. In some embodiments, a leather article can be a bag. At least about 2% of cells comprised in a synthetic leather can be differentiated from an induced pluripotent stem cell. At least about 10% of cells comprised in synthetic leather can be differentiated from an induced pluripotent stem cell. At least about 50% of cells comprised in a synthetic leather can be differentiated from an induced pluripotent stem cell.

Disclosed herein are tanned synthetic leathers. In some embodiments, prior to tanning a tanned synthetic leather can comprise an artificial dermal layer comprising fibroblast. In some embodiments, a fibroblast can be differentiated from an induced pluripotent stem cell. In some embodiments, prior to tanning, a tanned synthetic leather can further comprise an artificial epidermal layer. In some embodiments, an epidermal layer can further comprise a keratinocyte. In some embodiments, an epidermal layer can be upon a dermal layer thereby forming a layered structure. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can further comprise a pigment. In some embodiments, a melanocyte can be a mammalian melanocyte. In some embodiments, a mammal can be a non-human mammal. In some embodiments, a fibroblast can express CD10, CD73, CD44, CD90, type I collagen, type III collagen, prolyl-4-hydroxylase beta, or a combination thereof. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer cam further comprises collagen. In some embodiments, a layered structure can further comprise collagen. In some embodiments, a dermal layer can further comprise collagen. In some embodiments, collagen can be produced at least in part by a collagen producing cell, can be separately added, or any combination thereof. In some embodiments, a collagen producing cell can comprise an epithelial cell, a keratinocyte, a fibroblast, a comeocyte, a melanocyte, a Langerhans cell, a basal cell, or a combination thereof. In some embodiments, a collagen producing cell can comprise an epithelial cell wherein an epithelial cell can comprise a squamous cell, a cuboidal cell, a columnar cell, a basal cell, or a combination thereof. In some embodiments, a collagen producing cell can comprises a keratinocyte wherein a keratinocyte comprises epithelial keratinocyte, basal keratinocyte, proliferating basal keratinocyte, differentiated suprabasal keratinocyte, or a combination thereof. In some embodiments, a collagen producing cells can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can comprise a basement membrane substitute. In some embodiments, a basement membrane substitute can be between an epidermal layer and an dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a tanned synthetic leather. In some embodiments, a dermal layer or an epidermal layer can be cultured in vitro. In some embodiments, a dermal layer can be cultured in vitro. In some embodiments, a tanned synthetic leather can be comprised in one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a tanned synthetic leather can be comprised in a watch strap. In some embodiments, a tanned synthetic leather can be comprised in a belt. In some embodiments, a tanned synthetic leather can be comprised in a bag. At least about 2% of cells comprised in a tanned synthetic leather can be differentiated from an induced pluripotent stem cell. At least about 10% of cells comprised in tanned synthetic leather can be differentiated from an induced pluripotent stem cell. At least about 50% of cells comprised in a tanned synthetic leather can be differentiated from an induced pluripotent stem cell.

Disclosed herein are tanned synthetic leathers. In some embodiments, prior to tanning a tanned synthetic leather can comprise a layered structure. In some embodiments, a layered structure can comprise an artificial dermal layer. In some embodiments, a dermal layer can comprise a fibroblast. In some embodiments, a layered structure can comprise an artificial epidermal layer. In some embodiments an epidermal layer can comprise a keratinocyte. In some embodiments, a fibroblast or a keratinocyte can be differentiated from an induced pluripotent stem cell. In some embodiments, a fibroblast can be differentiated from an induced pluripotent stem cell. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can further comprise a pigment. In some embodiments, a melanocyte can be a mammalian melanocyte. In some embodiments, a mammal can be a non-human mammal. In some embodiments, a fibroblast can express CD10, CD73, CD44, CD90, type I collagen, type III collagen, prolyl-4-hydroxylase beta, or a combination thereof. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer cam further comprises collagen. In some embodiments, a layered structure can further comprise collagen. In some embodiments, a dermal layer can further comprise collagen. In some embodiments, collagen can be produced at least in part by a collagen producing cell, can be separately added, or any combination thereof. In some embodiments, a collagen producing cell can comprise an epithelial cell, a keratinocyte, a fibroblast, a corneocyte, a melanocyte, a Langerhans cell, a basal cell, or a combination thereof. In some embodiments, a collagen producing cell can comprise an epithelial cell wherein an epithelial cell can comprise a squamous cell, a cuboidal cell, a columnar cell, a basal cell, or a combination thereof. In some embodiments, a collagen producing cell can comprises a keratinocyte wherein a keratinocyte comprises epithelial keratinocyte, basal keratinocyte, proliferating basal keratinocyte, differentiated suprabasal keratinocyte, or a combination thereof. In some embodiments, a collagen producing cells can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can comprise a basement membrane substitute. In some embodiments, a basement membrane substitute can be between an epidermal layer and an dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a tanned synthetic leather. In some embodiments, a dermal layer or an epidermal layer can be cultured in vitro. In some embodiments, a dermal layer can be cultured in vitro. In some embodiments, a tanned synthetic leather can be comprised in one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a tanned synthetic leather can be comprised in a watch strap. In some embodiments, a tanned synthetic leather can be comprised in a belt. In some embodiments, a tanned synthetic leather can be comprised in a bag. At least about 2% of cells comprised in a tanned synthetic leather can be differentiated from an induced pluripotent stem cell. At least about 10% of cells comprised in tanned synthetic leather can be differentiated from an induced pluripotent stem cell. At least about 50% of cells comprised in a tanned synthetic leather can be differentiated from an induced pluripotent stem cell.

Disclosed herein are tanned synthetic leathers. In some embodiments, prior to tanning a tanned synthetic leather can comprise a removed product comprising a layered structure. In some embodiments, a layered structure can comprise an artificial dermal layer. In some embodiments, a dermal layer can comprise a fibroblast. In some embodiments, a layered structure can comprise an artificial epidermal layer. In some embodiments, an epidermal layer can comprise a keratinocyte. In some embodiments, a portion of an epidermal layer can be removed. In some embodiments, a fibroblast or a keratinocyte can be differentiated from an induced pluripotent stem cell. In some embodiments, a removed product can further comprise collagen. In some embodiments, a fibroblast can be differentiated from an induced pluripotent stem cell. In some embodiments, a keratinocyte can be a mammalian keratinocyte. In some embodiments, a mammal can be a non-human mammal. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a layered structure can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a synthetic leather can further comprise a pigment. In some embodiments, a melanocyte can be a mammalian melanocyte. In some embodiments, a mammal can be a non-human mammal. In some embodiments, a fibroblast can express CD10, CD73, CD44, CD90, type I collagen, type III collagen, prolyl-4-hydroxylase beta, or a combination thereof. In some embodiments, a fibroblast can be a mammalian fibroblast. In some embodiments, a mammal can be a non-human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, an epidermal layer cam further comprises collagen. In some embodiments, a layered structure can further comprise collagen. In some embodiments, a dermal layer can further comprise collagen. In some embodiments, collagen can be produced at least in part by a collagen producing cell, can be separately added, or any combination thereof. In some embodiments, a collagen producing cell can comprise an epithelial cell, a keratinocyte, a fibroblast, a comeocyte, a melanocyte, a Langerhans cell, a basal cell, or a combination thereof. In some embodiments, a collagen producing cell can comprise an epithelial cell wherein an epithelial cell can comprise a squamous cell, a cuboidal cell, a columnar cell, a basal cell, or a combination thereof. In some embodiments, a collagen producing cell can comprises a keratinocyte wherein a keratinocyte comprises epithelial keratinocyte, basal keratinocyte, proliferating basal keratinocyte, differentiated suprabasal keratinocyte, or a combination thereof. In some embodiments, a collagen producing cells can comprise a smooth muscle cell. In some embodiments, a synthetic leather can further comprise one or more of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a synthetic leather can further comprise a first dermal layer and a second dermal layer. In some embodiments, a first dermal layer can be upon a second dermal layer. In some embodiments, a thickness of an epidermal layer can range from about 0.01 mm to about 2 mm. In some embodiments, a thickness of an epidermal layer can range from about 0.1 mm to about 0.2 mm. In some embodiments, a synthetic leather can further comprise a first epidermal layer and a second epidermal layer. In some embodiments, a synthetic leather can comprise a basement membrane substitute. In some embodiments, a basement membrane substitute can be between an epidermal layer and an dermal layer. In some embodiments, a basement membrane substitute can comprise a dried acellular amniotic membrane. In some embodiments, a dermal layer can be formed upon a scaffold. In some embodiments, a scaffold can be natural or synthetic. In some embodiments, a scaffold can comprise silk. In some embodiments, a scaffold can comprise chitosan. In some embodiments, a scaffold can comprise a natural tissue adhesive. In some embodiments, a natural tissue adhesive can comprise fibrin glue. In some embodiments, a scaffold can be comprised in part in a tanned synthetic leather. In some embodiments, a dermal layer or an epidermal layer can be cultured in vitro. In some embodiments, a dermal layer can be cultured in vitro. In some embodiments, a tanned synthetic leather can be comprised in one or more of a watch strap, a belt, a packaging, a shoe, a boot, a footwear, a glove, a clothing, a luggage, a bag, a clutch, a purse, a backpack, a wallet, a saddle, a harness, a whip, an interior, an exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. In some embodiments, a tanned synthetic leather can be comprised in a watch strap. In some embodiments, a tanned synthetic leather can be comprised in a belt. In some embodiments, a tanned synthetic leather can be comprised in a bag. At least about 2% of cells comprised in a tanned synthetic leather can be differentiated from an induced pluripotent stem cell. At least about 10% of cells comprised in tanned synthetic leather can be differentiated from an induced pluripotent stem cell. At least about 50% of cells comprised in a tanned synthetic leather can be differentiated from an induced pluripotent stem cell.

Disclosed herein are artificial epidermal layers. In some embodiments, an artificial epidermal layer can comprise a hair follicle cell and a melanocyte. In some embodiments, an artificial epidermal layer can comprise a hair follicle cell. In some embodiments, an artificial epidermal layer can comprise a melanocyte. In some embodiments, a melanocyte can be differentiated from an induced pluripotent stem cell. In some embodiments, a hair follicle cell can comprises a dermal papilla cell, an outer root sheath cell or a combination thereof. In some embodiments, a melanocyte can be a mammalian melanocyte. In some embodiments, an epidermal layer can further comprise a keratinocyte. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a keratinocyte can be a mammalian keratinocyte. In some embodiments, a mammal can be a non-human mammal. In some embodiments, a mammal can be a human mammal. In some embodiments, a non-human mammal can be one of a primate, bovine, ovine, porcine, equinine, canine, feline, rodent, or lagomorph. In some embodiments, a fibroblast can be a non-mammalian fibroblast. In some embodiments, a non-mammal can be a fish, a bird or a reptile. In some embodiments, a melanocyte can express Sox-10, MITF-M, gp-100, DCT, TYR, MLANA or a combination thereof. In some embodiments, an epidermal layer can comprise a hair follicle. At least about 2% of cells comprised in an artificial epidermal layer can be differentiated from an induced pluripotent stem cell. At least about 10% of cells comprised in an artificial epidermal layer can be differentiated from an induced pluripotent stem cell. At least about 50% of cells comprised in a artificial epidermal layer can be differentiated from an induced pluripotent stem cell.

Disclosed herein are layered structures. In some embodiments, a layered structure can comprise an artificial epidermal layer. In some embodiments, an epidermal layer can comprise a hair follicle cell. In some embodiments, a layered structure can comprise an artificial dermal layer. In some embodiments, a dermal layer can comprise a fibroblast. In some embodiments, a fibroblast can be differentiated from an induced pluripotent stem cell. In some embodiments, a fibroblast can express CD10, CD73, CD44, CD90, type I collagen, type III collagen, prolyl-4-hydroxylase beta, or a combination thereof. In some embodiments, an epidermal layer can further comprise a keratinocyte. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a hair follicle cell can be a dermal papilla cell, outer root sheath cell or a combination thereof. In some embodiments, an epidermal layer can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a layered structure can be pigmented. In some embodiments, an epidermal layer can be stratified. In some embodiments, a layered structure can comprise a basement membrane substitute. In some embodiments, a basement membrane substitute can be between an epidermal layer and a dermal layer. In some embodiments, a basement membrane substitute can comprise a dried acellular amniotic membrane. In some embodiments, a layered structure can further comprise a scaffold. In some embodiments, a scaffold can be natural or synthetic. In some embodiments, a scaffold can comprise silk. In some embodiments, a scaffold can comprise chitosan. In some embodiments, a dermal layer can be upon a scaffold. In some embodiments, a layered structure can comprise one or more components selected from a group consisting of keratin, elastin, gelatin, proteoglycan, dermatan sulfate proteoglycan, glycosoaminoglycan, fibronectin, laminin, dermatopontin, lipid, fatty acid, carbohydrate, or a combination thereof. In some embodiments, a layered structure can further comprise two or more dermal layers. In some embodiments, a layered structure can further comprise a hair follicle. In some embodiments, a layered structure can further comprise a fur. At least about 2% of cells comprised in a layered structure can be differentiated from an induced pluripotent stem cell. At least about 10% of cells comprised in a layered structure can be differentiated from an induced pluripotent stem cell. At least about 50% of cells comprised in layered structure can be differentiated from an induced pluripotent stem cell.

Disclosed herein are methods for making a layered structure. In some embodiments, the method can comprise placing an artificial epidermal layer comprising a hair follicle cell upon an artificial dermal layer comprising a cell differentiated from an induced pluripotent stem cell thereby forming a layered structure. In some embodiments, a cell differentiated from an induced pluripotent stem cell can be a fibroblast, melanocyte, keratinocyte or a combination thereof. In some embodiments, a cell differentiated from an induced pluripotent stem cell can be a fibroblasts. In some embodiments, a fibroblast can express CD10, CD73, CD44, CD90, type I collagen, type III collagen, prolyl-4-hydroxylase beta, or a combination thereof. In some embodiments, an epidermal layer can further comprise a keratinocyte. In some embodiments, a keratinocyte can be differentiated from an induced pluripotent stem cell. In some embodiments, a keratinocyte can express KRT14, p63, DSG3, ITGB4, LAMA5, KRT5, TAp63, Lamb3, KRT18 or a combination thereof. In some embodiments, a hair follicle cell can comprise a dermal papilla cell, an outer root sheath cell or a combination thereof. In some embodiments, an epidermal layer can further comprise a melanocyte. In some embodiments, a melanocyte can be differentiated from an induced pluripotent stem cell. In some embodiments, a melanocyte can express Sox-10, MITF-M, gp-100, DCT, TYR, MLANA or a combination thereof. In some embodiments, a dermal layer can be cultured with a supplement. In some embodiments, a supplement can comprise collagen, fibrin, growth factors, ascorbic acid, dextran sulphate, carrageenan or a combination thereof. In some embodiments, a supplement can be a natural supplement. In some embodiments, a supplement can be a synthetic supplement. In some embodiments, a dermal layer can be cultured upon a scaffold. In some embodiments, a scaffold can be natural or synthetic. In some embodiments, a scaffold can comprise silk. In some embodiments, a scaffold can comprise chitosan. In some embodiments, a dermal layer can be placed upon a scaffold. In some embodiments, an epidermal layer can be stratified. In some embodiments, a dermal layer can be cultured upon a second dermal layer. In some embodiments, a dermal layer can be cultured in vivo. In some embodiments, a dermal layer may not be cultured upon a collagen matrix. In some embodiments, a thickness of a dermal layer can range from about 0.02 mm to about 5 mm. In some embodiments, a thickness of a dermal layer can range from about 0.1 mm to about 0.5 mm. In some embodiments, a thickness of an epidermal layer can range from about 0.01 mm to about 2 mm. In some embodiments, a thickness of an epidermal layer can range from about 0.1 mm to about 0.2 mm. At least about 2% of cells comprised in a layered structure can be differentiated from an induced pluripotent stem cell. At least about 10% of cells comprised in a layered structure can be differentiated from an induced pluripotent stem cell. At least about 50% of cells comprised in layered structure can be differentiated from an induced pluripotent stem cell.

Disclosed herein are layered structures. In some embodiments, a layered structure can comprise an artificial epidermal layer comprising a hair follicle cell and a keratinocyte or a melanocyte; an artificial dermal layer comprising a fibroblast, wherein a fibroblast, a keratinocyte or a melanocyte can be differentiated from an induced pluripotent stem cell, wherein a melanocyte expresses Sox-10, MITF-M, gp-100, DCT, TYR, MLANA or a combination thereof, wherein a fibroblast expresses CD10, CD73, CD44, CD90, type I collagen, type III collagen, prolyl-4-hydroxylase beta, or a combination thereof, wherein a keratinocyte expresses KRT14, p63, DSG3, ITGB4, LAMA5, KRT5, TAp63, Lamb3, KRT18 or a combination thereof. In some embodiments, a layered structure can comprise an artificial epidermal layer. In some embodiments, an epidermal layer can comprise a hair follicle cell. In some embodiments, an epidermal layer can comprise a keratinocyte or a melanocyte. In some embodiments, a layered structure can comprise an artificial dermal layer. In some embodiment, a dermal layer can comprise a fibroblast. In some embodiments, a fibroblast, a keratinocyte or a melanocyte can be differentiated from an induced pluripotent stem cell. In some embodiments, a melanocyte can express Sox-10, MITF-M, gp-100, DCT, TYR, MLANA or a combination thereof. In some embodiments, a fibroblast can express CD10, CD73, CD44, CD90, type I collagen, type III collagen, prolyl-4-hydroxylase beta, or a combination thereof. In some embodiments, a keratinocyte can express KRT14, p63, DSG3, ITGB4, LAMA5, KRT5, TAp63, Lamb3, KRT18 or a combination thereof. In some embodiments, a thickness of a dermal layer can range from about 0.02 mm to about 5 mm. In some embodiments, a thickness of a dermal layer can range from about 0.1 mm to about 0.5 mm. In some embodiments, a thickness of an epidermal layer can range from about 0.01 mm to about 2 mm. In some embodiments, a thickness of an epidermal layer can range from about 0.1 mm to about 0.2 mm. At least about 2% of cells comprised in a layered structure can be differentiated from an induced pluripotent stem cell. At least about 10% of cells comprised in a layered structure can be differentiated from an induced pluripotent stem cell. At least about 50% of cells comprised in layered structure can be differentiated from an induced pluripotent stem cell.

Disclosed herein are artificial epidermal layer. An artificial epidermal layer can comprise a stratum corneum. An artificial epidermal layer can comprise a stratum granulosum. An artificial epidermal layer can comprise a stratum spinosum. An artificial epidermal layer can comprise a stratum basale. In some embodiments a stratum corneum, a stratum granulosum, a stratum spinosum, or a stratum basale can be organized as depicted in FIG. 6A, or FIG. 8A. A thickness of a stratum corneum can range from about 0.01 mm to about 0.05 mm. A thickness of astratum granulosum can range from about 0.01 mm to about 0.15 mm. A thickness of a stratum spinosum can range from about 0.01 mm to about 0.15 mm. A thickness of said stratum basale can range from about 0.01 mm to about 0.15 mm. A thickness of a stratum corneum can range from about 4% to about 20% of an artificial epidermal layer. A thickness of a stratum granulosum can range from about 4% to about 60% of a artificial epidermal layer. A thickness of a stratum spinosum can range from about 4% to about 40% of a artificial epidermal layer. A thickness of a stratum basale can range from about 4% to about 40% of an artificial epidermal layer. At least about 2% of cells comprised in an artificial epidermal layer can be differentiated from an induced pluripotent stem cell. At least about 10% of cells comprised in an artificial epidermal layer can be differentiated from an induced pluripotent stem cell. At least about 50% of cells comprised in a artificial epidermal layer can be differentiated from an induced pluripotent stem cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 2A depicts a layered structure comprising an epidermal layer and a dermal layer on a scaffold. FIG. 2B depicts a layered structure comprising an epidermal layer, a basement membrane substitute and a dermal layer on a scaffold. FIG. 2C depicts a layered structure comprising an epidermal layer and multiple dermal layers on a scaffold. FIG. 2D depicts a layered structure comprising an epidermal layer, a basement membrane substitute and multiple dermal layers on a scaffold.

FIG. 2E depicts a layered structure comprising an epidermal layer, a basement membrane substitute and multiple dermal layers. FIG. 2F depicts a layered structure comprising an epidermal layer and multiple dermal layers.

FIG. 3 illustrates a layered structure development.

FIG. 5A depicts an epidermal surface image. FIG. 5B depicts a corneo-desmosome image. FIG. 5C depicts a CDSN/Hoechst image.

FIGS. 6A-6E illustrate a comparative analysis of stratum granulosum of native skin and epidermal equivalent. FIG. 6A depicts a Loricrin (LOR) staining. FIG. 6B depicts an epidermal $Ca^{++}$ gradient captured on transmission electron microscopy as electron-dense precipitates. FIG. 6C depicts an assessment of permeability barrier integrity by lanthanum perfusion. FIG. 6D illustrates that tight junction protein 1/zonula occludens-1 (TJP1/ZO-1) anchors tight junction strand proteins, which can be fibril-like structures within the lipid bilayer, to the actin cytoskeleton. FIG. 6E illustrates that Filaggrin (FLG) monomers, tandemly clustered into a large, 350 kDa protein precursor known as profilaggrin, are present in the keratohyalin granules in cells of the SG.

FIGS. 7A-7C illustrate a Lipid bilayer formation in native skin and epidermal equivalent assessed with TEM. FIG. 7A depicts normal lipid secretion at the border of SC and SG. FIG. 7B depicts lamellar bodies in the SG. FIG. 7C depicts normal lipid bilayer (LB) morphology of native skin.

FIGS. 8A-8C illustrate a comparative analysis of markers of suprabasal layers of native skin and epidermal equivalent, including Keratin 10 (KRT10; FIG. 8A), keratin 1 (KRT1; FIG. 8B), desmocollin 1 (DCL1; FIG. 8C), markers of suprabasal layers. FIG. 8D depicts Desmosomes in both native skin in vivo and epidermal equivalents generated in vitro.

FIG. 9B), and transcription factor TP63 (FIG. 9C) show typical basal layer distribution in both native skin in vivo (left side of panel) and epidermal equivalents generated in vitro.

FIG. 10A depicts Integrin 131 expression. FIG. 10B depicts fibronectin expression. FIG. 10C depicts collagen IV expression. FIG. 10D depicts collagen VI expression. FIG. 10E depicts collagen VII expression. FIG. 10F depicts Laminin 5 expression.

FIGS. 11A and 11B depict cross sections of FSE displays distinct cellular layers of epidermis under 2600× magnification (FIG. 11A) and 5200× magnification (FIG. 11B). FIG. 11C depicts a surface of an FSE at 900× magnification. FIGS. 11D-1F depict longitudinal sections of dermal scaffold with residing dermal fibroblasts and rich extracellular matrix at 91× magnification (FIG. 11D), 162× magnification (FIG. 11E) and 405× magnification (FIG. 11F). FIGS. 11G-11I depict dermal scaffolds with residing dermal fibroblasts and rich extracellular matrix at 80× magnification (FIG. 11G), 695× magnification (FIG. 11H) and 2700× magnification (FIG. 11I).

FIGS. 12A-12 I depict day 2 after seeding dermal fibroblasts onto scaffold at 36× magnification (FIG. 12A), 695× magnification (FIG. 12B), 1470× magnification (FIG. 12C), 7750× magnification (FIG. 12D), 2320× magnification (FIG. 12E), 2420× magnification (FIG. 12F), 6560× magnification (FIG. 12G), 17000× magnification (FIG. 12H) and 22000× magnification (FIG. 12I). FIGS. 12J-12 R depict day 7 after seeding dermal fibroblasts onto scaffold at 64× magnification (FIG. 12J), 100× magnification (FIG. 12K), 364× magnification (FIG. 12L), 82× magnification (FIG. 12M), 253× magnification (FIG. 12N), 3940× magnification (FIG. 12O), 5550× magnification (FIG. 12P), 9440× magnification (FIG. 12Q) and 21680 magnification (FIG. 12R).

DETAILED DESCRIPTION OF THE DISCLOSURE

Figure 1:
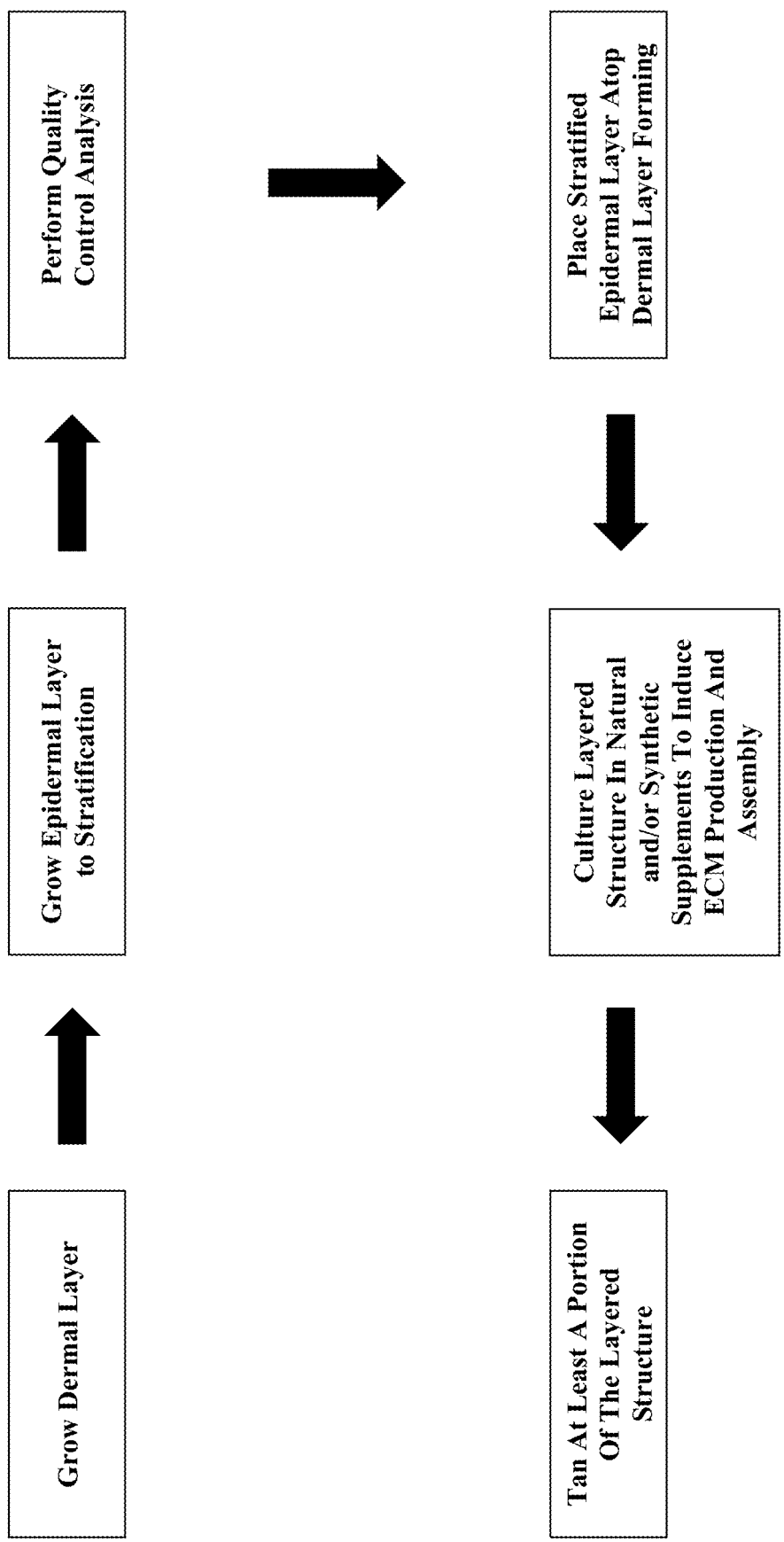
FIG. 1 illustrates a synthetic leather production schematic.
Figure 2A:
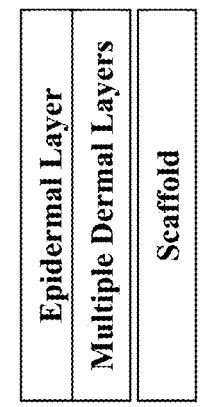
FIGS. 2A-2F illustrate a layered structure.
Figure 2B:
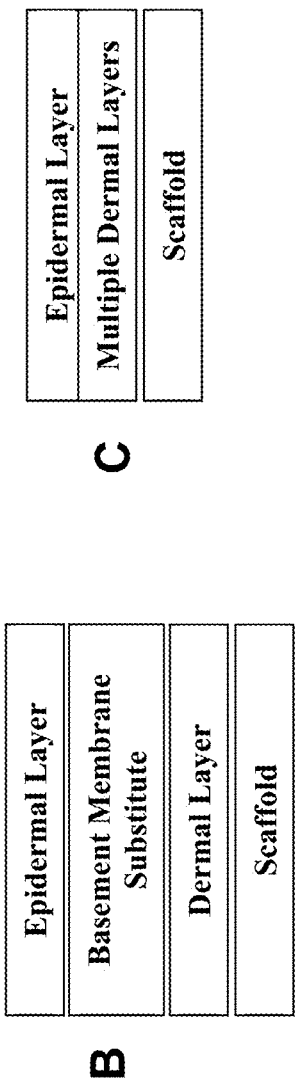
Figure 2C:
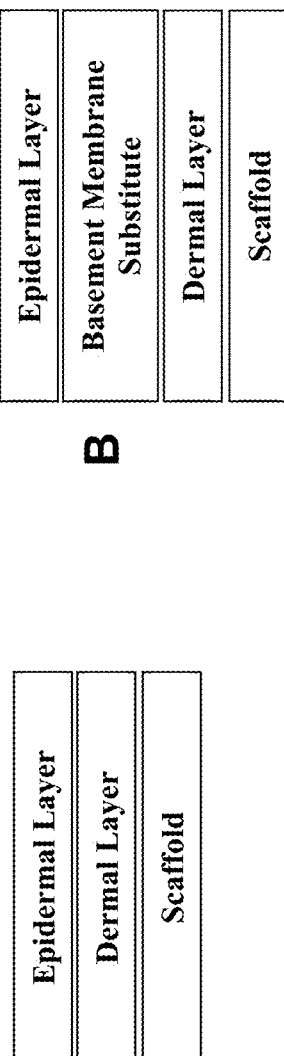
Figure 2D:
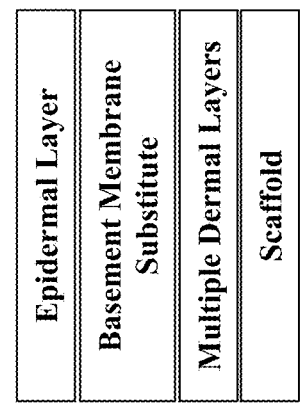
Figure 2E:
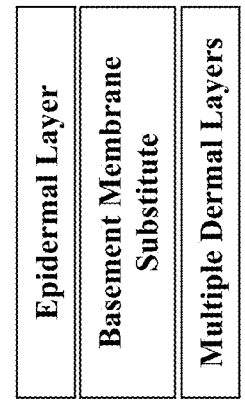
Figure 2F:
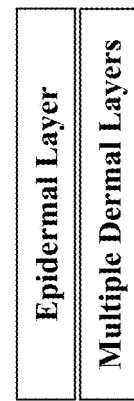

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events, unless otherwise specifically indicated. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

In this disclosure the term "about" or "approximately" can mean a range of up to 10% of a given value. In this disclosure the term "substantially" refers to something that can be done to a great extent or degree.

As used herein, the term "pluripotent stem cell" can refer to any precursor cell that has the ability to form any adult cell.

As used herein, the term "embryonic stem cells" or "ES cells" or "ESC" can refer to precursor cells that have the ability to form any adult cell.

As used herein, the term "induced pluripotent stem cells" or "iPS cells" or "iPSCs" can refer to a type of pluripotent stem cell artificially derived from a non-pluripotent cell (e.g., an adult somatic cell). Induced pluripotent stem cells can be identical to embryonic stem cells in the ability to form any adult cell, but are not derived from an embryo. In some cases, IPSC cells disclosed herein can be IPSC cells.

As used herein, the term "synthetic leather" can mean that the skin equivalents described herein can serve as a skin equivalent for any mammal or non-mammal. Embodiments can be practiced with human and non-human mammals, such as non-human primates and members of the bovine, ovine, porcine, equinine, canine and feline species as well as rodents such as mice, rats and guinea pigs, members of the lagomorph family including rabbit; and non-mammals such as fish including shark and stingray, birds including ostrich and reptiles including lizards, snakes and crocodiles. The particular mammalian synthetic leather which will be formed can be dependent on the source of the cells used in embodiments described herein, e.g. Keratinocytes and fibroblasts, e.g., when bovine keratinocytes and fibroblasts are used to form a skin equivalent, a bovine synthetic leather can be formed.

Overview

Disclosed herein are synthetic leathers, artificial epidermal layers, artificial dermal layers, layered structures, products made thereof and methods of producing the same. In certain cases, disclosed herein are synthetic leathers. In some cases, a synthetic leather comprises one or a plurality of layers. In some cases, one or a plurality of layers comprises cells, wherein said cells are cultured in vitro. In some cases, the methods described herein provide high-throughput methods that reliably, accurately, and reproducibly scale up to commercial levels the production of synthetic leather. Advantages of the synthetic leather, engineered epidermal equivalent, engineered full thickness skin equivalent and methods of making the same disclosed herein include, but are not limited to, production of customized tissues in a reproducible, high throughput and easily scalable fashion with appealing appearance, texture, thickness, and durability. As used herein, full thickness skin equivalent can comprise at least one dermal layer and at least one epidermal layer. As used herein, full thickness skin equivalent and full skin equivalent can be used interchangeably.

A synthetic leather disclosed herein can comprise a layer of artificial dermal layer comprising a fibroblast and an artificial epidermal layer comprising a keratinocyte. The dermal layer and the epidermal layer can form a layered structure. A synthetic leather can comprise one or more layered structure. The synthetic leather can be tanned and further processed. The cells forming the synthetic layer can be differentiated from stem cells, e.g., induced pluripotent stem cells (iPSC). The dermal layer can be placed on a scaffold, such as silk, to achieve natural leather thickness and texture.

Also disclosed herein are methods of making a synthetic leather. The method can comprise forming a layered structure comprising an artificial dermal layer and an artificial epidermal layer, and tanning the layered structure. The methods can also comprise further processing the artificial dermal layers and epidermal layers, e.g., to achieve natural leather thickness and texture.

Synthetic Leather

A synthetic leather can comprise one or more cell layers. For example, a synthetic leather can comprise one or more of: a dermal layer, an epidermal layer, and a basement membrane or a basement membrane substitute. A synthetic leather can further comprise hypodermis, scale, scute, osteoderm, or a combination thereof. In some cases, a synthetic layer comprises a full thickness skin equivalent. Such full thickness skin equivalent can comprise any one or combination of the layers disclosed herein. A portion of one or more cell layers in a synthetic leather can be removed, e.g., by shaving. In some cases, a synthetic leather can be tanned. The tanning can be performed after formation of one or more of the cell layers or layered structures. The tanning can be performed after at least a portion of a cell layer can be removed from a synthetic leather. In some cases, a synthetic leather can be further processed. In some cases, a synthetic leather can comprise a hair follicle cell and a melanocyte. The hair follicle cell and/or the melanocyte can be differentiated from a stem cell (e.g., an iPSC).

In some embodiments, a tanned synthetic leather can comprise a layered structure. A layered structure can comprise an artificial dermal layer comprising a fibroblast. A layered structure can also comprise an artificial epidermal layer comprising a keratinocyte. In some cases, a layered structure can comprise an artificial dermal layer comprising a fibroblast and an artificial epidermal layer comprising a keratinocyte. In some cases, a fibroblast or a keratinocyte can be differentiated from an induced pluripotent stem cell.

In some cases, a tanned synthetic leather can comprise at least part of a dermal layer. In some cases, a tanned synthetic leather does not comprise a dermal layer. In some cases, a dermal layer can be removed.

Dermal Layer

A synthetic leather can comprise a dermal layer (e.g., an artificial dermal layer). A dermal layer can be an engineered dermis equivalent, e.g., an artificial dermal layer formed in vitro.

A dermal layer can comprise cells of connective tissue. For example, a dermal layer can comprise fibroblasts. Fibroblasts in the dermal layer can express one or more markers including, but not limited to, cluster of differentiation 10 (CD10), cluster of differentiation 73 (CD73), cluster of differentiation 44 (CD44), cluster of differentiation 90 (CD90), type I collagen, type III collagen, and prolyl-4-hydroxylase beta fibroblasts. In some cases, a dermal layer also comprises other types of cells, such as immune cells, macrophages, adipocytes, or a combination thereof.

A dermal layer can further comprise matrix components in addition to cells. Examples of matrix components include but are not limited to any one or more of collagen, elastin, and extrafibrillar matrix, an extracellular gel-like substance primarily composed of glycosaminoglycans (e.g., hyaluronan), proteoglycans, and glycoproteins.

A dermal layer can comprise a matrix support. A matrix support can be a scaffold. The matrix support can comprise contracted collagen gels. Alternatives to a pure collagen matrix can be a polyglygolic acid mesh, e.g., as described in Hansbrough, et al., J. Burn Care Rehabil., 15:346-53 (1994), or collagen and glycosaminoglycan matrix covered with a silastic membrane (C-GAG), e.g., as described in Burke, et al., Ann. Surg., 194:413-420 (1981) or various biopolymers, e.g. chitosan as described in Kellouche, et al., Biochem Biophys Res Commun., 363:472-478 (2007). In some cases, the matrix can be seeded with fibroblasts, e.g., to give rise to organotypic models. Naturally derived dermis, from allogenic cadaver skin can also be used with keratinocyte sheets. A variation of this technique can use lyophilized devitalized dermis from cadaver skin to support the keratinocyte sheets.

The thickness of leather units may be reported in millimeters, ounces, or irons. (One ounce equals 1/64 in. or 0.0156 in. or 0.396 mm. One iron equals 1/48 in. or 0.0208 in. or 0.53 mm.)

The thickness of a dermal layer can be engineered to fit the function or use of a synthetic leather. A dermal layer can have a thickness from about 0.01 mm to about 50 mm. For example, a dermal layer can have a thickness from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a dermal layer can have a thickness from about 0.02 mm to 5 mm. For example, a dermal layer can have a thickness from about 0.1 mm to 0.5 mm. For example, a dermal layer can have a thickness from about 0.2 mm to 0.5 mm. In some cases, the thickness of a dermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the thickness of a dermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a dermal layer can have a thickness of at least about 50 mm.

The length of a dermal layer can be engineered to fit the function or use of a synthetic leather. A dermal layer can have a length from about 0.01 mm to about 50 m. For example, a dermal layer can have a length from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a dermal layer can have a length from about 0.02 mm to 5 mm. For example, a dermal layer can have a length from about 0.1 mm to 0.5 mm. For example, a dermal layer can have a length from about 0.2 mm to 0.5 mm. In some cases, the length of a dermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the length of a dermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a dermal layer can have a length of at least about 50, 60, 70, 80, 90, 100, 200, 300, 400, 500, 700, 1000 mm. In some embodiments, a dermal layer can have a length of at least about 50, 60, 70, 80, 90, 100, 200, 300, 400, 500, 600, 700 cm. In some embodiments, a dermal layer can have a length of at least about 50, 60, 70, 80, 90, 100, 200, 300, 400 m.

The width of a dermal layer can be engineered to fit the function or use of a synthetic leather. A dermal layer can have a width from about 0.01 mm to about 50 m. For example, a dermal layer can have a width from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a dermal layer can have a width from about 0.02 mm to 5 mm. For example, a dermal layer can have a width from about 0.1 mm to 0.5 mm. For example, a dermal layer can have a width from about 0.2 mm to 0.5 mm. In some cases, the width of a dermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the width of a dermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a dermal layer can have a width of at least about 50, 60, 70, 80, 90, 100, 200, 300, 400, 500, 700, 1000 mm. In some embodiments, a dermal layer can have a width of at least about 50, 60, 70, 80, 90, 100, 200, 300, 400, 500, 600, 700 cm. In some embodiments, a dermal layer can have a width of at least about 50, 60, 70, 80, 90, 100, 200, 300, 400 m.

A synthetic leather can comprise one or more dermal layers. For example, a synthetic leather can have at least 1, 2, 3, 4, 5, 6, 7, 8, 9, 10, 12, 14, 16, 18, 20, 40, 60, 80, or 100 dermal layers. When a synthetic leather comprises more than one dermal layer, a dermal layer can be placed upon another dermal layer. For example, a synthetic leather can comprise two dermal layers, e.g., a first dermal layer and a second dermal layer. The first dermal layer can be placed upon the second dermal layer.

A dermal layer can be stratified, e.g., having a plurality of sublayers. The sublayers can have different compositions, e.g., different concentrations of the fibers. The sublayers of a dermal layer can have different thicknesses and densities. For example, a dermal layer can have a papillary dermal layer, a reticular dermal layer, or any combination thereof. A papillary dermal layer can comprise loose areolar connective tissue and/or loosely arranged fibers, e.g., collagen fibers. A reticular dermal layer can comprise dense irregular connective tissue, including collagen fibers and dermal elastic fibers.

A dermal layer can comprise a free collagen matrix or lattice, which can be contractile in all directions, and homogeneous. Fibroblasts, and where appropriate other types of cells of the dermis, can be distributed in a continuous collagen gel. The dermis equivalent can comprise at least one matrix of collagen type I in which the fibroblasts are distributed. It can also contain other extracellular matrix constituents. Extracellular matrix constituent can include collagens, e.g., collagen IV, laminins, entactin, fibronectin, proteoglycans, glycosaminoglycans or hyaluronic acid. A dermal layer can contain collagen type IV and laminin, entactin, or a combination thereof. The concentrations of these various constituents can be adjusted. For example, the concentration of laminin can be from about 1% to about 15% of the final volume. For example, the concentration of collagen IV can be from about 0.3% to about 4.5% of the final volume. For example, the concentration of entactin can be from about 0.05% to about 1% of the final volume. The collagen used can be collagen of bovine origin, from rat tail or from fish, or any other source of natural collagen or collagen produced by genetic engineering which allows contraction in the presence of fibroblasts. In some embodiments, collagen can be from an unnatural source. The matrix can be a gel of collagen which may not taut, obtained by contraction both horizontally and vertically, which does not impose a preferential organization of the fibroblasts. Such a matrix, also termed "free", may not adhere to the support and the volumes thereof can be modified without limit, conferring on it a varying thickness and diameter. The thickness of the dermis equivalent can be at least 0.05 cm and in some cases approximately from 0.05 to 2 cm. The thickness can also be increased without harming the advantageous properties of the skin equivalent or synthetic leather. In some cases, the thickness can be from about 3 mm to about 20 cm or more.

Epidermal Layer

A synthetic leather can comprise an epidermal layer (e.g., an artificial epidermal layer). An epidermal layer can be an engineered epidermis equivalent, e.g., an artificial epidermal layer formed in vitro.

An epidermal layer can comprise one or more types of cells, including keratinocytes, melanocytes, Langerhans cells, Merkel cells, and inflammatory cells. For example, an epidermal layer can comprise keratinocytes. Keratinocytes in an epidermal layer can include epithelial keratinocytes, basal keratinocytes, proliferating basal keratinocytes, differentiated suprabasal keratinocytes, or any combination thereof.

In some cases, an epidermal layer comprises at least basal keratinocytes, e.g., keratinocytes which are not differentiated. An epidermal layer can further comprise partially differentiated keratinocytes as well as fully differentiated keratinocytes. In one or more epidermal layers in a synthetic leather there can be a transition from undifferentiated basal keratinocytes to fully differentiated keratinocytes as one progresses from the dermal-epidermal junction where the basal keratinocytes are localized.

Basal keratinocytes can express hemidesmosomes, which serve to help secure the epidermal and dermal layers together. Basal keratinocytes can also serve to regenerate the skin. An epidermal layer in a synthetic leather herein can have basal keratinocytes that serve these functions. Thus, a synthetic leather comprising such basal keratinocytes can be capable of regeneration. Other distinctions between basal keratinocytes and differentiated keratinocytes in one or more epidermal layers in a synthetic leather can be that both E- and P-cadherin's are present in epidermal keratinocytes along the basal membrane zone (BMZ), but keratinocytes which are differentiated and located away from the BMZ only express E-cadherin.

The basal keratinocytes of an epidermal layer can be aligned in a layer in direct contact with the dermal layer, serving as the boundary between the differentiated keratinocytes and the fibroblasts. In alternative cases, there are gaps between the basal keratinocytes and the dermal layer. Still further, there can be gaps between the basal keratinocytes and other basal keratinocytes, leaving gaps between the differentiated keratinocytes and the dermal layer. In these latter cases where there are gaps between the basal or differentiated keratinocytes and the dermal layer, the dermal and epidermal layers are not uniformly in contact with one another, but are adjacent to each other. They are adjacent in that there can be generally fluid, but substantially no other intervening materials such as layers of cells, collagen, matrices or other supports between the dermal and epidermal layers.

Keratinocytes in an epidermal layer can express one or more markers. Such markers include, but are not limited to, Keratin 14 (KRT14), tumor protein p63 (p63), Desmoglein 3 (DSG3), Integrin, beta 4 (ITGB4), Laminin, alpha 5 (LAMA5), Keratin 5 (KRT5), an isoform of tumor protein p63 (e.g., TAp63), Laminin, beta 3 (LAMB3), and Keratin 18 (KRT18).

The thickness of an epidermal layer can be engineered to fit the function or use of the synthetic leather. An epidermal layer can have a thickness from about 0.001 mm to about 10 mm. For example, an epidermal layer can have a thickness from about 0.005 mm to about 10 mm, from about 0.005 mm to about 5 mm, from about 0.005 mm to about 2 mm, from about 0.01 mm to about 10 mm, from about 0.01 mm to about 5 mm, from about 0.01 mm to about 2 mm, from about 0.01 mm to about 1, from about 0.01 mm to about 0.8 mm, from about 0.01 mm to about 0.4 mm, from about 0.01 mm to about 0.2 mm, from about 0.01 mm to about 0.1 mm, from about 0.05 mm to about 0.4 mm, from about 0.05 mm to about 0.2 mm, from about 0.05 mm to about 0.1 mm, from about 0.1 mm to about 0.4 mm, from about 0.1 mm to about 0.2 mm, from about 0.08 mm to about 1 mm, or from about 0.05 mm to about 1.5 mm. For example, an epidermal layer can have a thickness from about 0.01 mm to about 2 mm. For example, an epidermal layer can have a thickness from about 0.1 mm to about 0.22 mm. In some cases, the thickness of an epidermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the thickness of the dermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some cases, thickness values described herein can be the thickness of an epidermal layer and a basement membrane substitute.

The length of an epidermal layer can be engineered to fit the function or use of a synthetic leather. An epidermal layer can have a length from about 0.01 mm to about 50 m. For example, an epidermal layer can have a length from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, an epidermal layer can have a length from about 0.02 mm to 5 mm. For example, an epidermal layer can have a length from about 0.1 mm to 0.5 mm. For example, an epidermal layer can have a length from about 0.2 mm to 0.5 mm. In some cases, the length of an epidermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the length of an epidermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, an epidermal layer can have a length of at least about 50, 60, 70, 80, 90, 100, 200, 300, 400, 500, 700, 1000 mm. In some embodiments, an epidermal layer can have a length of at least about 50, 60, 70, 80, 90, 100, 200, 300, 400, 500, 600, 700 cm. In some embodiments, an epidermal layer can have a length of at least about 50, 60, 70, 80, 90, 100, 200, 300, 400 m.

The width of an epidermal layer can be engineered to fit the function or use of a synthetic leather. An epidermal layer can have a width from about 0.01 mm to about 50 m. For example, an epidermal layer can have a width from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, an epidermal layer can have a width from about 0.02 mm to 5 mm. For example, an epidermal layer can have a width from about 0.1 mm to 0.5 mm. For example, an epidermal layer can have a width from about 0.2 mm to 0.5 mm. In some cases, the width of an epidermal layer can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the width of an epidermal layer can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, an epidermal layer can have a width of at least about 50, 60, 70, 80, 90, 100, 200, 300, 400, 500, 700, 1000 mm. In some embodiments, an epidermal layer can have a width of at least about 50, 60, 70, 80, 90, 100, 200, 300, 400, 500, 600, 700 cm. In some embodiments, an epidermal layer can have a width of at least about 50, 60, 70, 80, 90, 100, 200, 300, 400 m.

A synthetic leather can comprise one or more epidermal layers. For example, a synthetic leather can have at least about 1, 2, 3, 4, 5, 6, 7, 8, 9, 10, 12, 14, 16, 18, 20, 40, 60, 80, or 100 epidermal layers. When a synthetic leather comprises more than one epidermal layer, one epidermal layer can be placed upon another epidermal layer. For example, a synthetic leather can comprise two epidermal layers, e.g., a first epidermal layer and a second epidermal layer. The first epidermal layer can be placed upon the second epidermal layer.

An epidermal layer can be stratified, e.g., having a plurality of sublayers. The sublayers can have different cell compositions, e.g., different types of keratinocytes. The sublayers of an epidermal layer can have different thicknesses and/or densities. For example, an epidermal layer can have one or more of cornified layer (stratum corneum), clear/translucent layer (stratum lucidum), granular layer (stratum granulosum), spinous layer (stratum spinosum), basal/germinal layer (stratum basale/germinativum), or any combination thereof. In some cases, an epidermal layer comprises functional epidermal permeability barrier (e.g., organized lipid bilayers in stratum corneum). In some cases, a stratum corneum, stratum lucidum, stratum granulosum, stratum spinosum, or stratum basale/germinativum, can have a thickness of about 0.0001 mm to about 5 mm. In some cases, a stratum corneum, stratum lucidum, stratum granulosum, stratum spinosum, or stratum basale/germinativum, can have a thickness of at least about 0.001 mm, 0.01 mm, 0.02 mm, 0.04 mm, 0.08 mm, 0.1 mm, 0.15 mm, 0.2 mm, 0.4 mm, 0.8 mm, 1 mm, 2 mm, 4 mm, 8 mm, or 10 mm. In some cases, a stratum corneum, stratum lucidum, stratum granulosum, stratum spinosum, or stratum basale/germinativum, can have a thickness of at most about 50 mm, 40 mm, 20 mm, 10 mm, 8 mm, 4 mm, 2 mm, 1 mm, 0.8 mm, 0.4 mm, 0.2 mm, 0.15 mm, 0.1 mm, 0.08 mm, 0.04 mm, 0.02 mm, or 0.01 mm.

An epidermal layer can further comprise cells producing pigments, e.g., melanin. Such pigment-producing cells can be melanocytes. Melanocytes in the epidermal layer can express one or more markers. Such markers can include, but are not limited to, SRY-box containing gene 10 (Sox-10), Microphthalmia-associated transcription factor (MITF-M), premelanosome protein (gp-100), Dopachrome tautomerase (DCT), Tyrosinase (TYR), and Melan-A (MLANA).

Cells in Synthetic Leather

A synthetic leather can comprise cells in the dermal layer and epidermal layer disclosed herein. In some cases, a synthetic leather also comprises hair follicle cells, endothelial cells, dermal papilla cells, immune system cells (such as lymphocytes, dendritic cells, macrophages or Langerhans cells), adipocytes, nerve cells, and a mixture thereof.

One or more cells in a synthetic leather can be genetically engineered cells. The term "genetically engineered" can refer to a man-made alteration to the nucleic acid content of a cell. Therefore, genetically engineered cells can include cells containing an insertion, deletion, and/or substitution of one or more nucleotides in the genome of a cell as well as alterations including the introduction of self-replicating extrachromosomal nucleic acids inserted into the cell. Genetically engineered cells also include those in which transcription of one or more genes has been altered, e.g., increased or reduced.

In some cases, a synthetic leather has at least one of the components of native skin such as melanocytes, hair follicles, sweat glands and nerve endings. In certain cases, a synthetic leather can be distinguished from normal native skin by its lack of at least one of these components. In some cases displaying abnormal phenotypes or having at least one cell with an altered genotype, a synthetic leather can include all of these components.

In some case, additional components can be added to a synthetic leather. Such additional components can include myoepithelial cells, duct cells, secretory cells, alveolar cells, langerhans cells, Merkel cells, adhesions, mammary glands, or any mixture thereof. In some cases, a synthetic leather comprises one or more of: neural cells, connective tissue (including bone, cartilage, cells differentiating into bone forming cells and chondrocytes, and lymph tissues), epithelial cells (including endothelial cells that form linings in cavities and vessels or channels, exocrine secretory epithelial cells, epithelial absorptive cells, keratinizing epithelial cells, and extracellular matrix secretion cells), and undifferentiated cells (such as embryonic cells, stem cells, and other precursor cells).

A synthetic leather can comprise hair follicles. A hair follicle can comprise one or more structures, including papilla, matrix, root sheath, bulge, infundibulum, the arrector pili muscles, the sebaceous glands, and the apocrine sweat glands. A hair follicle can comprise one or more hair follicle cells, including dermal papilla cell, outer root sheath cell, or any combination thereof. In some cases, a hair follicle can be in an epidermal layers. In some cases, a hair follicle can be in a dermal layer. A hair follicles cell can be differentiated from a progenitor, e.g., a stem cell such as an iPSC. In some embodiments, at least about 1%, 2%, 3%, 4%, 5%, 6%, 7%, 8%, 9%, 10%, 20%, 30%, 40%, 50%, 60%, 70%, 80%, 90%, 100% of hair follicle cells can be differentiated from induced pluripotent stem cells.

In some embodiments, a synthetic leather can be devoid of hair, blood vessels, sebaceous glands, hair follicle, oil glands, nerve, or a combination thereof.

In some cases, a synthetic leather can comprise hairs, e.g., in one or more layered structures. For example, a synthetic leather can comprise fur. The hairs (e.g., fur) can be natural, synthetic, or a combination thereof The hairs (e.g., fur) can be grown from cells in the synthetic leather, or added to synthetic leather from an exogenous source. In other cases, a synthetic leather may not have any hairs.

Stem Cells

One or more cells in a synthetic leather can be differentiated from progenitor cells, such as stem cells. For example, fibroblasts in a synthetic leather can be differentiated from stem cells. For example, keratinocytes in a synthetic leather can be differentiated from stem cells. For example, melanocytes in a synthetic leather can be differentiated from stem cells. In some embodiments, at least about 1%, 2%, 3%, 4%, 5%, 6%, 7%, 8%, 9%, 10%, 20%, 30%, 40%, 50%, 60%, 70%, 80%, 90%, 100% of cells disclosed herein can be differentiated from stem cells. In some embodiments, at least about 1%, 2%, 3%, 4%, 5%, 6%, 7%, 8%, 9%, 10%, 20%, 30%, 40%, 50%, 60%, 70%, 80%, 90%, 100% of fibroblasts can be differentiated from induced pluripotent stem cells. In some embodiments, at least about 1%, 2%, 3%, 4%, 5%, 6%, 7%, 8%, 9%, 10%, 20%, 30%, 40%, 50%, 60%, 70%, 80%, 90%, 100% of keratinocytes can be differentiated from induced pluripotent stem cells. In some embodiments, at least about 1%, 2%, 3%, 4%, 5%, 6%, 7%, 8%, 9%, 10%, 20%, 30%, 40%, 50%, 60%, 70%, 80%, 90%, 100% of melanocytes cells can be differentiated from induced pluripotent stem cells.

Stem cells can be embryonic stem cells (ESCs), adult stem cells (i.e., somatic stem cells) or induced pluripotent stem cells (iPSCs). In some embodiments, a stem cell can be totipotent, pluripotent or multipotent for example adult stem cells and cord blood stem cells). Embryonic stem cells can be derived from fertilized embryos that are less than one week old. Induced pluripotent stem cells can be obtained through the induced expression of one or more of Oct3, Oct4, Sox2, Klf4, and c-Myc genes in any somatic cell (e.g., adult somatic cell) such as fibroblast. In some cases, one or more other genes can also be induced for reprograming a somatic cell to an induced pluripotent stem cell. Examples of such genes include NANOG, UTF1, LIN28, SALL4, NR5A2, TBX3, ESSRB, DPPA4, SV40LT, REM2, MDM2, and cyclin D1.

Various delivery methods can be used to modulate the expression of genes to reprogram a somatic cell to an iPSC. Exemplary delivery methods include naked DNA delivery, adenovirus, electrical delivery, chemical delivery, mechanical delivery, polymer based systems, microinjection, retroviruses (e.g., MMLV-derived retroviruses), and lentiviruses (e.g., excisable lentiviruses). In some cases, induced pluripotent stem cells can be obtained according to the protocol as described by Takahashi et al., Cell. 2007 Nov. 30; 131(5):861-72 (2007), or by Yu et al., Science 318, 1917-1920 (2007) (2007). In some case, somatic cells (e.g., adult somatic cells) are transfected with viral vectors, such as retroviral vectors, which comprise Oct3, Oct4, Sox2, Klf4, and c-Myc genes. In some cases, Sendai viruses are used as a delivery system, e.g., Sendai viruses produced by ID Pharma Co., Ltd., Japan.

Sources of Cells

A synthetic leather can comprise cells derived from animals of one or more species. For example, the cells in a synthetic leather can be derived from mammals, birds, reptiles, amphibian, fish, invertebrates, or any combination thereof.

A synthetic leather can comprise cells derived from mammals, e.g., mammalian cells, or non-mammals. A mammal can be a non-human mammal. A non-human mammal can be antelope, bear, beaver, bison, boar, camel, caribou, cat, cattle, deer, dog, elephant, elk, fox, giraffe, goat, hare, horse, ibex, kangaroo, lion, llama, lynx, mink, moose, oxen, peccary, pig, rabbit, rhino, seal, sheep, squirrel, tiger, whale, wolf, yak, or zebra. In some cases, a mammal can be primate, bovine, ovine, porcine, equinine, canine, feline, rodent, or lagomorph. A non-mammal can be a fish, a bird or a reptile. In some cases, a mammal can be a human. In some embodiments a human can be a celebrity. As used herein, the term "celebrity" can be defined as a person that has come into the community attention by way of notoriety or general fame of previous activities. A "celebrity" can be associated with industries including but not limited to professional and amateur sports, entertainment, music, motion picture, business, print and electronic media, politics, and the like.

A synthetic leather can comprise cells derived from other species. In some cases, the cells are derived from birds, such as chicken, duck, emu, goose, grouse, ostrich, pheasant, pigeon, quail, or turkey. In some cases, the cells are derived from reptiles such as turtle, snake, crocodile, or alligator. In some cases, the cells are derived from amphibians such as frog, toad, salamander, or newt. In some cases, the cells are derived from fish, such as anchovy, bass, catfish, carp, cod, eel, flounder, fugu, grouper, haddock, halibut, herring, mackerel, mahi-mahi, manta ray, marlin, orange roughy, perch, pike, pollock, salmon, sardine, shark, snapper, sole, stingray, swordfish, tilapia, trout, tuna, or walleye.

In some cases, all cells in a synthetic leather are derived from the same species. For example, all cells in a synthetic leather can be bovine cells. In other cases, a synthetic leather comprises cells derived from multiple species. For example, a synthetic leather can comprise bovine cells and alligator cells. In some cases, a synthetic leather comprises cells derived from at least 2, 3, 4, 5, 6, 7, 8, or 10 species.

Progenitors of the cells in a synthetic leather can also be derived from the sources described herein. For example, stem cells (e.g., iPSCs), somatic cells (e.g., to be reprogramed to iPSCs), primary cells used in synthetic cells, dermal layer cells, epidermal layer cells, or any cells in the synthetic and their progenitors thereof can be derived from the sources described herein.

Any cell can be a live cell or a dead cell. When multiple cells are present, a cells may be a live cell, may be a dead cell, or any combination thereof.

Layered Structure

A synthetic leather can comprise one or more layered structures. A layered structure can be formed by placing a first type of layer upon a second type of layer. The first type of layer and the second type of layer can be the same or different. In some cases, a layered structure can be formed by placing an epidermal layer upon a dermal layer. For example, a layered structure can be formed by placing an epidermal layer upon a dermal layer, with a basement membrane substitute in between.

A layered structure can comprise two or more layers. In some cases, a layered structure comprises at least 2, 3, 4, 5 6, 7, 8, 9, 10, 15, 20, 30, 40, 50, 60, 70, 80, 90, 100, 500, or 1000 layers. In some cases, a layered structure comprises at least 2, 3, 4, 5 6, 7, 8, 9, 10, 15, 20, 30, 40, 50, 60, 70, 80, 90, 100, 500, or 1000 first type of layers, and at least 2, 3, 4, 5 6, 7, 8, 9, 10, 15, 20, 30, 40, or 50 second type of layers. For example, a layered structure can comprise at least 2, 3, 4, 5 6, 7, 8, 9, 10, 15, 20, 30, 40, 50, 60, 70, 80, 90, 100, 500, or 1000 dermal layers, and at least 2, 3, 4, 5 6, 7, 8, 9, 10, 15, 20, 30, 40, 50, 60, 70, 80, 90, 100, 500, or 1000 layers of epidermal layers.

A layered structure can comprise one or more types of cells described herein. For example, a layered structure can comprise cells in a dermal layer, such as fibroblasts, cells in an epidermal layer, such as keratinocytes, or any combination thereof. In some cases, a layered structure further comprises cells other than fibroblasts and keratinocytes. For example, a layered structure can comprise melanocytes.

A layered structure can have a thickness from about 0.001 mm to about 100 mm. For example, a layered structure can have a thickness from about 0.005 mm to about 50 mm, from about 0.005 to about 10, from about 0.01 mm to about 10 mm, from about 0.02 to about 5 mm, from about 0.05 to about 5 mm, from about 0.1 to about 5 mm, from about 0.1 to about 2 mm, from about 0.1 to about 1 mm, or from about 0.1 to about 0.5 mm. In some cases, the thickness of a layered structure can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, 10 mm, 20 mm, 40 mm, 60 mm, 80 mm, or 100 mm. In some cases, the thickness of a layered structure can be at most 100 mm, 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a layered structure can have a thickness of at least about 100, 200, 300, 400, 500, 600, 700, 800 mm.

The length of a layered structure can be engineered to fit the function or use of a synthetic leather. A layered structure can have a length from about 0.01 mm to about 50 m. For example, a layered structure can have a length from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a layered structure can have a length from about 0.02 mm to 5 mm. For example, a layered structure can have a length from about 0.1 mm to 0.5 mm. For example, a layered structure can have a length from 0.2 mm to 0.5 mm. In some cases, the length of a layered structure can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the length of a layered structure can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a layered structure can have a length of at least about 50, 60, 70, 80, 90, 100, 200, 300, 400, 500, 700, 1000 mm. In some embodiments, a layered structure can have a length of at least about 50, 60, 70, 80, 90, 100, 200, 300, 400, 500, 600, 700 cm. In some embodiments, a layered structure can have a length of at least about 50, 60, 70, 80, 90, 100, 200, 300, 400 m.

The width of a layered structure can be engineered to fit the function or use of a synthetic leather. A layered structure can have a width from about 0.01 mm to about 50 m. For example, a layered structure can have a width from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a layered structure can have a width from about 0.02 mm to 5 mm. For example, a layered structure can have a width from about 0.1 mm to 0.5 mm. For example, a layered structure can have a width from about 0.2 mm to 0.5 mm. In some cases, the width of a layered structure can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the width of a layered structure can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a layered structure can have a width of at least about 50, 60, 70, 80, 90, 100, 200, 300, 400, 500, 700, 1000 mm. In some embodiments, a layered structure can have a width of at least about 50, 60, 70, 80, 90, 100, 200, 300, 400, 500, 600, 700 cm. In some embodiments, a layered structure can have a width of at least about 50, 60, 70, 80, 90, 100, 200, 300, 400 m.

A layered structure can comprise fibroblasts and keratinocytes at any ratio of at least about 50:1, 40:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:10, or 1:100. In some cases, the ratio of fibroblasts to keratinocytes can be from about 20:1 to about 3:1, from about 20:1 to about 4:1, from about 20:1 to about 5:1, from about 20:1 to about 10:1, or from about 20:1 to about 15:1.

A layered structure can comprise fibroblasts and melanocytes at any ratio of at least about 50:1, 40:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:10, or 1:100. In some cases, the ratio of fibroblasts to melanocyte can be from about 20:1 to about 3:1, from about 20:1 to about 4:1, from about 20:1 to about 5:1, from about 20:1 to about 10:1, or from about 20:1 to about 15:1.

A layered structure can comprise keratinocytes and melanocytes at any ratio of at least about 50:1, 40:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:10, or 1:100. In some cases, the ratio of keratinocytes to melanocyte can be from about 20:1 to about 3:1, from about 20:1 to about 4:1, from about 20:1 to about 5:1, from about 20:1 to about 10:1, or from about 20:1 to about 15:1.

One type of cells in a layered structure can comprise at most 99%, 95%, 90%, 85%, 80%, 75%, 70%, 65%, 60%, 55%, 50%, 45%, 40%, 35%, 30%, 25%, 20%, 10%, 5%, or 1% of the total cell population in the layered structure. One type of cells in a layered structure can comprise about at least 1%, 5%, 10%, 20%, 30%, 40%, 50%, 60%, 65%, 70%, 75%, 80%, 85%, 90%, or 95% of the total cell population in the layered structure. For example, fibroblasts in a layered structure can comprise about at least 5%, 10%, 20%, 30%, 40%, 50%, 60%, 65%, 70%, 75%, 80%, 85%, 90%, or 95% of the total cell population in the layered structure.

Synthetic Leather

A synthetic leather can be formed by one or more layered structures. For example, a synthetic leather can be formed by at least 1, 2, 3, 4, 5, 6, 7, 8, 9, 10, 15, 20, 30, 40, 50, 60, 70, 80, 90, or 100 layered structures.

A synthetic leather can be of various thickness. For example, a synthetic leather can have a thickness resembling to a natural leather. In some cases, a synthetic leather can have a thickness from about 0.001 mm to about 100 mm. For example, a layered structure can have a thickness from about 0.005 mm to about 50 mm, from about 0.005 to about 10, from about 0.01 mm to about 10 mm, from about 0.1 to about 5 mm, from about 0.5 mm to about 5 mm, from about 0.5 mm to about 3 mm, from about 0.8 mm to about 3 mm, from about 0.8 mm to about 2 mm, from about 0.8 mm to about 1.8 mm, from about 0.8 mm to about 1.6 mm, from about 0.9 mm to about 1.4 mm, from about 1 mm to about 1.5 mm, from about 1 mm to about 1.4 mm, or from about 1 mm to about 1.3 mm. In some cases, the thickness of a synthetic leather can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, 10 mm, 20 mm, 40 mm, 60 mm, 80 mm, or 100 mm. In some cases, the thickness of a synthetic leather can be at most 100 mm, 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some cases, the thickness of a synthetic leather can be about 1.2 mm.

A synthetic leather can have a length from about 0.01 mm to about 50 m. For example, a synthetic leather can have a length from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a synthetic leather can have a length from about 0.02 mm to 5 mm. For example, a synthetic leather can have a length from about 0.1 mm to 0.5 mm. For example, a synthetic leather can have a length from about 0.2 mm to 0.5 mm. In some cases, the length of a synthetic leather can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the length of a synthetic leather can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a synthetic leather can have a length of at least about 50, 60, 70, 80, 90, 100, 200, 300, 400, 500, 700, 1000 mm. In some embodiments, a synthetic leather can have a length of at least about 50, 60, 70, 80, 90, 100, 200, 300, 400, 500, 600, 700 cm. In some embodiments, a synthetic leather can have a length of at least about 50, 60, 70, 80, 90, 100, 200, 300, 400 m.

A synthetic leather can have a width from about 0.01 mm to about 50 m. For example, a synthetic leather can have a width from about 0.01 mm to about 10 mm, from about 0.01 mm to about 8 mm, from about 0.01 to about 5 mm, from about 0.02 to about 5 mm, from about 0.05 to about 5 mm, from about 0.1 to about 5 mm, from about 0.1 to about 2 mm, from about 0.1 to about 1 mm, from about 0.1 to about 0.8 mm, or from about 0.1 to about 0.5 mm. For example, a synthetic leather can have a width from about 0.02 mm to 5 mm. For example, a synthetic leather can have a width from about 0.1 mm to 0.5 mm. For example, a synthetic leather can have a width from about 0.2 mm to 0.5 mm. In some cases, the width of a synthetic leather can be at least 0.001 mm, 0.01 mm, 0.02 mm, 0.04 mm, 0.08 mm, 0.1 mm, 0.2 mm, 0.4 mm, 0.8 mm, 1 mm, 2 mm, 4 mm, 8 mm, or 10 mm. In some cases, the width of a synthetic leather can be at most 50 mm, 40 mm, 20 mm, 10 mm, 8 mm, 4 mm, 2 mm, 1 mm, 0.8 mm, 0.4 mm, 0.2 mm, 0.1 mm, 0.08 mm, 0.04 mm, 0.02 mm, or 0.01 mm. In some embodiments, a synthetic leather can have a width of at least about 50, 60, 70, 80, 90, 100, 200, 300, 400, 500, 700, 1000 mm. In some embodiments, a synthetic leather can have a width of at least about 50, 60, 70, 80, 90, 100, 200, 300, 400, 500, 600, 700 cm. In some embodiments, a synthetic leather can have a width of at least about 50, 60, 70, 80, 90, 100, 200, 300, 400 m.

Basement Membrane Substitute

A synthetic leather can further comprise a basement membrane substitute. A basement membrane substitute can be between two cell layers, e.g., between a dermal layer and an epidermal layer. A basement membrane substitute can be a dermo-epidermal junction similar to that which exists in vivo, from a structural point of view and/or from a biochemical point of view. From the biochemical point of view, a basement membrane substitute can comprise components of the basal membrane, of the lamina densa, of the lamina lucida and of the sub-basal zone, such as, collagen IV, collagen VII, laminin 5, entactin fibronectin, or any combination thereof.

A basement membrane substitute in a synthetic leather can be urinary basement membrane (UBM), liver basement membrane (LBM), amnion, chorion, allograft pericardium, allograft acellular dermis, amniotic membrane, Wharton's jelly, or any combination thereof. For example, a basement membrane substitute can be a dried acellular amniotic membrane. In certain cases, a basement membrane substitute can be a polymer, e.g., a nanopolymer. For example, a basement membrane substitute can be nano-fibrous poly hydroxybutyrate-cohydroxyvalerate (PHBV), as described by Bye et al., Journal of Biomaterials and Tissue Engineering Vol. 4, 1-7, 2014.

Scaffold

A cell layer (e.g., a dermal layer), a layered structure, or a synthetic leather can be placed on a scaffold. A scaffold can provide certain firmness (e.g., resistance to tearing), elasticity, or both. In some cases, a part of or the entire scaffold can be comprise in the synthetic leather. In other cases, a scaffold may not comprised in the synthetic leather. After assisting the formation of a layer in a synthetic leather, a scaffold can be removed from the final synthetic leather product. In certain cases, a scaffold comprised in a synthetic leather can be degraded after a period of time. A scaffold described herein can comprise a trabecular pattern.

A scaffold can be made of natural materials, synthetic materials, or combination thereof. Examples of scaffolds include a scaffold formed using a net made of a bioabsorbable synthetic polymer, a scaffold formed by attaching a nylon net to a silicon film, a scaffold having a two-layered structure of a collagen sponge and a silicon sheet, a scaffold formed using an atelo collagen sponge made into a sheet, a scaffold formed by matching collagen sponges having different pore sizes, and acellular dermal matrices (ADM) formed using fibrin glue or allogeneic skin that has been made cell-free.

A scaffold can comprise natural substances such as collagen (e.g., collagen matrix), natural adhesive (e.g., fibrin glue, cold glues, animal glue, blood albumen glue, casein glue, or vegetable glues such as starch and dextrin glues). In some cases, a scaffold comprises silk. For example, a scaffold can be made of silk. In some embodiments, a scaffold can comprise, silk fibroin, cellulose, cotton, acetate, acrylic, latex fibers, linen, nylon, rayon, velvet, modacrylic, olefin polyester, saran, vinyon, wool, jute, hemp, bamboo, flax or a combination thereof. In some embodiments, a scaffold can comprise fibers. In some embodiments, the fibers can be fibers of silk, cotton, wool, linen, cellulose extracted in particular from wood, vegetables or algae, polyamide, modified cellulose (rayon, viscose, acetate, especially rayon acetate), poly-p-phenyleneterephthalamide, acrylic fibers, for example those of polymethyl methacrylate or of poly-2-hydroxyethyl methacrylate, fibers of polyolefin for example fibers of polyethylene or polypropylene, glass, silica, aramid, carbon, for example in the form of graphite, poly(tetrafluoroethylene), insoluble collagen, polyesters, polyvinyl chloride or polyvinylidene chloride, polyvinyl alcohol, polyacrylonitrile, chitosan, polyurethane, poly(urethane-urea) or polyethylene phthalate, and fibers formed from a blend of polymers such as those mentioned above, such as polyamide/polyester fibers or any combination thereof.

A scaffold can comprise polymers. A polymer can be a biopolymer. A biopolymer can include but is not limited to chitin, chitosan, elastin, collagen, keratin or polyhydroxyalkanoate. The polymers can be biodegradable, biostable, or combinations thereof. The polymer in a scaffold can be natural polymers. Exemplary natural polymers include polysaccharides such as alginate, cellulose, dextran, pullane, polyhyaluronic acid, chitin, poly(3-hydroxyalkanoate), poly (3-hydroxyoctanoate) or poly(3-hydroxyfatty acid). In some cases, a scaffold also comprises chemical derivatives of the natural polymers. Such chemical derivatives can include substitutions and/or additions of chemical groups such as alkyl, alkylene, hydroxylations, oxidations, as well as other modifications familiar to those skilled in the art. The natural polymers can also be selected from proteins such as collagen, zein, casein, gelatin, gluten, and serum albumen. The polymer in a scaffold can be biodegradable synthetic polymers, including poly alpha-hydroxy acids such as poly L-lactic acid (PLA), polyglycolic acid (PGA) or copolymers thereof (e.g., poly D,L-lactic co-glycolic acid (PLGA)), and hyaluronic acid.

A scaffold can be bioabsorbable. A bioabsorbable scaffold can be a non-cytotoxic structure or substance that can be capable of containing or supporting living cells and holding them in a desired configuration for a period of time. The term "bioabsorbable" can refer to any material the body can break down into non-toxic by-products that are excreted from the body or metabolized therein. Exemplary bioabsorbable materials for a scaffold include, poly(lactic acid), poly(glycolic acid), poly(trimethylene carbonate), poly(dimethyltrimethylene carbonate), poly(amino acids)s, tyrosine-derived poly(carbonates)s, poly(carbonates)s, poly (caprolactone), poly(para-dioxanone), poly(esters)s, poly (ester-amides)s, poly(anhydrides)s, poly(ortho esters)s, collagen, gelatin, serum albumin, proteins, polysaccharides, mucopolysaccharides, carbohydrates, glycosaminoglycans, poly(ethylene glycols)s, poly(propylene glycols)s, poly (acrylate esters)s, poly(methacrylate esters)s, poly(vinyl alcohol), hyaluronic acid, chondroitin sulfate, heparin, dermatan sulfate, versican, copolymers, blends and mixtures of polymers, and oligomers containing bioabsorbable linkages.

A scaffold can be of various thicknesses. For example, a scaffold can have a thickness that can be suitable for forming a cell layer. For example, a scaffold can have a thickness from about 0.1 mm to about 10 mm, such as from about 0.1 mm to about 5 mm, from about 0.1 mm to about 4 mm, from about 0.1 mm to about 3 mm, from about 0.1 mm to about 2 mm, to about 0.1 mm to about 1 mm, from about 0.2 mm to about 1 mm, from about 0.3 mm to about 1 mm, from about 0.4 mm to about 1 mm, from about 0.5 mm to about 1 mm, from 0.3 mm to about 1.5 mm, from about 0.4 mm to about 1.2 mm, from about 0.6 mm to about 1.2 mm, or from about 0.7 mm to about 1.5 mm. For example, a scaffold can have a thickness from about 0.5 mm to 1 mm. In some cases, a scaffold can be at least 0.1 mm, 0.2 mm, 0.3 mm, 0.4 mm, 0.5 mm, 0.8 mm, 1 mm, 2 mm, 3 mm, 4 mm, or 5 mm thick. In some cases, a scaffold can be at most 0.5 mm, 0.8 mm, 1 mm, 2 mm, 3 mm, 4 mm, 5 mm, 6 mm, 7 mm, 8 mm, 9 mm, or 10 mm thick. In some embodiments, a scaffold can have a length and/or a width of a cell layer to be placed and/or grown upon a scaffold. In some embodiments, a scaffold can have a length and/or a width of a cell layer described herein.

A scaffold can have a surface area on a face of a synthetic leather. For example, a scaffold can have a surface area of from about 0.1 $mm^2$ to about 100 $mm^2$, from about 0.1 $mm^2$ to about 95 $mm^2$, from about 0.1 $mm^2$ to about 90 $mm^2$, from about 0.1 $mm^2$ to about 85 $mm^2$, from about 0.1 $mm^2$ to about 80 $mm^2$, from about 0.1 $mm^2$ to about 75 $mm^2$, from about 0.1 $mm^2$ to about 70 $mm^2$, from about 0.1 $mm^2$ to about 65 $mm^2$, from about 0.1 $mm^2$ to about 60 $mm^2$, from about 0.1 $mm^2$ to about 55 $mm^2$, from about 0.1 $mm^2$ to about 50 $mm^2$, from about 0.1 $mm^2$ to about 45 $mm^2$, from about 0.1 $mm^2$ to about 40 $mm^2$, from about 0.1 $mm^2$ to about 35 $mm^2$, from about 0.1 $mm^2$ to about 30 $mm^2$, from about 0.1 $mm^2$ to about 25 $mm^2$, from about 0.1 $mm^2$ to about 20 $mm^2$, from about 0.1 $mm^2$ to about 15 $mm^2$, from about 0.1 $mm^2$ to about 10 $mm^2$, from about 0.1 $mm^2$ to about 5 $mm^2$, or from about 0.1 $mm^2$ to about 1 $mm^2$. In some cases, a scaffold can have a surface area of from about 0.1 $cm^2$ to about 100 $cm^2$, from about 0.1 $cm^2$ to about 95 $cm^2$, from about 0.1 $cm^2$ to about 90 $cm^2$, from about 0.1 $cm^2$ to about 85 $cm^2$, from about 0.1 $cm^2$ to about 80 $cm^2$, from about 0.1 $cm^2$ to about 75 $cm^2$, from about 0.1 $cm^2$ to about 70 $cm^2$, from about 0.1 $cm^2$ to about 65 $cm^2$, from about 0.1 $cm^2$ to about 60 $cm^2$, from about 0.1 $cm^2$ to about 55 $cm^2$, from about 0.1 $cm^2$ to about 50 $cm^2$, from about 0.1 $cm^2$ to about 45 $cm^2$, from about 0.1 $cm^2$ to about 40 $cm^2$, from about 0.1 $cm^2$ to about 35 $cm^2$, from about 0.1 $cm^2$ to about 30 $cm^2$, from about 0.1 $cm^2$ to about 25 $cm^2$, from about 0.1 $cm^2$ to about 20 $cm^2$, from about 0.1 $cm^2$ to about 15 $cm^2$, from about 0.1 $cm^2$ to about 10 $cm^2$, from about 0.1 $cm^2$ to about 5 $cm^2$, or from about 0.1 $cm^2$ to about 1 $cm^2$. In some cases, a scaffold can have a surface area of from about 0.1 $m^2$ to about 100 $m^2$, from about 0.1 $m^2$ to about 95 $m^2$, from about 0.1 $m^2$ to about 90 $m^2$, from about 0.1 $m^2$ to about 85 $m^2$, from about 0.1 $m^2$ to about 80 $m^2$, from about 0.1 m² to about 75 m², from about 0.1 m² to about 70 m², from about 0.1 m² to about 65 m², from about 0.1 m² to about 60 m², from about 0.1 m² to about 55 m², from about 0.1 m² to about 50 m², from about 0.1 m² to about 45 m², from about 0.1 m² to about 40 m², from about 0.1 m² to about 35 m², from about 0.1 m² to about 30 m², from about 0.1 m² to about 25 m², from about 0.1 m² to about 20 m², from about 0.1 m² to about 15 m², from about 0.1 m² to about 10 m², from about 0.1 m² to about 5 m², or from about 0.1 m² to about 1 m².

In some cases, a scaffold can have a surface area of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, or 100 mm². In some cases, a scaffold can have a surface area of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, or 100 cm². In some cases, a scaffold can have a surface area of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, or 100 m².

Alternatively, a cell layer may not form on a scaffold. For example, a dermal layer may not form on a scaffold (e.g., collagen matrix). In certain cases, a synthetic leather does not comprise a scaffold.

Pigments

A synthetic leather can comprise one or more pigments. One or more layer structures of the synthetic leather can be pigmented. A pigment in a synthetic leather can be a natural pigment produced in cells forming the synthetic leather. For example, a pigment can be melanin, including eumelanin (e.g., brown eumelanin and black eumelanin), pheomelanin, neuromelanin, or any combination thereof. A pigment in a synthetic leather can be an exogenous pigment, such as a leather pigment dye.

Collagen

A synthetic leather can comprise collagen. Collagen can refer to any member of a family of at least 28 distinct collagen types. Collagens can be characterized by a repeating triplet of amino acids, -(Gly-X-Y)n-, so that approximately one-third of the amino acid residues are in collagen are glycine. X can be proline and Y can be hydroxyproline. Thus, the structure of collagen can have twined triple units of peptide chains of differing lengths. A synthetic leather can comprise collagen from one or more species. In some cases, a synthetic leather comprises collagen from different animals. Different animals can produce different amino acid compositions of the collagen, which can result in different properties (and differences in the resulting leather). Collagen fiber monomers can be produced from alpha-chains of about 1050 amino acids long, so that the triple helix takes the form of a rod of about 300 nm long, with a diameter of about 1.5 nm.

A synthetic leather can comprise one or more types of collagen. Collagen comprised in a synthetic leather can include fibrillary collagens, non-fibrillar collagens, or a combination thereof. Fibrillary collagens include type I, type II, type III, type V, and type XI collagens. Non-fibrillar collagens include fibril associated collagens with interrupted triple helices (e.g., type IX, type XII, type XIV, type XVI, and type XIX), short chain collagens (e.g., type VIII and type X), basement membrane collagens (type IV), Multiplexin (Multiple Triple Helix domains with Interruptions) (e.g., Type XV and type XVIII), MACIT collagens (Membrane Associated Collagens with Interrupted Triple Helices) (e.g., Type XIII and type XVII).

Collagen can be comprised in one or more parts of a synthetic leather. For example, collagens can be comprised in one or more dermal layers, one or more epidermal layers, or combination thereof, in a synthetic leather. For example, collagens can be comprised in one or more layered structures in a synthetic leather. In some cases, when part of the synthetic leather can be removed during process, collagen can also be comprised in the removed product.

Collagen in a synthetic leather can be from one or more sources. For example, the collagen can be produced by collagen producing cells in the synthetic leather. For example, the collagen can be separately added to the leather. In some cases, a synthetic leather comprises collagen produced by collagen producing cells and collagens separately added.

At least part of the collagen in a synthetic leather can be produced by collagen producing cells. Such collagen producing cells can be comprised in the synthetic leather. Exemplary collagen producing cells include epithelial cells, fibroblasts, keratinocytes, corneocytes, melanocytes, Langerhans cells, basal cells, smooth muscle cells, or a combination thereof. The epithelial cells can include squamous cells, cuboidal cells, columnar cells, basal cells, or a combination thereof. The fibroblasts can include dermal fibroblasts. The keratinocytes can include epithelial keratinocytes, basal keratinocytes, proliferating basal keratinocytes, differentiated suprabasal keratinocytes, or a combination thereof. Collagen in a synthetic leather can be produced by one or more types of collagen-producing cells.

Additives

A synthetic leather can further comprise one or more additives. Such additives can enhance the commercial appeal (e.g., appearance, color, or odor). Exemplary additives include minerals, fiber, fatty acids, and amino acids, proteins. An additive can be an odorant.

Additives can include one or more of: matrix proteins, proteoglycans, antioxidants, perfluorocarbons, and growth factors. A growth factor can be a protein, a polypeptide, or a complex of polypeptides, including cytokines (e.g., that are produced by a cell and which can affect itself and/or a variety of other neighboring or distant cells). Growth factors can affect the growth and/or differentiation of specific types of cells, either developmentally or in response to a multitude of physiological or environmental stimuli. Some, but not all, growth factors are hormones. Exemplary growth factors include insulin, insulin-like growth factor (IGF), nerve growth factor (NGF), vascular endothelial growth factor (VEGF), keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGF-a), transforming growth factor beta (TGF-β), including TGFpi and TGFP3, epidermal growth factor (EGF), granulocyte-macrophage colony-stimulating factor (GM-CSF), granulocyte colony-stimulating factor (G-CSF), interleukin-6 (IL-6), IL-8, and the like. Other polypeptides or molecules (e.g., healing agents; enzymes such as matrix-degrading enzymes and matrix-degrading enzyme inhibitors (e.g., TIMPs), antibiotics, and antimycotics) can also be added to a synthetic leather.

Additives can also include preservatives known to the art. Exemplary preservatives include antimicrobial preservatives such as calcium propionate, sodium nitrate, sodium nitrite, sulfites (e.g., sulfur dioxide, sodium bisulfate, potassium hydrogen sulfite, etc.), disodium ethylenediammetetraacetic acid (EDTA), antioxidant such as butylated hydroxyanisole (BHA) and butylated hydroxytoluene (BHT).

In certain cases, a synthetic leather can comprise an extracellular matrix or connective tissue. For example, a synthetic leather can further comprise collagen, keratin, elastin, gelatin, proteoglycan, dermatan sulfate proteoglycan, glycosoaminoglycan, fibronectin, laminin, dermatopontin, lipid, fatty acid, carbohydrate, and a combination thereof.

Pattern of Synthetic Leather

A synthetic leather can be patterned. For example, the synthetic leather may be patterned after a skin pattern of an animal selected from antelope, bear, beaver, bison, boar, camel, caribou, cat, cattle, deer, dog, elephant, elk, fox, giraffe, goat, hare, horse, ibex, kangaroo, lion, llama, lynx, mink, moose, oxen, peccary, pig, rabbit, seal, sheep, squirrel, tiger, whale, wolf, yak, zebra, turtle, snake, crocodile, alligator, dinosaur, frog, toad, salamander, newt, chicken, duck, emu, goose, grouse, ostrich, pheasant, pigeon, quail, turkey, anchovy, bass, catfish, carp, cod, eel, flounder, fugu, grouper, haddock, halibut, herring, mackerel, mahi mahi, manta ray, marlin, orange roughy, perch, pike, pollock, salmon, sardine, shark, snapper, sole, stingray, swordfish, tilapia, trout, tuna, walleye, and a combination thereof. The pattern can be a skin pattern of a fantasy animal selected from dragon, unicorn, griffin, siren, phoenix, sphinx, Cyclops, satyr, Medusa, Pegasus, Cerberus, Typhoeus, gorgon, Charybdis, empusa, chimera, Minotaur, Cetus, hydra, centaur, fairy, mermaid, Loch Ness monster, Sasquatch, thunderbird, yeti, chupacabra, and a combination thereof.

A synthetic leather can be made to resemble traditional animal skin, hide, or leather products and design parameters (e.g., cell types, additives, size, shape). In some cases, a synthetic leather comprises a cell layer characterized by a composition that can be substantially similar to traditional animal skin, hide, or leather products. For example, such layer can be characterized by a composition that can be substantially about 60% to 80% aqueous fluid, about 14%-35% protein, about 1%-25% fat. In some cases, keratinocytes of the cell layer are aligned. For example, the keratinocytes can be aligned by application of an electrical field. For example, keratinocytes can be aligned by application of a mechanical stimulus, such as cyclical stretching and relaxing the substratum. In some cases, aligned (e.g., electro-oriented and mechano-oriented) keratinocytes have substantially the same orientation with regard to each other as can be found in many animal skin tissues.

Leather Articles

A synthetic leather herein can be at least a portion of a leather article. For example, a synthetic leather can be used as substitute of natural leather in a leather article. Exemplary leather articles include a watch strap, belt, suspender, packaging, shoe, boot, footwear, glove, clothing (e.g., tops, bottoms, and outerwear), luggage, bag (e.g., a handbag with or without shoulder strap), clutch, purse, coin purse, billfold, key pouch, credit card case, pen case, backpack, cases, wallet, saddle, harness, whip, travel goods (e.g., a trunk, suitcase, travel bag, beauty case, or a toilet kit), rucksacks, portfolio, document bag, briefcase, attache case, pet article (e.g., a leash or collar), hunting and fishing article (e.g., a gun case, cutlery case, or a holster for firm arms), a stationary article (e.g., a writing pad, book cover, camera case, spectacle case, cigarette case, cigar case, jewel case, or a mobile phone holster), a sport article (e.g., a ball such as basketball, soccer ball, or a football), a building interior, a building exterior, an upholstery, a book binding, a furniture, a lamp, a lamp shade, a table covering, a wall covering, a floor covering, a ceiling covering, a car interior, a car exterior, a boat interior, a boat exterior, an airplane interior, a yacht interior, a yacht exterior, a pillow case, a sheet, a duvet cover, jewelry, an accessory, a pair of glasses, a pair of sun glasses, or a consumer electronic. For example, a leather article can be a watch wrap. For example, a leather article can be a belt. For example, a leather article can be a bag.

Skin Graft

A synthetic leather or portions thereof can also be used as a skin graft, e.g., an allograft or xenograft for transplanting to a subject. For example, the synthetic leather, dermal layer, epidermal layer and/or a layered structure can be a source of skin graft for allotransplant or xenotransplant. In some cases, the synthetic leather, dermal layer, epidermal layer and/or a layered structure can be produced with cells genetically modified to reduce immune-rejection in the recipient of the graft.

Methods

Also disclosed herein are methods of making a synthetic leather. The methods can comprise forming an artificial dermal layer, forming an artificial epidermal layer, or a combination thereof. The methods can further comprise tanning at least of a portion of the artificial dermal layer and/or artificial epidermal layer. The cells in a synthetic leather, e.g., those in the dermal layer and/or the epidermal layer can be differentiated from stem cells (e.g., iPSCs). The methods herein can further comprise differentiating stem cells (e.g., iPSCs) into cells in the synthetic leather, e.g., cells in the dermal layer and/or the epidermal layer. In certain cases, the methods comprise placing a first cell layer (e.g., an epidermal layer) upon a second cell layer (e.g., a dermal layer) thereby forming a layered structure, and tanning at least a portion of the layered structure. In some cases, the methods can further comprise removing at least a portion of the first cell layer (e.g., an epidermal layer).

Forming Cell Layers

A cell layer can be formed by preparing a plurality of multicellular bodies comprising one or more type of cells, and arranging such multicellular bodies to form a cell layer. For example, a cell layer can be formed by adjacently arranging a plurality of multicellular bodies, wherein the multicellular bodies are fused to form a planar layer.

Forming a cell layer may need a scaffold. A cell layer can be formed by arranging a plurality of multicellular bodies on a scaffold. For example, the forming step can comprise arranging or placing multicellular bodies on a support substrate that allows the multicellular bodies to fuse to form a layer (e.g., a substantially planar layer). In some cases, the multicellular bodies or the layers are arranged horizontally and/or vertically adjacent to one another. Alternatively, forming a cell layer may not need a scaffold.

Cell layers can be formed by embedding cells in a medium or gel. In some cases, dermal layers can be formed using fibroblasts embedded in a collagen I or fibrin gel. Other types of media can also be used. For example, a medium can promote fibroblast to secret sufficient amount of extracellular matrix to enable extended maintenance of epidermis without the need for collagen gels.

Forming Multicellular Bodies

There are various ways to make multicellular bodies having the characteristics described herein. In some cases, a multicellular body can be fabricated from a cell paste containing a plurality of cells, e.g., with a desired cell density and viscosity. In further cases, the cell paste can be shaped into a desired shape and a multicellular body formed through maturation (e.g., incubation). In some cases, an elongate multicellular body can be produced by shaping a cell paste including a plurality of cells into an elongate shape (e.g., a cylinder). In further cases, the cell paste can be incubated in a controlled environment to allow the cells to adhere and/or cohere to one another to form the elongate multicellular body. For example, a multicellular body can be produced by shaping a cell paste including a plurality of living cells in a device that holds the cell paste in a three-dimensional shape. In some cases, the cell paste can be incubated in a controlled environment while it can be held in the three dimensional shape for a sufficient time to produce a body that has sufficient cohesion to support itself on a flat surface, as described herein.

A cell paste can be provided by: (A) mixing cells or cell aggregates (of one or more cell types) and a cell culture medium (e.g., in a pre-determined ratio) to result in a cell suspension, and (B) compacting the cellular suspension to produce a cell paste with a desired cell density and viscosity. Compacting can be achieved by a number of methods, such as by concentrating a particular cell suspension that resulted from cell culture to achieve the desired cell concentration (density), viscosity, and consistency required for the cell paste. In some cases, a relatively dilute cell suspension from cell culture can be centrifuged for a determined time to achieve a cell concentration in the pellet that allows shaping in a mold. Tangential flow filtration ("TFF") is another suitable method of concentrating or compacting the cells. In some cases, compounds are combined with the cell suspension to lend the extrusion properties required. Suitable compounds include, collagen, hydrogels, Matrigel, nanofibers, self-assembling nanofibers, gelatin, and fibrinogen. One or more ECM components (or derivatives of ECM components) can also be included by, resuspending the cell pellet in one or more physiologically acceptable buffers containing the ECM components (or derivatives of ECM components) and the resulting cell suspension centrifuged again to form the cell paste.

Various methods can be used to shape the cell paste. For example, in a particular embodiment, the cell paste can be manually molded or pressed (e.g., after concentration/compaction) to achieve a desired shape. By way of a further example, the cell paste can be taken up (e.g., aspirated) into a preformed instrument, such as a micropipette (e.g., a capillary pipette), that shapes the cell paste to conform to an interior surface of the instrument. The cross sectional shape of the micropipette (e.g., capillary pipette) can be alternatively circular, square, rectangular, triangular, or other non-circular cross-sectional shape. In some embodiments, the cell paste can be shaped by depositing it into a preformed mold, such as a plastic mold, metal mold, or a gel mold. In some embodiments, centrifugal casting or continuous casting can be used to shape the cell paste.

The cell paste can be further matured. In some cases, the cell paste can be incubated at about 37° C. for a time period (which can be cell-type dependent) to foster adherence and/or coherence. Alternatively or in addition, the cell paste can be held in the presence of cell culture medium containing factors and/or ions to foster adherence and/or coherence.

Arranging Multicellular Bodies on a Support Substrate to Form Layers

Multicellular bodies can be arranged on a support substrate to produce a desired three-dimensional structure (e.g., a substantially planar layer). For example, multicellular bodies can be manually placed in contact with one another, deposited in place by extrusion from a pipette, nozzle, or needle, or positioned in contact by an automated machine such as a biofabricator.

A support substrate can be permeable to fluids, gasses, and nutrients and allows cell culture media to contact all surfaces of the multicellular bodies and/or layers during arrangement and subsequent fusion. In some cases, a support substrate can be made from natural biomaterials such as collagen, fibronectin, laminin, and other extracellular matrices. In some cases, a support substrate can be made from synthetic biomaterials such as hydroxyapatite, alginate, agarose, polyglycolic acid, polylactic acid, and their copolymers. In some cases, a support substrate can be solid, semisolid, or a combination of solid and semisolid support elements. In some cases, a support substrate can be planar to facilitate production of planar layers. In some cases, a support substrate can be raised or elevated above a non-permeable surface, such as a portion of a cell culture environment (e.g., a Petri dish, a cell culture flask, etc.) or a bioreactor. A permeable, elevated support substrate can contribute to prevention of premature cell death, contributes to enhancement of cell growth, and facilitates fusion of multicellular bodies to form layers.

Once assembly of a layer is complete, a tissue culture medium can be poured over the top of the construct. In some cases, the tissue culture medium enters the spaces between the multicellular bodies to support the cells in the multicellular bodies. The multicellular bodies in the three-dimensional construct can be allowed to fuse to one another to produce a layer (e.g., a substantially planar) for use in formation of the synthetic leather. The terms "fuse," "fused" or "fusion," can mean that the cells of contiguous multicellular bodies become adhered and/or cohered to one another, either directly through interactions between cell surface proteins, or indirectly through interactions of the cells with ECM components or derivatives of ECM components. A fused layer can be completely fused and that multicellular bodies have become substantially contiguous. Alternatively, a fused layer can be substantially fused or partially fused and the cells of the multicellular bodies have become adhered and/or cohered to the extent necessary to allow moving and manipulating the layer intact.

Multicellular bodies can fuse to form a layer in a cell culture environment (e.g., a Petri dish, cell culture flask, or bioreactor). In some cases, the multicellular bodies fuse to form a layer in an environment with conditions suitable to facilitate growth of the cell types included in the multicellular bodies. In some cases, fusing takes place over about 15, 20, 25, 30, 35, 40, 45, 50, 55, and 60 minutes, and increments therein. In other cases, fusing takes place over about 1, 2, 3, 4, 5, 6, 7, 8, 9, 10, 11, 12, 14, 16, 18, 20, 22, 24, 26, 28, 30, 32, 34, 36, 38, 40, 42, 44, 46, and 48 hours, and increments therein. In yet other cases, fusing takes place over about 1, 2, 3, 4, 5, 6, 7, 8, 9, 10, 12, and 14 days, and increments therein. In further cases, fusing takes place over about 2 hours to about 24 hours. Factors relevant to the fusing time can include cell types, cell type ratios, culture conditions, and the presence of additives such as growth factors.

Once fusion of a layer is complete, the layer and the support substrate can be separated. In other cases, the layer and the support substrate are separated when fusion of a layer is substantially complete or partially complete, but the cells of the layer are adhered and/or cohered to one another to the extent necessary to allow moving, manipulating, and stacking the layer without breaking it apart. The layer and the support substrate can be separated via standard procedures for melting, dissolving, or degrading the support substrate. In some cases, the support substrate can be dissolved, for example, by temperature change, light, or other stimuli that do not adversely affect the layer. In certain cases, the support substrate can be made of a flexible material and peeled away from the layer. The separated layer can be transferred to a bioreactor for further maturation. In some cases, the separated layer matures and further fuses after incorporation into an engineered animal skin, hide, or leather product.

Alternatively, the layer and the support substrate may not be separated. The support substrate degrades or biodegrades prior to packaging, freezing, sale or consumption of the assembled engineered animal skin, hide, or leather product.

A cell layer can be formed over a period of time. In some cases, a cell layer, e.g., an epidermal layer or a dermal layer, can be formed within 1, 2, 3, 4, 5, 6, 7, 8, 9, 10, 11, 12, 13, 14, 15, 16, 17, 18, 19, 20, 25, 30, 40, 50, 60, 120, 300 days. In some cases, a dermal layer can be formed in about 1 to 15 days, e.g., 5 to 10 days, or 10 to 12 days. In some cases, a dermal layer can be formed about 5 to 25 days, e.g., 14 to 15 days.

The present disclosure provides methods for making synthetic leather improved barrier function. In some cases, the methods comprise providing keratinocytes and a culture media comprising ascorbic acid and linoleic acid; and culturing the keratinocytes under conditions such that a synthetic leather having improved barrier function can be formed. In some cases, the culture conditions include culture at about 50 to 95% humidity, e.g., about 75% humidity. In some cases, the ascorbic acid can be provided at concentration of from about 10 to 100 micrograms/ml. In still further cases, linoleic acid can be provided at a concentration of from about 5 to 80 micromolar. The present disclosure is not limited to synthetic leather formed from a particular source of keratinocytes. Indeed, the synthetic leather can be formed from a variety of primary and immortal keratinocytes, including, but not limited to Near-Diploid Immortalized Keratinocytes (NIKS) cells. In still further cases, the keratinocytes express exogenous wild-type or variant Kruppel-like factor (GKLF). In still further cases, the keratinocytes are derived from two different sources. In other cases, the synthetic leather has a surface electrical capacitance of from about 40 to about 240 pF. In some preferred cases, the skin equivalent has a surface electrical capacitance of from about 80 to about 120 pF. In other preferred cases, the content of ceramides 5, 6, and 7 in the skin equivalent can be from about 20 to about 50% of total ceramide content. In still other preferred cases, the content of ceramide 2 in the skin equivalent can be from about 10 to about 40% of total ceramide content. In still further cases, the present disclosure provides the skin equivalent made by the method just described.

Arranging Layers to Form a Layered Structure

Multiple cell layers can be arranged to form a layer structure, thus producing synthetic leathers described herein. In some cases, dermal layers and epidermal layers are formed separately and assembled by placing the epidermal layers atop of the dermal layers (e.g., when both an epidermal layer and a dermal layer are fully formed). In some cases, an epidermal layer can be grown atop a dermal layer. In certain cases, a basement membrane or basement membrane substitute can be placed between a dermal layer and an epidermal layer. For example, the cell layers can be manually placed in contact with one another or deposited in place by an automated, computer-aided machine such as a biofabricator, according to a computer script.

Before assembling multiple cell layers, one or more quality control steps can be performed. For example, Trans Epithelial Electrical Resistance (TEER) can be performed on epidermis before placement on dermis (e.g., 0 day), followed by histology analysis (e.g., minimum 3-5 days). Using methods provided herein, the risk of improperly formed layered structure or full thickness skin equivalents can be low.

Multiple cell layers can be assembled in various ways. In some cases, an epidermal layer and a dermal layer (with or without a basement membrane substitute) are placed on a scaffold (e.g., silk), e.g., to achieve thickness and tensile strength of natural leather. In some cases, an epidermal layer and multiple dermal layers (with or without a basement membrane substitute) are assembled without using a scaffold. Such assembly can achieve thickness and tensile strength that resemble natural leather. In some cases, an epidermal layer and multiple dermal layers (with or without a basement membrane substitute) are placed on a scaffold (e.g., silk) achieve thickness and tensile strength that resemble natural leather.

In some embodiments, chemical, mechanical, performance, strength, durability, moisture, dimensional tests or a combination thereof can be performed on one or more multiple cell layer, synthetic leathers, artificial epidermal layers, artificial dermal layers, layered structures, products produced therefrom. In some embodiments, a chemical, mechanical, performance, strength, durability, moisture, dimensional tests or a combination thereof can be performed using a non-standard test. In some embodiments, a chemical, mechanical, performance, strength, durability, moisture, dimensional tests or a combination thereof can be performed using a standard test. In some embodiments, a test can be performed as instructed and/or adopted and/or ratified and/or developed by the International Standards Organization (ISO), European standards body (CEN), ASTM International or by the International Union of Leather Technicians and Chemists (IULTCS). In some embodiments, a test in any one of Table 1- Table 11 or any variation thereof can be performed using any one or more corresponding method or any variation thereof.

TABLE 1

IULTCS - CHEMICAL TEST METHODS

| IU No. | Method name |
|---|---|
| IUC 1 | General comments |
| IUC 2 | Sampling |
| IUC 3 | Preparation of test material by grinding |
| IUC 4 | Determination of substances (fats and other soluble) soluble in Dichloromethane. |
| IUC 5 | Determination of volatile matter |
| IUC 6 | Determination of water soluble matter, water soluble inorganic matter and water soluble organic matter |
| IUC 7 | Determination of sulphated total ash and sulphated water insoluble ash |
| IUC 8 | Determination of chromic oxide |
| IUC 9 | Determination of water soluble magnesium salts |
| IUC 10 | Determination of nitrogen and hide substance |
| IUC 11 | Determination of pH and difference figure |
| IUC 13 | Determination of zirconium |
| IUC 15 | Determination of phosphorus |
| IUC 16 | Determination of aluminium |
| IUC 17 | Determination of hydroxyproline in materials containing collagen |
| IUC 18 | Photometric Determination of chromium (VI) using 1,5-Diphenylcarbazide |

TABLE 1-continued

IULTCS - CHEMICAL TEST METHODS

| IU No. | Method name |
|---|---|
| IUC 19 | Determination of formaldehyde content of leather |
| IUC 20 | Method for the detection of certain AZO colourants in dyed leather |
| IUC 21 | Method for the detection of certain AZO colourants in dyestuff mixtures |
| IUC 22 | Determination of aluminium oxide content of aluminium tanning agents |
| IUC 23 | Determination of the pH of aqueous solutions of aluminium tanning agents |
| IUC 24 | Determination of basicity of aluminium tanning agents. |
| IUC 25 | Determination of pentachlorophenol content |

TABLE 2

IULTCS - PHYSICAL TEST METHODS

| IU No. | Method name |
|---|---|
| IUP 1 | General remarks |
| IUP 2 | Sampling |
| IUP 3 | Conditioning |
| IUP 4 | Measurement of thickness |
| IUP 5 | Measurement of apparent density |
| IUP 6 | Measurement of tensile strength and percentage elongation |
| IUP 7 | Measurement of static absorption of water |
| IUP 8 | Measurement of tear load - Double edge tear |
| IUP 9 | Measurement of distension and strength of grain by the Ball Burst Test |
| IUP 10 | Water resistance of flexible leather |
| IUP 11 | Measurement of water resistance of heavy leather |
| IUP 12 | Measurement of resistance to grain cracking and the grain crack index |
| IUP 13 | Measurement of two dimensional extension |
| IUP 14 | Measurement of waterproofness of gloving leathers |
| IUP 15 | Measurement of water vapour permeability |
| IUP 16 | Measurement of shrinkage temperature up to 100° C. |
| IUP 17 | Assessment of the resistance of air dry insole leathers to heat |
| IUP 18 | Resistance of air dry lining leathers to heat |
| IUP 19 | Resistance of air dry upper leather to heat |
| IUP 20 | Measurement of flex resistance by flexometer method |
| IUP 21 | Measurement of set in lasting |
| IUP 22 | Assessment of scuff damage by use of the viewing box |
| IUP 23 | Measurement of scuff damage |
| IUP 24 | Measurement of surface shrinkage by immersion in boiling water |
| IUP 26 | Measurement of resistance to abrasion of heavy leather |
| IUP 28 | Measurement of the resistance to bending of heavy leather |
| IUP 29 | Measurement of cold crack temperature of surface coatings |
| IUP 30 | Measurement of water vapour absorption and desorption (See IUP 42) |
| IUP 32 | Measurement of area |
| IUP 35 | Measurement of dry heat resistance of leather |
| IUP 36 | Measurement of leather softness |
| Draft IUP 37 | Measurement of water repellancy of garment leather |
| IUP 38 | Measurement of heat resistance of patent leather |
| IUP 39 | Measurement of flex resistance by the vamp flex method |
| IUP 40 | Measurement of tear load - Single edge tear |
| IUP 41 | Measurement of surface coating thickness |
| IUP 42 | Measurement of water vapour absorption |
| IUP 43 | Measurement of extension set |
| IUP 44 | Measurement of stitch tear resistance |
| Draft IUP 45 | Measurement of water penetration pressure |
| Draft IUP 46 | Measurement of fogging characteristics |
| Draft IUP 47 | Measurement of resistance to horizontal spread of flame |
| Draft IUP 48 | Measurement of abrasion resistance of upholstery leather |
| Development | Measurement of bagginess (IUP 49) |
| Development | Measurement of soiling (IUP 50) |
| Development | Measurement of Surface Friction (IUP 51) |
| Development | Measurement of Compressibility (IUP 52) |

TABLE 3

IULTCS - FASTNESS TEST METHODS

| IU No. | Method name |
|---|---|
| IUF 105 | Numbering code for fastness tests |
| IUF 120 | Principles of colour fastness testing |
| IUF 131 | Grey scale for assessing change in colour |
| IUF 132 | Grey scale for assessing staining |
| IUF 151 | Preparation of Standard Storable Chrome leather |
| IUF 201 | Approx. determination of solubility of leather dyes |
| IUF 202 | Fastness to acid of dye solutions |
| IUF 203 | Stability to acid of dye solutions |
| IUF 205 | Stability to hardness of dye solutions |
| IUF 401 | Fastness to daylight |
| IUF 402 | Fastness to light (Xenon arc) |
| IUF 420 | Fastness to water spotting |
| IUF 421 | Fastness to water |
| IUF 423 | Fastness to washing |
| IUF 424 | Fastness to formaldehyde |
| IUF 426 | Fastness to perspiration |
| IUF 434 | Fastness to dry-cleaning of small samples |
| IUF 435 | Fastness to machine washing |
| IUF 441 | Fastness in respect to staining raw crepe rubber |
| IUF 442 | Fastness in respect of staining plasticised PVC |
| IUF 450 | Fastness to and fro rubbing |
| IUF 454 | Fastness to buffing of dyed leather |
| IUF 458 | Fastness to ironing |
| IUF 470 | Adhesion of finish |
| IUF 412 | Change of colour with accelerated ageing |

TABLE 4

ASTM's Leather Standards-Apparel Test Title

| Designation | Test Title |
|---|---|
| D1913 - 00(2015) | Standard Test Method for Resistance to Wetting of Garment-Type Leathers (Spray Test) |
| D2096 - 11 | Standard Test Method for Colorfastness and Transfer of Color in the Washing of Leather |
| D2821 - 14 | Standard Test Method for Measuring the Relative Stiffness of Leather by Means of a Torsional Wire Apparatus |
| D5053 - 03(2015) | Standard Test Method for Colorfastness of Crocking of Leather |
| D5552 - 10(2015) | Standard Test Method for Resistance of Colored Leather to Bleeding |
| D6012 - 03(2013) | Standard Test Method for Determination of Resistance of Leather to (Bleeding) Color Stain Transfer |
| D6013 - 00(2010) | Standard Test Method for Determination of Area Stability of Leather to Laundering |
| D6014 - 00(2015) | Standard Test Method for Determination of Dynamic Water Absorption of Leather Surfaces |

TABLE 5

ASTM's Leather Standards-Chemical Analysis

| Designation | Test Title |
|---|---|
| D2617 - 12 | Standard Test Method for Total Ash in Leather |
| D2807 - 93(2015) | Standard Test Method for Chromic Oxide in Leather (Perchloric Acid Oxidation) |
| D2810 - 13 | Standard Test Method for pH of Leather |
| D2868 - 10(2015) | Standard Test Method for Nitrogen Content (Kjeldahl) and Hide Substance Content of Leather, Wet Blue and Wet White |
| D3495 - 10(2015) | Standard Test Method for Hexane Extraction of Leather |
| D3790 - 79(2012) | Standard Test Method for Volatile Matter (Moisture) of Leather by Oven Drying |
| D3897 - 91(2012) | Standard Practice for Calculation of Basicity of Chrome Tanning Liquors |
| D3898 - 93(2015) | Standard Test Method for Chromic Oxide in Basic Chromium Tanning Liquors |

TABLE 5-continued

ASTM's Leather Standards-Chemical Analysis

| Designation | Test Title |
|---|---|
| D3913 - 03(2015) | Standard Test Method for Acidity in Basic Chromium Tanning Liquors |
| D4653 - 87(2015) | Standard Test Method for Total Chlorides in Leather |
| D4654 - 87(2015) | Standard Test Method for Sulfate Basicity in Leather |
| D4655 - 95(2012) | Standard Test Methods for Sulfates in Leather (Total, Neutral, and Combined Acid) |
| D4906 - 95(2012) | Standard Test Method for Total Solids and Ash Content in Leather Finishing Materials |
| D4907 - 10(2015) | Standard Test Method for Nitrocellulose in Finish on Leather |
| D5356 - 10(2015) | Standard Test Method for pH of Chrome Tanning Solutions |
| D6016 - 06(2012) | Standard Test Method for Determination of Nitrogen, Water Extractable in Leather |
| D6017 - 97(2015) | Standard Test Method for Determination of Magnesium Sulfate (Epsom Salt) in Leather |
| D6018 - 96(2012) | Standard Test Method for Determining the Presence of Lead Salts in Leather |
| D6019 - 15 | Test Method for Determination of Chromic Oxide in Basic Chromium Tanning Liquors (Ammonium Persulfate Oxidation) |

TABLE 6

ASTM's Leather Standards-Fats and Oils

| Designation | Test Title |
|---|---|
| D5346 - 93(2009) | Standard Test Method for Determination of the Pour Point of Petroleum Oil Used in Fatliquors and Softening Compounds |
| D5347 - 95(2012) | Standard Test Method for Determination of the Ash Content of Fats and Oils |
| D5348 - 95(2012) | Standard Test Method for Determination of the Moisture Content of Sulfonated and Sulfated Oils by Distillation with Xylene |
| D5349 - 95(2012) | Standard Test Method for Determination of the Moisture and Volatile Content of Sulfonated and Sulfated Oils by Hot-Plate Method |
| D5350 - 95(2012) | Standard Test Method for Determination of Organically Combined Sulfuric Anhydride by Titration, Test Method A |
| D5351 - 93(2009) | Standard Test Method for Determination of Organically Combined Sulfuric Anhydride by Extraction Titration, Test Method B |
| D5352 - 95(2012) | Standard Test Method for Determination of Organically Combined Sulfuric Anhydride Ash - Gravimetric, Test Method C |
| D5353 - 95(2012) | Standard Test Method for Determination of Total Desulfated Fatty Matter |
| D5354 - 95(2012) | Standard Test Method for Determination of Total Active Ingredients in Sulfonated and Sulfated Oils |
| D5355 - 95(2012) | Standard Test Method for Specific Gravity of Oils and Liquid Fats |
| D5439 - 95(2012) | Standard Test Method for Determination of Sediment in Moellon |
| D5440 - 93(2009) | Standard Test Method for Determining the Melting Point of Fats and Oils |
| D5551 - 95(2012) | Standard Test Method for Determination of the Cloud Point of Oil |
| D5553 - 95(2012) | Standard Test Method for Determination of the Unsaponifiable Nonvolatile Matter in Sulfated Oils |
| D5554 - 15 | Standard Test Method for Determination of the Iodine Value of Fats and Oils |
| D5555 - 95(2011) | Standard Test Method for Determination of Free Fatty Acids Contained in Animal, Marine, and Vegetable Fats and Oils Used in Fat Liquors and Stuffing Compounds |
| D5556 - 95(2011) | Standard Test Method for Determination of the Moisture and Other Volatile Matter Contained in Fats and Oils Used in Fat Liquors and Softening Compounds |

TABLE 6-continued

ASTM's Leather Standards-Fats and Oils

| Designation | Test Title |
|---|---|
| D5557 - 95(2011) | Standard Test Method for Determination of Insoluble Impurities Contained in Fats and Oils Used in Fat Liquors and Stuffing Compounds |
| D5558 - 95(2011) | Standard Test Method for Determination of the Saponification Value of Fats and Oils |
| D5559 - 95(2011) | Standard Test Method for Determination of Acidity as Free Fatty Acids/Acid Number in the Absence of Ammonium or Triethanolamine Soaps in Sulfonated and Sulfated Oils |
| D5560 - 95(2011) | Standard Test Method for Determination of Neutral Fatty Matter Contained in Fats and Oils |
| D5562 - 95(2011) | Standard Test Method for Determination of the Acidity as Free Fatty Acids/Acid Number in the Presence of Ammonium or Triethanolamine Soaps |
| D5564 - 95(2011) | Standard Test Method for Determination of the Total Ammonia Contained in Sulfonated or Sulfated Oils |
| D5565 - 95(2011) | Standard Test Method for Determination of the Solidification Point of Fatty Acids Contained in Animal, Marine, and Vegetable Fats and Oils |
| D5566 - 95(2011) | Standard Test Method for Determination of Inorganic Salt Content of Sulfated and Sulfonated Oils |

TABLE 7

ASTM's Leather Standards-Footwear

| Designation | Test Title |
|---|---|
| D2098 - 13 | Standard Test Method for Dynamic Water Resistance of Shoe Upper Leather by the Dow Corning Leather Tester |
| D2099 - 14 | Standard Test Method for Dynamic Water Resistance of Shoe Upper Leather by the Maeser Water Penetration Tester |
| D2210 - 13 | Standard Test Method for Grain Crack and Extension of Leather by the Mullen Test |
| D2322 - 14 | Standard Test Method for Resistance of Shoe Upper Leather to Artificial Perspiration |
| D2346 - 13 | Standard Test Method for Apparent Density of Leather |
| D2941 - 13 | Standard Test Method for Measuring Break Pattern of Leather (Break Scale) |
| D6015 - 14 | Standard Test Method for Static Water Absorption of Leather |
| D7340 - 07(2012)e1 | Standard Practice for Thermal Conductivity of Leather |

TABLE 8

ASTM's Leather Standards-Physical Properties

| Designation | Test Title |
|---|---|
| D1516 - 05(2010) | Standard Test Method for Width of Leather |
| D1610 - 01(2013) | Standard Practice for Conditioning Leather and Leather Products for Testing |
| D1813 - 13 | Standard Test Method for Measuring Thickness of Leather Test Specimens |
| D1814 - 70(2015) | Standard Test Method for Measuring Thickness of Leather Units |
| D1815 - 00(2015) | Standard Test Method for Water Absorption (Static) of Vegetable Tanned Leather |
| D2207 - 00(2015) | Standard Test Method for Bursting Strength of Leather by the Ball Method |
| D2209 - 00(2015) | Standard Test Method for Tensile Strength of Leather |
| D2211 - 00(2015) | Standard Test Method for Elongation of Leather |

TABLE 8-continued

ASTM's Leather Standards-Physical Properties

| Designation | Test Title |
|---|---|
| D2212 - 00(2015) | Standard Test Method for Slit Tear Resistance of Leather |
| D2347 - 00(2015) | Standard Test Method for Measuring Area of Leather Test Specimens |
| D2813 - 03(2013) | Standard Practice for Sampling Leather for Physical and Chemical Tests |
| D4704 - 13 | Standard Test Method for Tearing Strength, Tongue Tear of Leather |
| D4705 - 13 | Standard Test Method for Stitch Tear Strength of Leather, Double Hole |
| D5052 - 00(2010) | Standard Test Method for Permeability of Leather to Water Vapor |
| D6076 - 08(2013) | Standard Test Method for Shrinkage Temperature of Leather |
| D6182 - 00(2015) | Standard Test Method for Flexibility and Adhesion of Finish on Leather |
| D6183 - 00(2015) | Standard Test Method for Tackiness of Finish on Leather |
| D7255 - 14 | Standard Test Method for Abrasion Resistance of Leather (Rotary Platform, Abraser Method) |

TABLE 9

ASTM's Leather Standards-Upholstery

| Designation | Test Title |
|---|---|
| D1912 - 00(2010) | Standard Test Method for Cold-Crack Resistance of Upholstery Leather |
| D2097 - 03(2010) | Standard Test Method for Flex Testing of Finish on Upholstery Leather |
| D2208 - 00(2010) | Standard Test Method for Breaking Strength of Leather by the Grab Method |
| D6077 - 10 | Standard Test Method for Trapezoid Tearing Strength of Leather |
| D6116 - 00(2010) | Standard Test Method for Blocking |
| D7912 - 14 | Standard Test Method for Resistance of Finish to Heat Aging (Finish Stability) |

TABLE 10

ASTM's Leather Standards-Vegetable Leather

| Designation | Title |
|---|---|
| D1611 - 12 | Standard Test Method for Corrosion Produced by Leather in Contact with Metal |
| D2213 - 00(2010) | Standard Test Method for Compressibility of Leather |
| D2875 - 00(2010) | Standard Test Method for Insoluble Ash of Vegetable-Tanned Leather |
| D2876 - 00(2010) | Standard Test Method for Water-Soluble Matter of Vegetable-Tanned Leather |
| D4786 - 00(2010) | Standard Test Method for Stitch Tear Strength, Single Hole |
| D4831 - 00(2010) | Standard Test Method for Buckle Tear Strength of Leather |
| D4899 - 99(2009) | Standard Practice for Analysis of Vegetable Tanning Materials-General |
| D4900 - 99(2009) | Standard Test Method for Lignosulfonates (Sulfite Cellulose) in Tanning Extracts |
| D4901 - 99(2009) | Standard Practice for Preparation of Solution of Liquid Vegetable Tannin Extracts |
| D4902 - 99(2009) | Standard Test Method for Evaporation and Drying of Analytical Solutions |
| D4903 - 99(2009) | Standard Test Method for Total Solids and Water in Vegetable Tanning Material Extracts |
| D4904 - 99(2009) | Standard Practice for Preparation of Solution of Liquid Vegetable Tannin Extracts |
| D4905 - 99(2009) | Standard Practice for Preparation of Solution of Solid, Pasty and Powdered Vegetable Tannin Extracts |
| D6020 - 00(2010) | Standard Practice for Calculation of (Non-Mineral) Combined Tanning Agents and Degree of Tannage |
| D6075 - 13 | Standard Test Method for Cracking Resistance of Leather |
| D6401 - 99(2009) | Standard Test Method for Determining Non-Tannins and Tannin in Extracts of Vegetable Tanning Materials |
| D6402 - 99(2014) | Standard Test Method for Determining Soluble Solids and Insolubles in Extracts of Vegetable Tanning Materials |
| D6403 - 99(2014) | Standard Test Method for Determining Moisture in Raw and Spent Materials |
| D6404 - 99(2014) | Standard Practice for Sampling Vegetable Materials Containing Tannin |
| D6405 - 99(2014) | Standard Practice for Extraction of Tannins from Raw and Spent Materials |
| D6406 - 99(2014) | Standard Test Method for Analysis of Sugar in Vegetable Tanning Materials |
| D6407 - 99(2014) | Standard Test Method for Analysis of Iron and Copper in Vegetable Tanning Materials |
| D6408 - 99(2014) | Standard Test Method for Analysis of Tannery Liquors |
| D6409 - 99(2014) | Standard Practice for Color Tests with Sheepskin Skiver |
| D6410 - 99(2014) | Standard Test Method for Determining Acidity of Vegetable Tanning Liquors |

TABLE 11

ASTM's Leather Standards-Wet Blue

| Designation | Title |
|---|---|
| D4576 - 08(2013) | Standard Test Method for Mold Growth Resistance of Wet Blue |
| D6656 - 14b | Standard Test Method for Determination of Chromic Oxide in Wet Blue (Perchloric Acid Oxidation) |
| D6657 - 14ae1 | Standard Test Method for pH of Wet Blue |
| D6658 - 08(2013) | Standard Test Method for Volatile Matter (Moisture) of Wet Blue by Oven Drying |
| D6659 - 10(2015) | Standard Practice for Sampling and Preparation of Wet Blue for Physical and Chemical Tests |
| D6714 - 01(2015) | Standard Test Method for Chromic Oxide in Ashed Wet Blue (Perchloric Acid Oxidation) |
| D6715 - 13 | Standard Practice for Sampling and Preparation of Fresh or Salt-Preserved (Cured) Hides and Skins for Chemical and Physical Tests |
| D6716 - 08(2013) | Standard Test Method for Total Ash in Wet Blue or Wet White |
| D7476 - 08(2013) | Standard Test Method for Brine Saturation Value of Cured (Salt-Preserved) Hides and Skins |
| D7477 - 08(2013) | Standard Test Method for Determining the Area Stability of Wet Blue Submersed in Boiling Water |
| D7584 - 10(2015) | Standard Test Method for Evaluating the Resistance of the Surface of Wet Blue to the Growth of Fungi in an Environmental Chamber |
| D7674 - 14a | Standard Test Method for Hexane/Petroleum Ether Extract in Wet Blue and Wet White |
| D7816 - 12 | Standard Test Method for Enumeration of Halophilic and Proteolytic Bacteria in Raceway Brine, Brine-Cured Hides and Skins |
| D7817 - 12 | Standard Test Method for Enumeration of Yeast and Mold in Raceway Brine, Brine-Cured Hides and Skins |
| D7818 - 12 | Standard Test Method for Enumeration of Proteolytic Bacteria in Fresh (Uncured) Hides and Skins |
| D7819 - 12 | Standard Test Method for Enumeration of Yeast and Mold on Fresh (Uncured) Hides and Skins |

In some embodiments, leather products can have physical properties similar to real leather. In some embodiments, a synthetic leather disclosed herein or a leather product made therefrom can tensile strength as measured by ASTM D-2209-95 of at least about 20, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1300, 1400, 1500, 1600, 1700, 1800, 1900, 2000 lbs/in$^2$. In some embodiments, a synthetic leather disclosed herein or a leather product made therefrom can tensile strength as measured by ASTM D-2209-95 of less than about 5000, 4000, 3000, 2000, 1900, 1800, 1700, 1600, 1500, 1400, 1300, 1200, 1100, 1000, 950, 900, 850, 800, 750, 700, 650, 600, 550, 500, 450, 400, 350, 300, 250, 200, 100, 90, 80, 70, 60, 50, 40, 30, 20 lbs/in$^2$.

In some embodiments, a synthetic leather disclosed herein or a leather product made therefrom can have a slit of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 lbs as measured by ASTM-D2212-94. In some embodiments, a synthetic leather disclosed herein or a leather product made therefrom can have a slit of less than about 200, 150, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 lbs as measured by ASTM-D2212-94. In some embodiments, a synthetic leather disclosed herein or a leather product made therefrom can have a stitch of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 100 when measured in accordance with ASTM-D4705-93. In some embodiments, a synthetic leather disclosed herein or a leather product made therefrom can have a stitch of less than about 200, 150, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1. In some embodiments, a synthetic leather disclosed herein or a leather product made therefrom can have the slit and stitch values are at least about 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 100 lbs., when measured in accordance with their respective tests. In some embodiments, a synthetic leather disclosed herein or a leather product made therefrom can have a Bally flex of at least about 5000, 6000, 7000, 8000, 9000, 10000, 15000, 20000, 25000, 30000, 35000, 40000, 45000, 50,000, 55000, 60000, 65000, 70000, 80000 as measured by ASTM D6182.

Multiple cell layers can be assembled to form a synthetic leather (e.g., a full thickness skin equivalent). A synthetic leather can comprise a top part, a middle part and a bottom part. The top part can comprise an epidermal layer. For example, the top part can be a single layer epidermal layer. The middle part can comprise a basement membrane substitute. In some cases, the middle part does not have a basement membrane substitute. For example, the middle part can have a layer of negligible thickness. The bottom part can have one or more dermal layers. In some cases, the bottom part has a single dermal layer placed on a scaffold (e.g., silk). In some cases, the bottom part has multiple dermal layers (e.g., up to 5 layers) without any scaffold. In some cases, the bottom part has multiple dermal layers stacked atop each other and placed on a scaffold (e.g., silk).

Adhesiveness between epidermal and dermal layers can be strong enough to resist layer splitting. In some cases, the cells layers can be assembled by adhering on to a scaffold. Natural or synthetic adhesives can be used for the assembly. A natural adhesive can be fibrin glue, cold glues, animal glue (e.g., bone glue, fish glue, hide glue, hoof glue, rabbit skin glue, meat glue), blood albumen glue, casein glue, vegetable glues (e.g., starch, dextrin glues, Canada balsam, pine rosin based glue, cocconia, gum Arabic, postage stamp gum, latex, library paste, methyl cellulose, mucilage, resorcinol resin, or urea-formaldehyde resin), or any combination thereof. A synthetic adhesive can be Acrylonitrile, Cyanoacrylate (e.g., n-buthyl-2-cyanoacrylate glue), Acrylic, Resorcinol glue, Epoxy resins, Epoxy putty, Ethylene-vinyl acetate, Phenol formaldehyde resin, Polyamide, Polyester resins, Polyethylene, Polypropylene, Polysulfides, Polyurethane, Polyvinyl acetate (including white glue (e.g. Elmer's Glue) and yellow carpenter's glue (Aliphatic resin), Polyvinyl alcohol, Polyvinyl chloride (PVC), Polyvinyl chloride emulsion (PVCE), Polyvinylpyrrolidone Rubber cement, Silicones, and Styrene acrylic copolymer. For example, the assembly can be performed using fibrin glue. For example, the assembly can be performed using n-buthyl-2-cyanoacrylate glue.

In some cases, cell layers (e.g., substantially planar layers) are stacked to form a synthetic leather. A cell layer can have an orientation defined by the placement, pattern, or orientation of multicellular bodies. In some cases, each layer can be stacked with a particular orientation relative to the support substrate and/or one or more other layers. For example, one or more layers can be stacked with an orientation that includes rotation relative to the support substrate and/or the layer below, wherein the rotation can be between 0.1 and 180 degrees, for example, about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, and 180 degrees, or increments therein. In other cases, all layers are oriented substantially similarly.

Once stacking of the layers is complete, the layers in the three-dimensional construct can be allowed to fuse to one another to produce a synthetic leather. In some cases, the layers fuse in a cell culture environment (e.g., a Petri dish, cell culture flask, bioreactor, etc.). In some cases, the fusing take place over about 15, 20, 25, 30, 35, 40, 45, 50, 55, and 60 minutes, and increments therein. In other cases, fusing takes place over between 1 and 48 hours, e.g., over about 1, 2, 3, 4, 5, 6, 7, 8, 9, 10, 11, 12, 14, 16, 18, 20, 22, 24, 26, 28, 30, 32, 34, 36, 38, 40, 42, 44, 46, and 48 hours, and increments therein. For example, fusing can take place over about 2 hours to about 24 hours.

Culturing Condition

The cells and cell layers can be cultured in various cell culture conditions. The cells or cell layers can be cultured in vitro. For example, a dermal layer and/or an epidermal layer can be cultured in vitro. Alternatively, the cells or cell layers can be cultured in vivo. For example, a dermal layer and/or an epidermal layer can be cultured in vivo.

The cells and cell layers can be cultured with one or more supplements. The one or more supplements can be natural supplements, synthetic supplements, or a combination thereof. In some cases, a supplement can be an additive. In some cases, one or more of the supplements induce production and assembly of extracellular matrix from iPSC-derived fibroblasts, thus enhancing natural look of the synthetic leather. Exemplary supplements can include ECM components such as collagen and fibrin, growth factors, small molecules such as ascorbic acid or the like, macromolecules such as dextran sulphate, carrageenan, or the like.

The cell layers can be cultured with certain air humidity. For example, the cell layers (e.g., dermal layers or epidermal layers) can be cultured at from about 20% to about 100% humidity. For example, the humidity can be from about 40% to about 100%, from about 50% to about 95%, from about 45% to about 90%, from about 55% to about 95%, from about 60% to about 90%, from about 70% to about 80%, from about 71% to about 79%, from about 72% to about 78%, from about 73% to about 77%, from about 74% to about 76%, from about 60% to about 70%, from about 65% to about 75%, from about 70% to about 80%, from about 75% to about 85%, from about 80% to about 90%, from about 85% to about 95%, or from about 90% to about 100%, from about 40% to about 60%, from about 45% to about 55%, from about 46% to about 54%, from about 47% to about 53%, from about 48% to about 52%, from about 48% to about 53%, from about 49% to about 54%, or from about 47% to about 51%.

Leather Processing

Tanning

Methods herein can comprise tanning at least a portion of a synthetic leather, e.g., at least a portion of a dermal layer and/or an epidermal layer in the synthetic leather. Tanning can make a synthetic leather resemble a natural leather, which can be a durable and flexible material created by the tanning of animal rawhide and skin, often cattle hide. Tanning herein can refer to the process of treating the skins of animals to produce leather. Tanning can be performed various ways, including vegetable tanning (e.g., using tannin), chrome tanning (chromium salts including chromium sulfate), aldehyde tanning (using glutaraldehyde or oxazolidine compounds), syntans (synthetic tannins, using aromatic polymers), bacterial dyeing, and the like.

Tanning can be performed to convert proteins in the hide/skin into a stable material that will not putrefy, while allowing the material to remain flexible. Chromium can be used as tanning material. The pH of the cell layer or layered structure can be adjusted (e.g., lowered; e.g. to pH about 2.8-3.2) to enhance the tanning; following tanning the pH can be raised ("basification" to a slightly higher level, e.g., pH about 3.8-4.2).

Tanning can be performed on cell layers, e.g., dermal layers and epidermal layers. Tanning can also be performed on layered structures, e.g., layered structures comprising at least a dermal layer and at least an epidermal layer. In certain cases, tanning can also be performed on a synthesized leather. For example, tanning can be performed after forming cell layers, e.g., dermal layers or epidermal layers. For example, tanning can be performed after forming layered structures.

Tanning can be performed by modify the extracellular matrix (ECM) material. Tanning can be performed by modifying collagen in the ECM. The tanning can be performed using a tanning agent, e.g., chromium(III) sulfate ($[Cr(H_2O)_6]2(SO_4)_3$). Chromium(III) sulfate can dissolve to give the hexaaquachromium(III) cation, $[Cr(H_2O)_6]^{3+}$, which at higher pH undergoes processes called olation to give polychromium(III) compounds that are active in tanning, being the cross-linking of the collagen subunits. Some ligands include the sulfate anion, the collagen's carboxyl groups, amine groups from the side chains of the amino acids, as well as masking agents. Masking agents can be carboxylic acids, such as acetic acid, used to suppress formation of polychromium(III) chains. Masking agents can allow the tanner to further increase the pH to increase collagen's reactivity without inhibiting the penetration of the chromium (III) complexes. Tanning can increase the spacing between protein chains in collagen (e.g., from 10 to 17 Å), consistent with cross-linking by polychromium species, of the sort arising from olation and oxolation. The chromium can be cross-linked to the collagen. Chromium-tanned leather can contain between about 4% and 5% of chromium. This efficiency can be characterized by its increased hydrothermal stability of the leather, and its resistance to shrinkage in heated water. Other tanning agents can be used to tan the layered body and modify the collagen.

Tanning can also be performed using other minerals. In some cases, tanning can be performed using agent based on alum, zirconium, titanium, iron salts, or a combination thereof, Further Processing Cell layers, layered structures, and synthetic leathers made herein can be further processed after tanning. In some cases, methods provided herein further comprise one or more leather processing steps (e.g., those used in traditional leather formation). Examples of processing steps include: preserving, soaking, liming, unhairing, fleshing, splitting, deliming, reliming, bating, degreasing, frizzing, bleaching, colouring, pickling, depickling, tanning, re-tanning (e.g., if color is lost during processing), thinning, retanning, lubricating, crusting, wetting, sammying, shaving, rechroming, neutralizing, dyeing, fatliquoring, filling, stripping, stuffing, whitening, fixating, setting, drying, conditioning, milling (e.g., dry milling), staking, buffing, finishing, oiling, brushing, padding, impregnating, spraying, roller coating, curtain coating, polishing, plating, embossing, ironing, glazing, and tumbling.

The synthetic leather can be shaped by, for example, controlling the number, size, and arrangement of the multicellular bodies and/or the layers used to construct the animal skin, hide, or leather. In other cases, the animal skin, hide, or leather can be shaped by, for example, cutting, pressing, molding, or stamping. The shape the synthetic leather can be made to resemble a traditional animal skin, hide, or leather product.

Methods herein can comprise removing a portion of a synthetic leather produced herein. In some cases, the method comprises removing at least a portion of epidermal layer to form a removed product. For example, the removing can be shaving.

Pigmentation

Methods herein can comprise pigmenting the synthetic leather. In some cases, pigmentation can be performed by introducing pigments producing cells (e.g., melanocytes) in the synthetic leather. In some cases, the synthetic leather comprises functional live melanocytes. The melanocytes can have a similar location to that in the human skin. In some cases, melanin can be constitutively produced by melanocytes. In some cases, melanin can be transferred to keratinocytes. In some cases, melanocytes are produced upon stimulation, e.g., UV radiation or by propigmenting active agents, such as alpha melanocyte stimulating hormone (aMSH), endothelin 1 (ET1), stem cell factor (SCF), prostaglandins E2 and F2a (PGE2, PGF2a), basic fibroblast growth factor (bFGF) or nerve growth factor (NGF).

Differentiation of Progenitor Cells to Cells in a Synthetic Leather

Cells in epidermal layers, such as keratinocytes and melanocytes, as well as cells in dermal layers, such as fibroblasts can be derived, e.g., differentiated, from progenitor cells, such as iPSCs. In other case, primary cells or cultured cells derived from primary cells can be used to form cell layers to make synthetic leather.

Various methods of differencing iPSCs to cells in a synthetic leather, e.g., keratinocytes, melanocytes, or fibroblasts can be used. In some cases, differentiation of iPSCs to keratinocytes and building 3D epidermis from the iPSC-derived keratinocytes can be performed using method described by Petrova et al., 3D In vitro model of a functional epidermal permeability barrier from human embryonic stem cells and induced pluripotent stem cells. Stem Cell Reports.

2014 Apr. 24; 2(5):675-89. In other cases, cell layers can be formed using primary cells. For example, building 3D epidermis from primary keratinocytes can be performed using the method described in Sun R et al., Lowered humidity produces human epidermal equivalents with enhanced barrier properties. Tissue Eng Part C Methods. 2015 January; 21(1):15-22.

In some cases, the methods described herein provide high-throughput methods that reliably, accurately, and reproducibly scale up to commercial levels the production of synthetic leather. Advantages of the synthetic leather, engineered epidermal equivalent, engineered full thickness skin equivalent and methods of making the same disclosed herein include, but are not limited to, production of customized tissues in a reproducible, high throughput and easily scalable fashion with appealing appearance, texture, thickness, and durability. In some embodiments, the methods described herein can produce increase yields of one or more of an epidermal layer, dermal layer, layered structure or synthetic leather. In some embodiments, increase yields can be at least about 0.5, 0.6, 0.7, 0.8, 0.9, 1, 1.5, 2, 2.5, 3, 3.5, 4, 5, 6, 7, 8, 9, 10, 11, 12, 13, or about 15 times yield compared to a comparable method. In some embodiments, the methods disclosed herein can reduce the cost of the manufacture of synthetic leathers, artificial epidermal layers, artificial dermal layers, layered structures, and products produced therefrom. In some embodiments, the methods disclosed herein can produce uniform thickness synthetic leathers, artificial epidermal layers, artificial dermal layers, layered structures, and products produced therefrom. In some embodiments, the synthetic leathers, artificial epidermal layers, artificial dermal layers, layered structures, and products produced therefrom can have a substantially uniform thickness, length and/or width. In some embodiments, cells in any one or more of the epidermal layers, dermal layers, layered structures can be homogeneously distributed. In some embodiments, cells in any one or more of the epidermal layers, dermal layers, layered structures can be heterogeneously distributed.

Comparative Analysis of Epidermal Equivalent

Figure 4A:
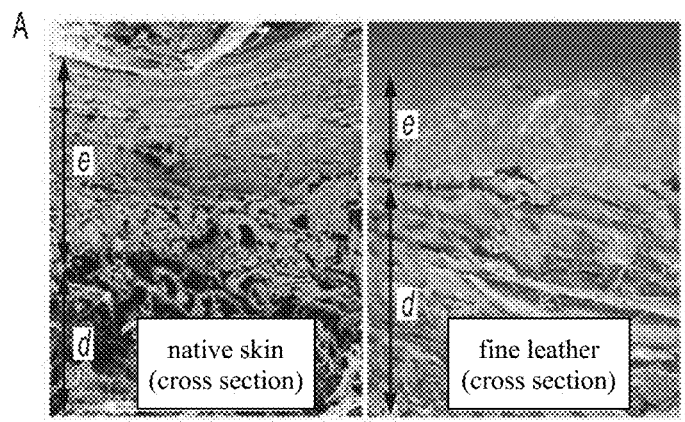
FIGS. 4A-4C illustrate a comparative analysis of leather (FIG. 4A), native skin (FIG. 4B) and epidermal equivalent (FIG. 4C).
Figure 4B:
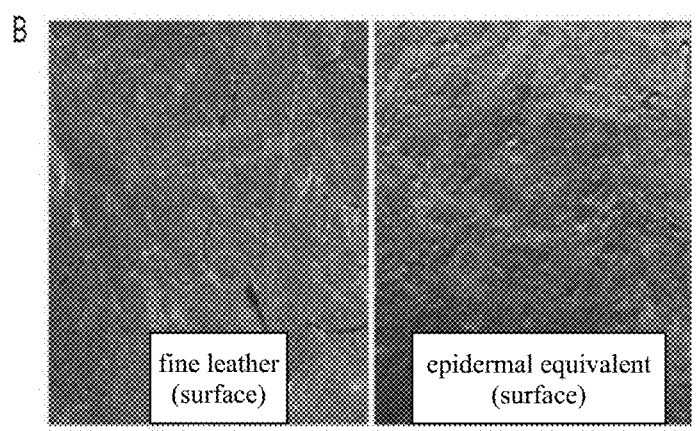
Figure 4C:
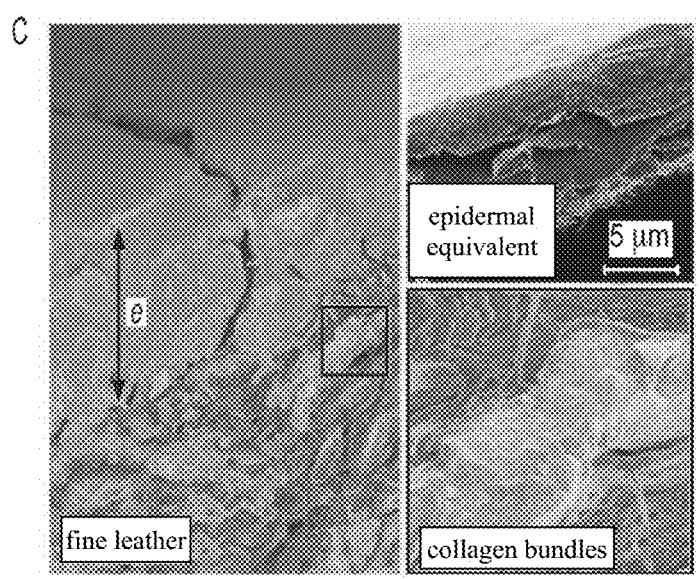

FIG. 4A-4C. Illustrates a Comparative analysis of fine leather, native skin and epidermal equivalent. FIG. 4A illustrates FESEM of longitudinal sections of native skin and fine leather. FIG. 4A show distinct morphological structures of epidermis (e) and dermis (d). Tanning permanently altered the structure of the skin. Borders between the individual cells in epidermis became indistinguishable. Removing moisture caused collagen bundles in dermis to become more compact and durable. Magnification: 1000×.

FIG. 4B depicts FESEM images. In one instance, FIG. 4B depicts that both surface of fine leather and surface of epidermal equivalents, have a similar smooth appearance indicating that they will likely induce a comparable tactile (touch) experience. Magnification: 2000×.

FIG. 4C depicts FESEM of longitudinal sections of fine leather and epidermal equivalent. Before the tanning takes place, similar to epidermis of native skin FIG. 4A, individual cell layers are distinguishable in epidermal equivalent. As collagen in the dermis can be responsible largely for tensile strength of the skin, collagen bundles can give thickness and durability to leather (inset), but may not give sensory experience, which may entirely rely on outer layers of epidermis.

Figure 5A:
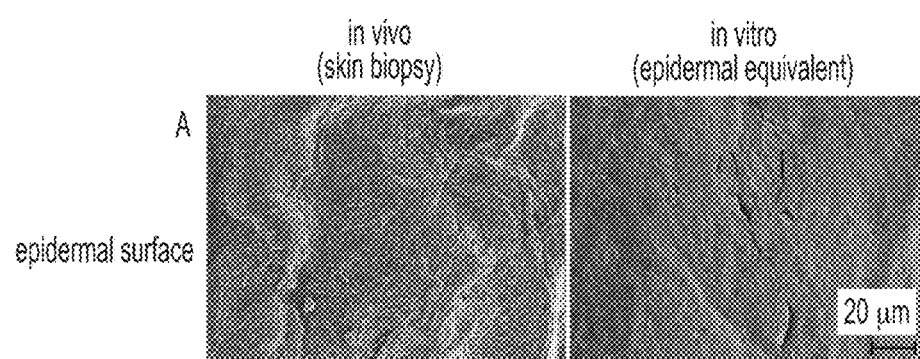
FIGS. 5A-5C illustrate a comparative analysis of stratum corneum of native skin and epidermal equivalent.
Figure 5B:
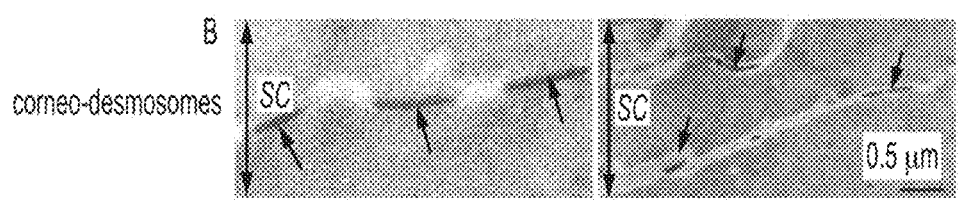
Figure 5C:
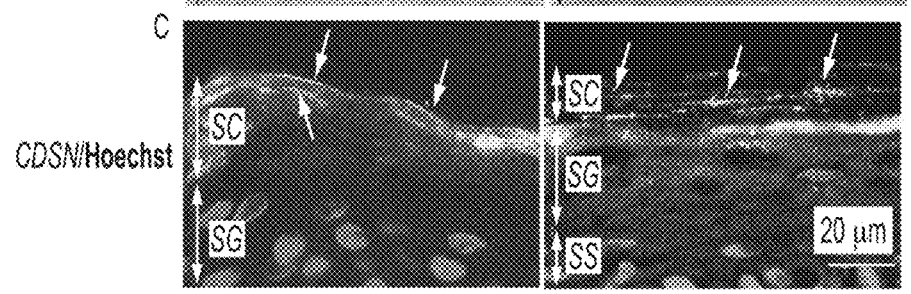
Figures 9A, 9B, 9C, 9D:
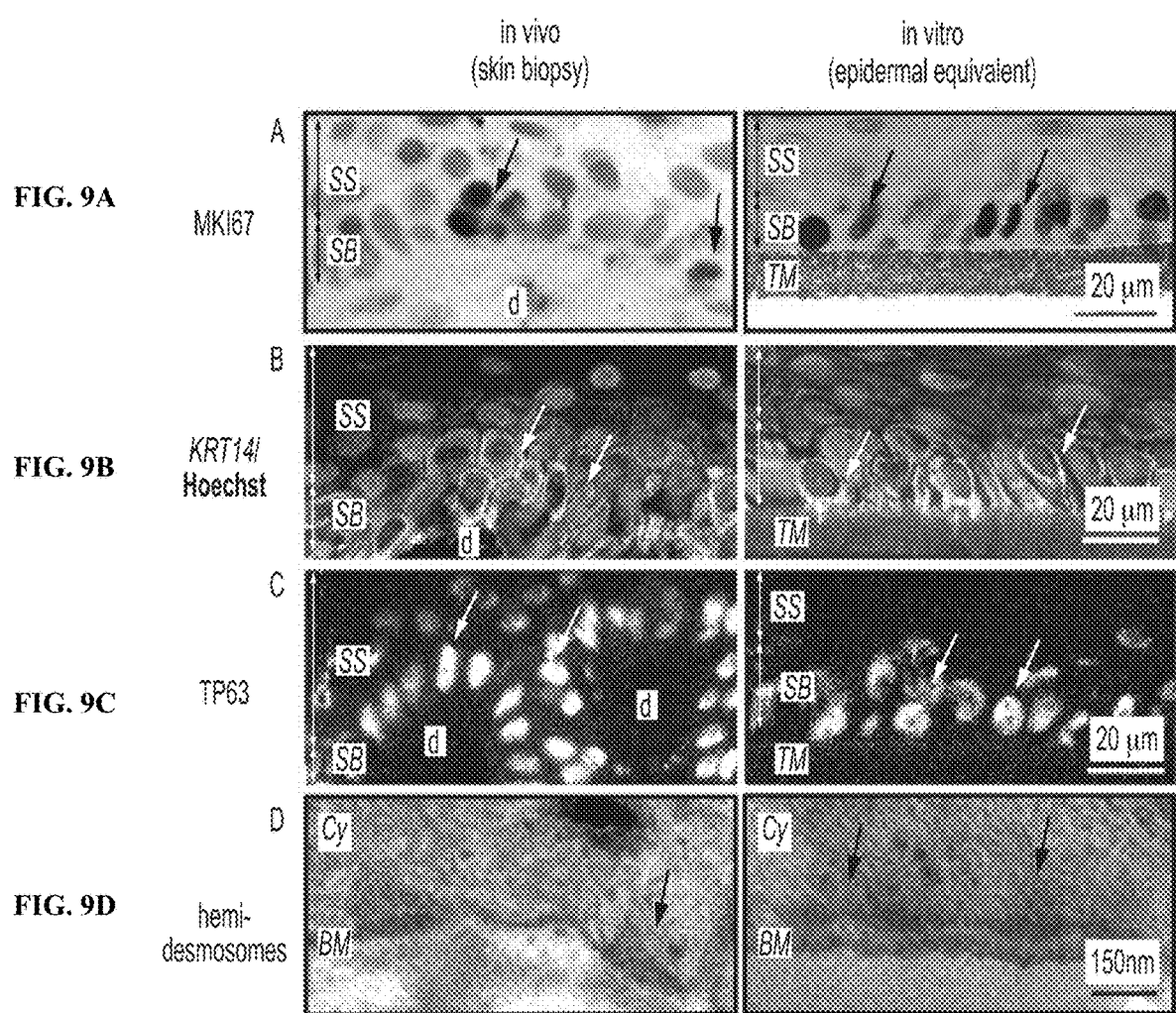
FIGS. 9A-9C illustrate a comparative analysis of stratum basale of native skin and epidermal equivalent. MKI67 (FIG. 9A), a marker of proliferation, keratin 14 (KRT14.
FIG. 9D depicts hemi-desmosomes in both native skin in vivo and epidermal equivalents generated in vitro.

FIG. 5A-5C illustrate a comparative analysis of stratum corneum (SC; cornified layer) of native skin and epidermal equivalent. FIG. 5A depicts FESEM images showing the surface of epidermal equivalents appear smoother than the surface of native skin, which may be due to the controlled environment of cell culture. FIG. 5B illustrates using TEM corneodesmosomes (arrows), the principal "mechanical" junctions of the SC, could be detected as electron denser areas in epidermal equivalents. FIG. 5C illustrates that corneodesmosin (CDSN) can be synthesized and excreted into the extracellular spaces by cells in SG, shortly before onset of cornification. CDSN can embed within the intercellular portions of the SG desmosomes occupied by cadherins and in such a way can form corneodesmosomes. Arrows point to similarly aligned dotty accumulations of CDSN in SC of native skin and epidermal equivalent, likely representing corenodesmosomes. SC, stratum corneum; SG, stratum granulosum; SS, stratum spinosum.

FIG. 6A-6E illustrate a comparative analysis of stratum granulosum (SG; granular layer) of native skin and epidermal equivalent. FIG. 6A illustrates that Loricrin (LOR) staining. LOR is a major protein component of the cornified cell envelope and can be expressed in the granular layer of keratinizing epithelia. A similar LOR expression pattern (dark brown pigment on H&E-stained tissue sections pointed by arrows) in SG was detected in both epidermis of native skin (left side of the panel) and epidermal equivalent (right side of the panel). d, dermis; H&E, hematoxylin & eosin; SB, stratum basale; SC, stratum corneum; SG, stratum granulosum; SS, stratum spinosum; *, Transwell filter membrane. In FIG. 6B, epidermal $Ca^{++}$ gradient can be captured on transmission electron microscopy as electron-dense precipitates. $Ca^{++}$ deposits were present in SG and absent from SC in both native skin in vivo (left side of panel) and epidermal equivalents generated in vitro (right side of the panel). SG, stratum granulosum; SS, stratum spinosum. In FIG. 6C, permeability barrier integrity was assessed by lanthanum perfusion. Lanthanum was visualized as electron-dense deposits in the extracellular spaces of the viable SG, demonstrating that lanthanum and, by extension, water and other small ions can pass between keratinocytes in this stratum. In contrast, lanthanum cannot penetrate further into the SC because a functioning lipid barrier is blocking its movement upward. Epidermal equivalent generated in vitro, demonstrated equally functional permeability barrier as native skin. SG, stratum granulosum; SS, stratum spinosum. FIG. 6D illustrates that tight junction protein 1/zonula occludens-1 (TJP1/ZO-1) anchors tight junction strand proteins, which are fibril-like structures within the lipid bilayer, to the actin cytoskeleton. Arrows point to similarly aligned bright green cell membrane-associated accumulations of TJP1/ZO-1 in SG of native skin in vivo (left side of panel) and epidermal equivalents generated in vitro (right side of the panel). SC, stratum corneum; SG, stratum granulosum; SS, stratum spinosum. FIG. 6E illustrates that Filaggrin (FLG) monomers, tandemly clustered into a large, 350 kDa protein precursor known as profilaggrin, are present in the keratohyalin granules in cells of the SG. Arrows point to similarly aligned bright red granule and cell membrane-associated accumulations of FLG in SG of native skin in vivo (left side of panel) and epidermal equivalents, generated in vitro (right side of the panel). SC, stratum corneum; SG, stratum granulosum; SS, stratum spinosum.

FIG. 7A-7C illustrate lipid bilayer formation in native skin and epidermal equivalents assessed with TEM. In FIG. 7A white arrows point to normal lipid secretion at the border of SC and SG in both native skin in vivo (left side of panel) and epidermal equivalents generated in vitro (right side of the panel). In FIG. 7B, lamellar bodies (white arrowheads) are seen in the SG of both native skin in vivo (left side of panel) and epidermal equivalents generated in vitro (right side of the panel). FIG. 7C depicts normal lipid bilayer (LB) morphology of native skin in vivo (left side of panel). Lipid bilayers in epidermal equivalents, generated in vitro (right side of the panel), had a similar appearance. SC, stratum corneum.

FIG. 8A-8D illustrate comparative analysis of markers of suprabasal layers of native skin and epidermal equivalent. FIG. 8A, FIG. 8B and FIG. 8C Keratin 10 (KRT10), keratin 1 (KRT1), desmocollin 1 (DCL1), markers of suprabasal layers, stratum spinosum (SS) and stratum granulosum (SG), have a similar expression pattern in native skin in vivo (left side of panel) and epidermal equivalents, generated in vitro (right side of the panel) as demonstrated by immunohistochemistry (KRT10; dark brown pigment on H&E-stained tissue sections pointed by arrows) and immunofluorescence (red cytoplasmic/KRT1/and red cell membrane/DCL1/staining indicated by arrows). d, dermis; H&E, hematoxylin & eosin; SB, stratum basale; SC, stratum corneum; SG, stratum granulosum; SS, stratum spinosum; *, Transwell filter membrane. In FIG. 8D Desmosomes (arrows) are clearly defined in both native skin in vivo and epidermal equivalents generated in vitro. SS, stratum spinosum.

FIG. 9A-9D illustrate a comparative analysis of stratum basale (SB; basal layer) of native skin and epidermal equivalent. With regard to FIG. 9A, FIG. 9B, FIG. 9C, and FIG. 9D, MKI67, a marker of proliferation, keratin 14 (KRT14), and transcription factor TP63 show typical basal layer distribution in both native skin in vivo (left side of panel) and epidermal equivalents generated in vitro (right side of the panel), as demonstrated by immunohistochemistry (MKI67; dark brown pigment on H&E-stained tissue sections pointed by arrows) and immunofluorescence (green cytoplasmic/KRT14/and white nuclear/TP63/staining indicated by arrows). Hemidesmosomes (arrows) are clearly defined in both native skin in vivo and epidermal equivalents generated in vitro. BM, basement membrane; Cy, cytoplasm; d, dermis; H&E, hematoxylin & eosin; SB, stratum basale; SS, stratum spinosum; TM, Transwell filter membrane.

Figures 10A, 10B, 10C, 10D, 10E, 10F:
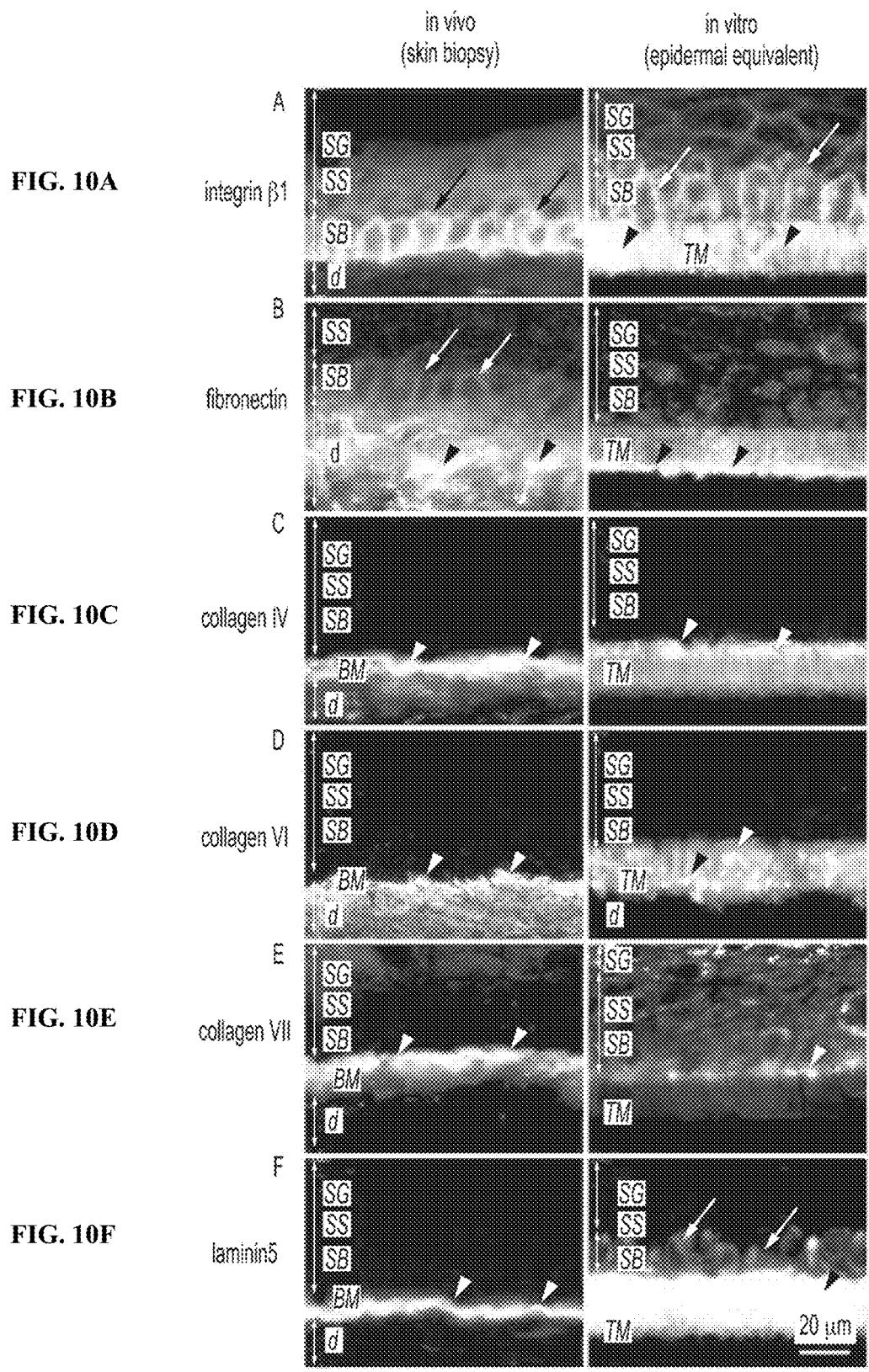
FIGS. 10A-10F illustrate a comparative analysis of extracellular matrix components of basement membrane.

FIG. 10A-10F illustrate comparative analysis of extracellular matrix components of basement membrane. Basement membrane (BM) can be formed from condensed networks of extracellular matrix (ECM) proteins, which can provide an essential structural scaffold on dermal-epidermal junction. Integrin β 1 regulates multiple epithelial cell functions by connecting cells with the ECM and it can be crucial for maintenance of BM at dermal-epidermal junction. In FIG. 10A, integrin β1 show typical basal layer distribution in both native skin in vivo (left side of panel) and epidermal equivalents generated in vitro (right side of the panel) as indicated by arrows (cell membrane-associated staining) and arrowheads (on the tip of cells protruding through the holes on Transwell membrane). BM, basement membrane; d, dermis; SB, stratum basale; SS, stratum spinosum; SG, stratum granulosum; TM, Transwell membrane.

Fibronectin can play a role in cellular adhesion. FIG. 10B illustrates that in native skin in vivo (left side of panel) fibronectin can be expressed mostly in dermis and relatively little can be detected in the BM area. Similarly, in epidermal equivalents generated in vitro (right side of the panel), fibronectin can be detected on the tip of cells protruding through the holes on Transwell membrane (red arrowheads). d, dermis; SB, stratum basale; SS, stratum spinosum; SG, stratum granulosum; TM, Transwell membrane.

The mechanical support provided by the BM can be determined by the collagen IV or, in the case of epidermal equivalents, scaffold. In FIG. 10C, As indicated with arrowheads, collagen IV expression has a similar patchy pattern in native skin in vivo (left side of panel) as epidermal equivalents generated in vitro (right side of the panel). BM, basement membrane; d, dermis; SB, stratum basale; SS, stratum spinosum; SG, stratum granulosum; TM, Transwell membrane.

Collagen VI can play a role in cellular adhesion, and can be associated with fibronectin. In native skin in vivo (left side of panel), collagen VI can expressed mostly in dermis and relatively little can be detected in the BM area as in FIG. 10D. Similarly, in epidermal equivalents generated in vitro (right side of the panel), collagen VI can be detected on the tip of cells protruding through the holes in the Transwell membrane (arrowheads), FIG. 10D. BM, basement membrane; d, dermis; SB, stratum basale; SS, stratum spinosum; SG, stratum granulosum; TM, Transwell membrane.

Collagen VII can anchors basement membrane for collagen I and III fibrils in dermis. In FIG. 10E, as pointed with arrowheads, collagen VII expression has a similar patchy pattern in native skin in vivo (left side of panel) as epidermal equivalents generated in vitro (right side of the panel). BM, basement membrane; d, dermis; SB, stratum basale; SS, stratum spinosum; SG, stratum granulosum; TM, Transwell membrane.

Laminin 5 (chain composition α3β3γ2) can be a major component of anchoring filaments and can be essential for the initial assembly of the BM in vivo. In FIG. 10F as indicated with arrowheads, Laminin 5 expression has a similar pattern in native skin in vivo (left side of panel) as epidermal equivalents generated in vitro (right side of the panel). In addition to its extra abundance in epidermal equivalents, traces of laminin 5 can be seen on cell membrane of basal layer cells (arrows). BM, basement membrane; d, dermis; SB, stratum basale; SS, stratum spinosum; SG, stratum granulosum; TM, Transwell membrane.

Figures 11A, 11B, 11C:
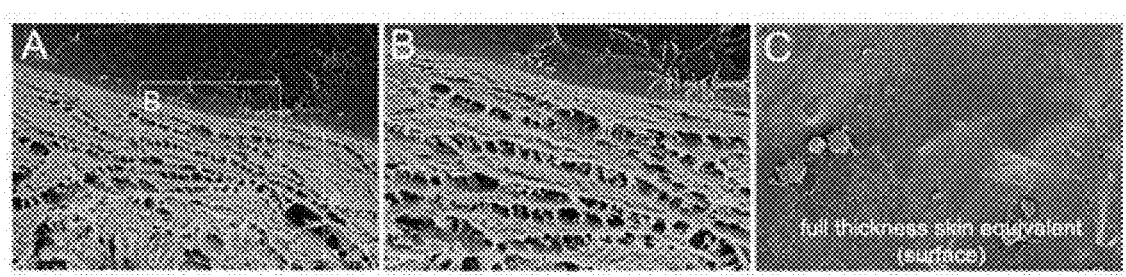
FIGS. 11A-11I illustrate a structural analysis of full-thickness skin equivalent (FSE).
Figures 11D, 11E, 11F:
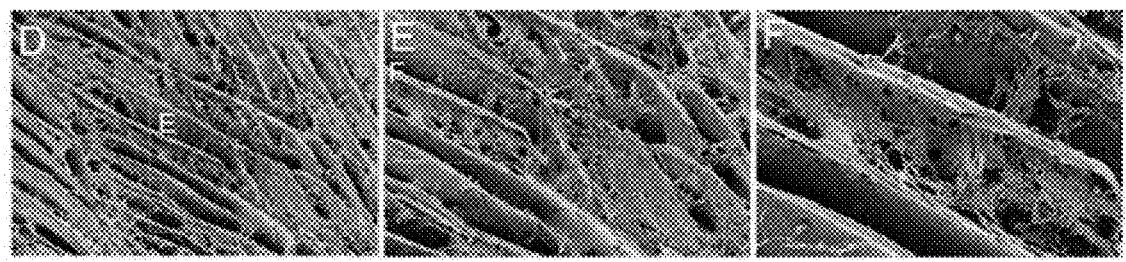
Figures 11G, 11H, 11I:

FIGS. 11A-11I illustrate a structural analysis of full-thickness skin equivalent (FSE). FIGS. 11A and 11B depict cross sections of FSE displays distinct cellular layers of epidermis under 2600× magnification (FIG. 11A) and 5200× magnification (FIG. 11B). FIG. 11C depicts a surface of an FSE at 900× magnification having a similar smooth appearance as fine leather, indicating that an FSE can induce a comparable tactile (touch) experience. FIGS. 11D-1F depict longitudinal sections of dermal scaffold with residing dermal fibroblasts and rich extracellular matrix at 91× magnification (FIG. 11D), 162× magnification (FIG. 11E) and 405× magnification (FIG. 11F). FIGS. 11G-11I depict dermal scaffolds with residing dermal fibroblasts and rich extracellular matrix at 80× magnification (FIG. 11G), 695× magnification (FIG. 11H) and 2700× magnification (FIG. 11I).

Figure 12A:
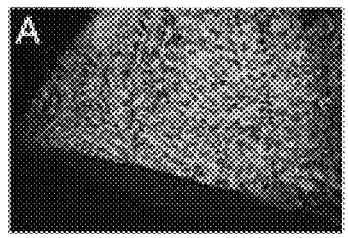
FIGS. 12A-12R illustrate a time-course of engineering dermal equivalent.
Figure 12B:
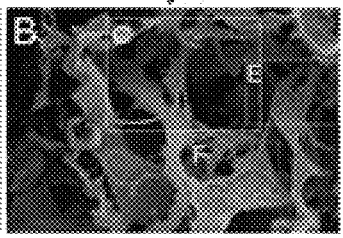
Figure 12C:
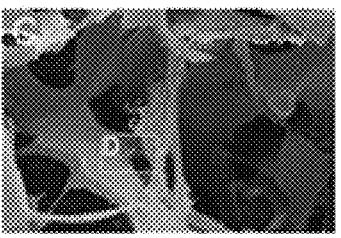
Figure 12D:
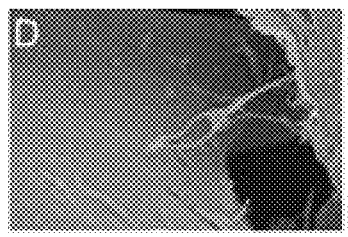
Figure 12E:
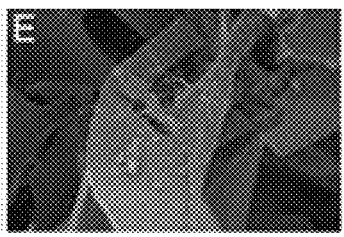
Figure 12F:
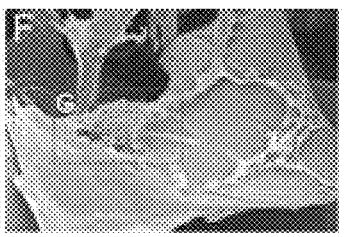
Figure 12G:
Figure 12H:
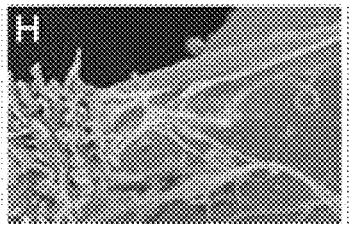
Figure 12I:
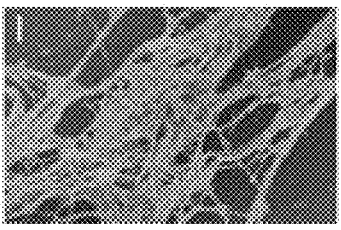
Figure 12J:
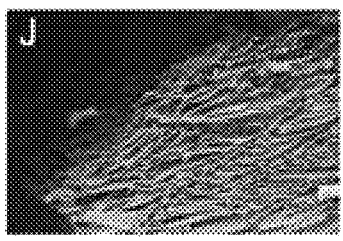
Figure 12K:
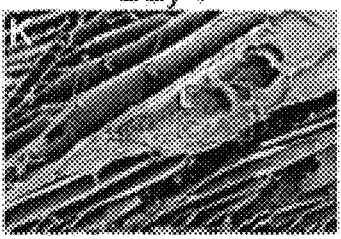
Figure 12L:
Figure 12M:
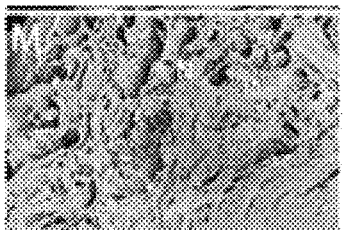
Figure 12N:
Figure 12O:
Figure 12P:
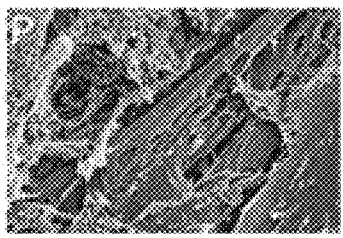
Figure 12Q:
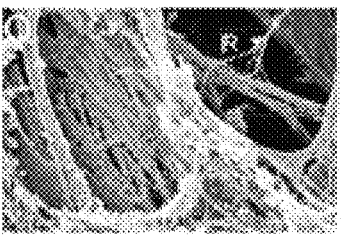
Figure 12R:
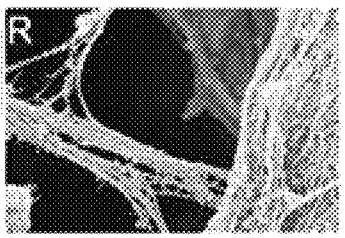

FIGS. 12A-12R illustrate a time-course of engineering dermal equivalent. FIGS. 12A-12 I depict day 2 after seeding dermal fibroblasts onto scaffold at 36× magnification (FIG. 12A), 695× magnification (FIG. 12B), 1470× magnification (FIG. 12C), 7750× magnification (FIG. 12D), 2320× magnification (FIG. 12E), 2420× magnification (FIG. 12F), 6560× magnification (FIG. 12G), 17000× magnification (FIG. 12H) and 22000× magnification (FIG. 12I). Cells can begin migrating into hollow structures of a scaffold and secreting extracellular matrix. FIGS. 12J-12 R depict day 7 after seeding dermal fibroblasts onto scaffold at 64× magnification (FIG. 12J), 100× magnification (FIG. 12K), 364× magnification (FIG. 12L), 82× magnification (FIG. 12M), 253× magnification (FIG. 12N), 3940× magnification (FIG. 12O), 5550× magnification (FIG. 12P), 9440× magnification (FIG. 12Q) and 21680 magnification (FIG. 12R). Longitudinal (FIGS. 12J-12L) and transversal sections (FIGS. 12M-

12R) can show denser cells and richer extracellular matrix, with some areas having almost complete obstruction of the hollow structure of the scaffold (FIGS. 12M-12P).

EXAMPLES

Example 1. Differentiation of iPSCs to Keratinocytes

To induce differentiation, undifferentiated iPSCs are transferred into a 20% O2 atmosphere environment and treated with mTESR1 or other pluripotent stem cell basal media supplemented with 1 mM ATRA (Sigma-Aldrich) and 25 ng/ml BMP4 (R&D) for 7 days (Induction).

To select for cells with early acquisition of ectodermal fate, the cells are harvested and replated onto freshly prepared 3D HDF ECM or other type of ECM at a density of 5-10×10³ cells per cm² and grown in Dulbecco's modified Eagle's medium/Ham F12 (3:1; Life Technologies) or Keratinocyte media supplemented with serum substitute such as human platelets lyste and with 1 mM ATRA and 25 ng/ml BMP4 for a further 7 days (Selection).

To enrich for putative epidermal progenitors, rapid adhesion to type IV collagen-coated dishes can be used, and the rapidly adhering cells are cultured in defined keratinocyte-SFM or other keratinocyte medium supplemented with 1 mM ATRA for 7 days (Enrichment). After that, the cells are cultured in EpiLife medium (Life Technologies) or other keratinocyte medium for a further 7 days (Expansion) before final harvest and analysis.

Example 2. Differentiation of Induced Pluripotent Stem Cells into a Keratinocyte Lineage Coating Tissue Culture Dishes with Geltrex and Col The procedure may be performed in a biological safety cabinet using aseptic techniques. Similar to Matrigel, Geltrex matrix solidifies rapidly at room temperature (RT). Aliquot each new batch of the matrix upon arrival and use pre-chilled pipet tips, racks and tubes while working with the reagent. 50, 100 and 200 aliquots are made and stored at −80° C. Use Geltrex at 1:100 dilutions.

The coating procedure below can be described for a 60 mm tissue culture dish. If a larger dish is to be used, adjust the volume of the coating solution accordingly. 1. Remove a 50 µL aliquot of Geltrex from the −80° C. freezer, and place it on ice in the biological safety cabinet. 2. Add 5 mL of cold sterile DMEM/F12 to a 15 mL conical tube. 3. Use a 1 mL glass pipet, take 1 mL cold DMEM/F12 from the 15 mL conical tube prepared in step 2, and add to the frozen Geltrex. Gently pipet up and down to thaw and dissolve Geltrex. Transfer the dissolved Geltrex to the rest of DMEM/F12 in the 15 mL conical tube prepared in step 2. Pipet to mix diluted Geltrex. 4. Add 50 µL of 3 mg/mL ColI stock solution into diluted Geltrex from step 3. Pipet to mix diluted Geletrex with ColI. Add 4 mL of coating solution into 60 mm dish. Tap or swirl the plate to ensure that the entire surface is coated. 5. Incubate the dish with Geltrex/ColI coating solution at 37° C. in the tissue culture incubator for at least 1 h. 6. Once the coating is complete, leave the coating solution in the dish and proceed with the plating of iPSCs as described in the next subsection. Alternatively, aspirate the coating solution and add 2 mL of fresh DMEM/F12 into the coated dish to prevent it from drying before plating the cells.

Plating iPSCs for Differentiation

Prepare one 60 mm tissue culture dish of feeder-free iPSCs grown to ~70% of confluency. Examine cells under a microscope to confirm the absence of contamination and the maintenance of their undifferentiated phenotype. If the cells are stressed or dying, they start to differentiate, presenting themselves as "cobblestone" areas with larger polymorphic cells, and should not be used for the differentiation toward keratinocytes.

For iPSC differentiation toward keratinocytes, a 1:8 split ratio of iPSCs. 1. Prewarm N2B27 medium and Dispase in the 37° C. water bath. 2. Using the microscope, confirm that the colonies are ready for passaging. Gently aspirate medium from the dish. Add 2 mL of 1×PBS, swirl the plate to wash the cells, and gently aspirate PBS. 3. Add 1 mL of Dispase and return the plate to the 37° C. tissue culture incubator for 3-5 min. 4. While the cells are being incubated with Dispase, gently aspirate the Geltrex/ColI coating solution (or DMEM/F12) from step 6 in the Geltrex/ColI coating procedure and add 4 mL of complete N2B27 medium into the coated dish. 5. After 3-5 min incubating with Dispase, confirm that the cells are ready to be picked by looking for rolled or folded edges around the colonies. 6. Transfer the plate to the biological safety cabinet and carefully aspirate Dispase. After the treatment with Dispase, the colonies are very loosely attached to the surface of the dish and may peel off if too much force is used. 7. Gently add 2 mL of plain DMEM/F12. Aspirate off the medium and repeat the wash 3 times. 8. Add 2 mL of complete N2B27 into the dish and gently scrape the colonies off the plate. Transfer the cells from the dish into a 15 mL conical tube and add 6 mL of complete N2B27 bring the total volume of cell suspension to 8 mL. 9. Gently mix the cell suspension to break large clumps of cells. Transfer 1 mL of the cell suspension to the coated dish prepared in step 3 of the current subsection. Discard or replate the leftover cells using the conditions established for a given laboratory. 10. Transfer the newly plated cells to the incubator and gently shake the plate back and forth and side to side to distribute the cells evenly. Incubate the cells overnight in the 37° C. tissue culture incubator.

Differentiation of iPSCs with RA and BMP4

The differentiation and subculturing of iPSC-derived keratinocytes are to be performed in a biological safety cabinet using aseptic techniques. Examine the new plate the day after passaging to confirm the successful attachment of iPSCs. If iPSCs start forming colonies, proceed with the differentiation protocol below.

1. Prewarm complete DKSFM (with antibiotics and DKSFM supplement) in the 37° C. water bath. 2. Add 5 mL of prewarmed DKSFM from the previous step to a 15 mL conical tube, add 5 µL of 1 mM RA to achieve 1 µM final working concentration and 5 µL of 25 µg/mL BMP4 to achieve 25 ng/mL final working concentration, mix well. 3. Aspirate off N2B27 medium from the dish with plated iPSCs, wash once with 4 mL of 1× PBS, and add 4 mL of DKSFM containing 1 µM RA and 25 ng/mL BMP4 from the step above. This is day 1 of differentiation procedure. 4. Transfer the cells to the incubator and incubate for 48 h. 5. Replace the medium with fresh DKSFM containing 1 µM RA and 25 ng/mL BMP4 after 48 h of incubation. Transfer the cell to the incubator for another 48 h. 6. After the second round of 48 h induction (day 4 of differentiation), replace the medium with complete DKSFM without RA and BMP4. Incubate cells in the incubator for 10 days in complete DKSFM, changing medium every other day. 7. On day 14 of differentiation, prepare complete CnT-07 medium by adding antibiotics and provided supplements, pre-warm the medium. By this day, the majority of the cells in the outgrown iPSC colony start exhibiting an epithelial-like phenotype. 8. Aspirate off DKSFM from differentiated cells, and replace with 4 mL of complete CnT-07. Incubate the cells in the tissue culture incubator for another 10 days, changing complete CnT-07 every other day.

Rapid Attachment and Culturing of iPSC-Derived Keratinocytes

On day 24 of differentiation, many cells that migrate away from the outgrown iPSC colony exhibit a keratinocyte-like phenotype, and start expressing p63, a master regulator required for the commitment of the ectoderm to a keratinocyte fate, and Krt14. By this day, the 60 mm dish used for iPSC differentiation is fully confluent and need to be passaged. To enrich for iPSC-derive keratinocytes during passaging, the of the differentiated iPSC culture is rapidly attached to ColI/ColIV coated plates. Up to four 100 mm ColI/ColIV-coated tissue culture dishes are used to perform the rapid attachment procedure from one 60 mm dish containing differentiated iPSCs. If only one 100 mm dish is to be used, plate one fourth of the differentiated iPSC culture for the rapid attachment procedure.

Coating Plates with ColI and ColIV

The procedure may be performed in the biological safety cabinet using aseptic techniques. 1. Reconstitute ColIV powder to a concentration of 2 mg/mL in sterile 0.25% Glacial acetic acid. Dissolve for several hours at 2-8° C., occasionally swirling. Make aliquots and store them at −20° C. 2. Thaw the aliquot of ColIV stock solution (2 mg/mL) very slowly by placing the vial in an ice bucket and keeping it at 4° C. for several hours. 3. Resuspend ColIV stock solution in the appropriate volume (5 mL per each 100 mm dish) of sterile 0.25% Glacial acetic acid to a final working concentration of 7 μg/mL. Add an appropriate volume of ColI stock solution to achieve a final working ColI concentration of 30 μg/mL. Coat the plates by using 5 mL of working solution to cover a 100 mm dish. Incubate the plates at room temperature in the biological safety cabinet for 1 hour. 4. Aspirate the liquid from the coated plates, rinse the dishes once with 5 mL of sterile 1× PBS and once with 5 mL of ddH2O. 5. Air-dry the washed dishes in the biological safety cabinet. Use plates directly or seal them with Parafilm and store at 4° C. for up to 6 months. To use a previously stored ColIV-coated plate, allow the plate to warm up at room temperature in the biological safety cabinet for at least 1 hour prior to plating cells.

Rapid Attachment of iPSC-Derived Keratinocytes

1. On day 24 of differentiation, prewarm complete CnT-07, Accutase, and ColI/ColIV-coated dish(es). 2. Wash the cells with 1×PBS, add 2 mL of Accutase and incubate in the tissue culture incubator for 5 min. Confirm under the microscope that cells start detaching. 3. Add 3 mL of complete Cnt-07, pipet up and down to dislodge the cells and collect the cell suspension into a 15 mL conical tube. Spin the cells down at 260×g for 5 min and aspirate the supernatant. Resuspend the pellet in 10 mL of complete Cnt-07 medium, repeat the spin at 260×g for 5 min, and aspirate the supernatant. 4. Resuspend the pellet in 4 mL of complete CnT-07, pipet up and down to break cell clumps into single cells. 5. Add 9 mL of complete CnT-07 medium into each ColI/ColIV-coated dish and transfer 1 mL of cell suspension from step 4 above into each ColI/ColIV-coated dish. Allow the cells to attach to the coated dish at room temperature for 15-30 min. 6. Carefully aspirate the medium with the floating cells (these are undifferentiated or partially differentiated iPSCs). Do not disturb the attached cells (these are iPSCderived Krt14 positive cells). Add 10 mL of fresh complete CnT-07 medium into the plate with the attached cells. Let the cells expand in the 37° C. tissue culture incubator, changing the medium every other day. Passage cells as needed with Accutase in CnT-07 or EpiLife (with EDGS supplement) on ColI-coated dishes. After passage 2 or 3 and following the rapid attachment step, the culture should consist of ~90% of Krt14 positive cells exhibiting a keratinocyte-like phenotype. The keratinocyte-like phenotype of the obtained culture can be verified by standard immunflorescence analyses for Krt14 expression and by the ability to reconstitute a normal stratified epidermis in organotypic cultures.

Example 3. Preparing Epidermal Layer from Primary Keratinocytes

Primary keratinocytes are isolated from a single neonatal foreskin and grown in 0.07 mM $Ca^{2+}$ 154CF medium (Life Technologies) supplemented with man keratinocyte growth supplement. A suspension of first-passage keratinocytes ($2.21 \times 10^5$/cm$^2$ insert) is seeded on Cellstart CTS (Life Technologies) (or other ECM substrate) coated PET, 0.4-mm inserts (EMD Millipore) in CnT-07 media (CELLnTEC) or CnT-Prime media (CELLnTEC) according to manufacturer's protocol.

Day 3 (D3) after seeding, the media are switched to CnT-02-3D (CELLnTEC) or CnT-3D Barrier (CELLnTEC). On day 4, the HEEs are air exposed by feeding the bottom of the insert with CnT-02-3D or CnT-3D Barrier. From day 4 onward, HEEs are fed daily with CnT-02-3D or CnT-3D Barrier until harvested. HEEs are grown in a humid (at 100% RH) or dry incubator (at 50% RH) at 37° C. and 5% $CO_2$. A dial hydrometer (Fisher Scientific) is used to measure incubator humidity. Low incubator humidity is maintained by removal of water pan.

To control for possible changes in osmolarity, media are refreshed daily. Significant changes in osmolarity are not detected using this protocol, as measured by a Micro Osmometer (Precision Systems). Twelve-well inserts are used for transepithelial electrical resistance (TEER) measurements, light microscopy, and electron microscopy, while six-well inserts are used for transepidermal water loss (TEWL) measurements and immunoblotting.

Example 4. Culturing an Epidermal Layer

Keratinocytes are seeded at a density of $2.0$-$2.5 \times 10^5$ cells/cm$^2$ of polyethylene terephthalate (PET) membrane with 0.4 μm pore inserts (EMD Millipore; Cat. No.: MCHT12H48) in CnT-07 media (CELLnTEC) or CnT-Prime media (CELLnTEC).

Day 3 (D3) after seeding, the media are switched to CnT-02-3D (CELLnTEC) or CnT-3D Barrier (CELLnTEC). On day 4, the cells air exposed by feeding the bottom of the insert with CnT-02-3D CnT-3D Barrier. From Day 4 onward, the epidermal layer is fed daily with CnT-02-3D or CnT-3D Barrier until harvested at Day 14.

Example 5. Preparing Support Substrate

To prepare a 2% agarose solution, 2 g of Ultrapure Low Melting Point (LMP) agarose is dissolved in 100 mL of ultrapure water/buffer solution (1:1, v/v). The buffer solution may be optionally PBS (Dulbecco's phosphate buffered saline 1×) or HBSS (Hanks' balanced salt solution 1×). The agarose solution may be placed in a beaker containing warm water (over 80° C.) and held on the hot plate until the agarose dissolves completely. The agarose solution remains liquid as long as the temperature is above 36° C. Below 36° C., a phase transition occurs, the viscosity increases, and finally the agarose forms a gel.

To prepare agarose support substrate, 10 mL of liquid 2% agarose (temperature >40° C.) may be deposited in a 10 cm diameter Petri dish and evenly spread to form a uniform layer. Agarose is allowed for form a gel at 4° C. in a refrigerator.

Example 6. Producing a Synthetic Leather Comprising Fibroblasts, Keratinocytes, and Melanocytes The outline of the protocol can be as follow: a) bringing fibroblasts and a solution of collagen into contact, then incubating for a sufficient period of time to obtain a contracted collagen matrix in which the fibroblasts are distributed, constituting a dermis equivalent, b) seeding, with a mixture of keratinocytes and melanocytes, the dermis equivalent obtained in a), and immersion culture in a liquid medium, c) immersion of the entire culture (keratinocytes and melanocytes seeded on the dermis equivalent) obtained in b), and continuation of the culture at the air-liquid interface until a pluristratified epidermis equivalent containing melanocytes, on a dermis equivalent containing fibroblasts in a collagen matrix, constituting a skin equivalent, is obtained.

Step a) can be carried out with collagen type I, in particular of bovine origin, or a mixture of collagens I and III (approximately 30% relative to the final volume of the lattice) in homogeneous suspension. Advantageously, other constituents are added thereto, such as laminin (in particular, from 1% to 15% relative to the final volume), collagen IV (in particular, from 0.3% to 4.5% relative to the final volume) and/or entactin (in particular, from 0.05% to 1% relative to the final volume) so as to obtain a homogeneous suspension. The fibroblasts are obtained from skin. They are cultured in a suitable medium, and then suspended before mixing with the suspension of collagen and growth factors. The mixture is incubated for 1 to 6 days, preferably for 4 or 5 days, at a temperature of approximately 37° C., generally from 36° C. to 37.5° C. Advantageously, the mixture is incubated on a support which does not allow adhesion thereof, in particular which prevents adhesion of the mixture to the edges of the support; such a support may in particular be obtained by prior treatment of its surface, for example by coating said surface with bovine albumin or serum. A collagen gel which is contracted freely in several directions, while discharging the nutritive medium, and in which the fibroblasts are embedded, is thus obtained.

In order to carry out step b), use can be made of keratinocytes originating from skin, preferably from adult skin. The keratinocytes are amplified before seeding according to the technique of Rheinwald and Green (Cell, vol. 6, 331-344, 1975) by culture on a feeder support constituted of 3T3 fibroblasts in a suitable medium known to those skilled in the art, in the presence of growth factors, in particular of amino acids, serum, cholera toxin, insulin, triiodothyronine and pH buffer solution. In particular, such a culture medium may especially contain at least one mitogenic growth factor for keratinocytes (for example, epidermal growth factor (EGF) and/or keratinocyte growth factor (KGF), in particular KGF), insulin, hydrocortisone and, optionally, an antibiotic (for example: gentamycin, amphotericin B).

The melanocytes can be melanocytes originating from young or adult animal skin. They are amplified by culture in a suitable medium, in the absence of phorbol ester, composed of a base medium such as DMEM/F12 or MCDB153 and supplemented with melanocyte-specific growth factors (such as, for example, bFGF, SCF, ET-1, ET3 or aMSH), and in particular in M2 medium (Promocell) or in other media such as M254 (Cascades Biologics™).

Cell suspensions of melanocytes and of keratinocytes are prepared from these cultures, and mixed so as to obtain mixed keratinocyte/melanocyte suspensions. The melanocyte/keratinocyte ratio may be from 1:10 to 2:1, and is generally approximately 1:1. This mixed suspension is deposited on the dermis equivalent. The dermis equivalent is advantageously attached to a support via a biological material such as collagen. The melanocyte/keratinocyte suspension is deposited in a ring or any equivalent means for maintaining it on a delimited surface part. A liquid nutritive medium is added in such a way as to cover the mixture of cells. This medium contains growth factors known to those skilled in the art, in particular EGF and/or KGF. The medium will be replaced regularly and the culture continued as an immersion, generally for a period of from 2 to 10 days, in particular from 5 to 8 days, and approximately 7 days. The medium contains KGF starting from the 2nd day of immersion, and ideally starting from the 4th day of immersion.

The skins are subsequently, in a manner known per se, immersed so as to obtain differentiation of the keratinocytes and formation of a stratified epidermis equivalent. This step c) corresponding to the culture as an immersion at the air-liquid interface is continued until a differentiated structure is obtained, in general approximately 7 days. However, step c) may be continued for a longer period of time, for example for approximately 28 days, while at the same time conserving a skin equivalent having the advantageous characteristics specified in the above text. The nutritive culture medium will be refreshed regularly. The skin equivalent is subsequently removed so as to perform required tests.

Example 7. Induction of Follicle Formation in Cultured Skin Specimens

Expanded DP cells are mixed with cultured ORS cells, washed, and carefully resuspended in 20 ml of sterile phosphate buffered saline (PBS, Sigma) at suitable cell densities. Cultured DP and ORS cells used in each experiment are obtained from different donors, because the different duration of culture for DP and ORS cells do not allow preparation of the two cell types from the same donor. The cell suspension is slowly injected into the dermis of cultured skin pieces 1 day after establishing the culture.

Example 8. Culturing Hair Follicle Cell Populations

Hair follicles are obtained from the occipital region. Dermal papilla (DP) cells are prepared and cultured as described in Randall et al., A comparison of the culture and growth of dermal papilla cells from hair follicles from non-balding and balding (androgenetic alopecia) scalp. Br J Dermatol 1996: 134: 437-444).

Briefly the DP of the hair follicles is isolated under a dissecting microscope and transferred individually to a 24-well tissue culture plate (Sarstedt). Cell culture is performed in DMEM, supplemented with 15% FCS (Sigma). After initiation of cell proliferation, cells are cultured to confluency and expanded for two passages. For isolation of outer root sheath (ORS) cells, the middle part of the hair follicles, containing the bulge region, is excised and subjected to mild trypsinization. At least cells of 10 hair follicles are used for each culture. The obtained cells are washed twice in RPMI-1640 medium (Sigma) and subjected to cell culture in standard keratinocyte medium (Epilife, Sigma). Cells are harvested after 1 week of culture.

Example 9. Tanning Full Thickness Skin Equivalents

Full thickness skin equivalents are tanned by chrome tanning. The first step is ice and sulfuric acid treatment. This opens up the tissue so it can receive the chromium. The chromium is then added along with magnesium oxide.

The process brings the pH level of the full thickness skin equivalents down to around 3. After chromium has worked through the full thickness skin equivalents the tanning liquor is then introduced which brings the pH level up to around 4. This is followed by a warm water bath and then roll pressing to remove excessive liquid. The final stage is then to apply a surface treatment if necessary and then dry the full thickness skin equivalents while stretched out and then re-press when done.

Example 10. X-Tan Tanning Protocol

Full thinkness skin equivalents can be tanned using an X-tan procedure. Prior to tanning, a full thinkness skin equivalent was limed, which comprises the steps of soaking the skin equivalent, adding a substrate, adjusting the pH, and washing. The skin equivalent was then be de-limed by washing the skin equivalent, adding a pre-deliming buffer, deliming the skin equivalent, and washing. The skin equivalent was then tanned by wetting back, adding a tanning substrate, adjusting the pH to a pH conducive for the tanning, performing cycles of fixation and fixation, and fat liquoring to obtain the tanned skin equivalent.

Example 11. Full Thickness Skin Equivalents

A type I collagen matrix (containing $0.5 \times 10^6$ iPSC derived fibroblasts) can be deposited onto polyethylene terephthalate membranes (BD Biosciences), and allowed to polymerize. After incubation of the polymerized matrix for about 7 days, $1 \times 10^6$ iPSC-derived keratinocytes and $0.1 \times 10^6$ iPSC-derived melanocytes can be seeded onto the matrix, and incubated for a further 7 days. The composite culture can be raised to the air-liquid interface and fed from below to induce epidermal differentiation. Full thickness skin equivalents can harvested about 14 days later and either snap frozen in LN2 or embedded in wax. For melanin quantification

Example 12. Immunostaining of Frozen Section

Fixation: Tissues can be fixed in 3.8% paraformaldehyde/phosphate-buffered saline (PBS), pH 7.2-7.6 for 30 minutes. The samples can be washed three times 5 minutes in PBS. The tissue samples can be infiltrated with a series of sterile sucrose gradients (10% sucrose overnight, 15% sucrose for 6-8 hours, 30% sucrose overnight and finally in 30% sucrose mixed 1:1 with optimal cutting temperature (OCT) compound overnight) rotating on 4° C. The samples can be embedded in OCT and frozen in liquid nitrogen vapor. The cryo-blocks can be stored at −80° C.

Cutting sections: The day before cutting, the cryo-blocks can be transferred to −20° C. overnight. Sections (10 μm) can be prepared using a standard cryostat. The sections can be kept at −20° C. untill processing.

Processing: Control incubations can be included. Preimmune sera or isotype-matched nonimmune antibodies can be used instead of the primary antibodies. The sections can be submerged in either 90% cold acetone for 10 minutes or 0.2% triton X-100/PBS for 5 minutes to expose antigens. The samples can be washed three times 5 minutes in PBS. Nonspecific antibody reactivity was blocked by submerging the sections into 5% BSA with 0.1% triton X-100 for 1 hr. The sections can be then incubated overnight at 4° C. with a mixture of the two antibodies: i) 2.5 μg/ml of ChromPure donkey whole IgG (for purpose of blocking; all secondary antibodies can be made in donkey); ii) 1 μg/ml of appropriate primary antibody. The sections can be rinsed three times 5 minutes in PBS. The sections can be incubated for 30 to 60 min at room temperature with the appropriate species-specific secondary antibody, made in donkey, and conjugated to either red or green fluorophore. The sections can be washed three times 5 minutes in PBS. The sections can be then incubated for 10 minutes with 10 μg/ml Hoechst 33342 at room temperature. The sections can be washed 3 times 5 minutes with PBS.

Visualization: The samples can be mounted with Vectashield medium (Vector) and the samples can be visualized with epifluorescence microscope (Zeiss), equipped with appropriate filters.

Example 13. Immunostaining of Paraffin Embedded Sections

Fixation: Tissues can be fixed in 3.8% paraformaldehyde/phosphate-buffered saline (PBS), pH 7.2-7.6 for 30 minutes. The samples can be washed three times 5 minutes in PBS. The tissue samples can be dehydrated in ascending ethanol series (50%, 70%, 2×100%; 20 min each) and clearing agent (xylene, 2×20 min). The samples can be perfused with paraffin wax at 65° C. 2× 1 hour and embedded in paraffin blocks. The paraffin blocks can be stored at room temperature until further use.

Cutting sections: The tissue was sectioned at 5 μm thickness using a standard microtome. The sections can be kept at room temperature untill processing.

Processing: Control incubations can be included. Preimmune sera or isotype-matched nonimmune antibodies can be used instead of the primary antibodies. The sections can be re-hydrated in ascending series xylene/ethanol series 2× xylene, 2× 100% ethanol, and 1× 70% and 50%; 10 min each. The sections can be then briefly rinsed with tap water. The sections can be then stained with hematoxylin for 5 minutes. The sections can be then washed with dH$_2$O until solution was clear. The sections can be stained with 0.5% Eosin for 10 minutes. The sections can be then rinsed briefly in tap water. Nonspecific antibody reactivity was blocked by submerging the sections into 5% BSA for 1 hr. The sections can be then incubated for overnight at 4° C. with a mixture of the two antibodies: i) 2.5 μg/ml of ChromPure donkey whole IgG (for purpose of blocking; all secondary antibodies are made in donkey); ii) 1 μg/ml of appropriate primary antibody. The sections can be rinsed three times 5 minutes in PBS. The sections can be incubated for 30 min at room temperature with the appropriate species-specific secondary antibody, made in donkey, and conjugated to horseradish peroxidase (HRP). The sections can be washed three times 5 minutes in PBS.

Visualization: The samples can be incubated with 3,3'-diaminobenzidine (DAB) substrate kit (VectorLaboratories) according to manufacturer's protocol. DAB yield a brown stain. If nickel chloride is added to the substrate solution, a gray-black stain can result. The samples can be dehydrated in ascending ethanol series (50%, 70%, 2×100%; 10 min each) and clearing agent (xylene, 2×10 min). The samples can be mounted in mounting medium and visualized with phase contrast microscope (Zeiss) equipped with digital camera.

Example 14. Field Emission Scanning Electron Microscopy (FESEM)

Fixation: Samples can be fixed for 24 hours at 4° C. with 4% paraformaldehyde and 2% glutaraldehyde in 0.1M Sodium Cacodylate Buffer (pH7.4) and placed in 0.1 M sodium cacodylate buffer and maintained at 4° C. prior to further processing.

Processing: The samples can be post-fixed for 1 hour with 1% aqueous OsO4. After dehydration in an ascending ethanol series (50%, 70%, 2×100%; 10 min each) samples can be critical point dried with liquid $CO_2$ in a Tousimis Autosamdri-815B apparatus, mounted with double-sided copper tape onto 15 mm aluminum mounts, and sputter-coated with 40 Å of gold-palladium using a Denton DeskII Sputter Coater.

Visualization: Cross sections of duplicate samples can be mounted onto low profile 45/90 degree SEM mounts for analysis of internal morphology. Visualization can be performed with a Zeiss Sigma FESEM (Carl Zeiss Microscopy, Thornwood, N.Y.) operated at 2-3 kV, using inLens Secondary Electron (SE) detection, as well as mixed signal InLens/SE2 (75/25%) detection at working distance 3-5 mm. Images can be captured in TIFF using store resolution 2048×1536 and a line averaging noise reduction algorithm.

Processing: Previously dried samples (i.e. leather) can be cut to size and sputter-coated with 40 Å of gold-palladium using a Denton DeskII Sputter Coater.

Visualization: Cross sections of duplicate samples can be mounted onto low profile 45/90 degree SEM mounts for analysis of internal morphology. Visualization was performed with a Zeiss Sigma FESEM (Carl Zeiss Microscopy, Thornwood, N.Y.) operated at 2-3 kV, using inLens Secondary Electron (SE) detection, as well as mixed signal InLens/SE2 (75/25%) detection at working distance 3-5 mm. Images can be captured in TIFF using store resolution 2048×1536 and a line averaging noise reduction algorithm.

Example 15. Transmission Electron Microscopy (TEM)

Fixation: Samples can be fixed 30 minutes at 4° C. in 2% glutaraldehyde and 2% paraformaldehyde with 0.06% calcium chloride in 0.1 M sodium cacodylate buffer, pH 7.4. The samples can be then placed in 0.1 M sodium cacodylate buffer and maintained at 4° C. prior to further processing.

Processing: The samples can be then washed and placed in either 0.2% ruthenium tetroxide (for visualization of lipid bilayers) or 1.5% osmium tetroxide with 1.5% potassium ferrocyanide, in 0.1 M sodium cacodylate, pH 7.4, at room temperature in the dark for 45 minutes. After rinsing in buffer, the samples can be dehydrated in a graded ethanol series (50%, 70%, 2×100%; 10 min each), and subsequently embedded in a low-viscosity Epoxy resin.

Visualization: Semi-thin sections can be stained with 1% toluidine blue with 1% azure II in 1% borax solutions and viewed under phase contrast microscope (Zeiss). Ultrathin sections can be collected and stained with water-saturated 3% uranyl acetate and/or contrasted in 2.5% lead citrate on uncoated nickel grids. Ultrathin sections can be viewed with a Zeiss 10 A electron microscope operated at 60 kV. Images can be captured in TIFF.

Ion capture cytochemistry ($Ca^{++}$ gradient):

Fixation: For ultrastructural $Ca^{++}$ localization, the samples can be fixed in 2% paraformaldehyde, 2% glutaraldehyde, 0.09 M potassium oxalate, containing 0.04 M sucrose. Samples can be subsequently fixed overnight at 4° C., Processing: The samples can be post-fixed in 1% osmium tetroxide containing 2% potassium pyroantimonate, pH 7.4 for 2 hrs at 4° C. in the dark. Tissue samples then can be washed in alkalinized water (pH 10) and transferred to ethanol solutions (50%, 70%, 2×100%; 10 min each) for dehydration and embedding in a low-viscosity, Epoxy resin.

Visualization: Ultrathin sections can be collected and stained with water-saturated 3% uranyl acetate and/or contrasted in 2.5% lead citrate on uncoated nickel grids. Ultrathin sections can be viewed with a Zeiss 10 A electron microscope operated at 60 kV. Images can be captured in TIFF.

Lanthanum Perfusion:

Fixation: The perfusion pathway was assessed in all subjects by immersion of samples in 4% lanthanum nitrate in 0.05 M Tris buffer containing 2% glutaraldehyde, 1% paraformaldehyde, pH 7.4, for 1 hour at room temperature.

Processing: The samples can be washed and placed in 1.5% osmium tetroxide with 1.5% potassium ferrocyanide, in 0.1 M sodium cacodylate, pH 7.4, at room temperature in the dark for 45 minutes. After rinsing in cacodylate buffer, the samples can be dehydrated in a graded ethanol series (50%, 70%, 2×100%; 10 minutes each), and subsequently embedded in a low-viscosity, Epoxy resin.

Visualization: Ultrathin sections can be collected and stained with water-saturated 3% uranyl acetate and/or contrasted in 2.5% lead citrate on uncoated nickel grids. Ultrathin sections can be viewed with a Zeiss 10 A electron microscope operated at 60 kV. Images can be captured in TIFF.

While some embodiments have been shown and described herein, such embodiments are provided by way of example only. Numerous variations, changes, and substitutions will now occur to those skilled in the art without departing from the disclosure provided herein. It should be understood that various alternatives to the embodiments described herein can be employed.

What is claimed is:

1. A method of forming a tanned leather, wherein said method comprises:
   a) forming a cell layer comprising an immortalized cell in contact with a scaffold,
      i) wherein said scaffold comprises a polycaprolactone, a polyethylene, a polypropylene, a polyvinyl alcohol, a zein, an alginate, a starch, a cellulose, a cotton, an acetate, an acrylic, a fiber, a linen, a nylon, a rayon, a velvet, a modacrylic, an olefin polyester, a saran, a vinyon, a wool, a jute, a hemp, a bamboo, a flax, or any combination thereof, and
      ii) wherein said cell layer comprises a collagen; and
   b) tanning at least a portion of said collagen to generate said tanned leather.

2. The method of claim 1, wherein said scaffold comprises a fiber.

3. The method of claim 2, wherein said fiber comprises a latex, a vegetable, a polyamide, a modified cellulose, or any combination thereof.

4. The method of claim 1, wherein said scaffold comprises said cellulose, wherein said cellulose comprises a rayon, a viscose, an acetate, a rayon acetate, or any combination thereof.

5. The method of claim 1, further comprising forming said tanned leather into one or more of a watch strap, a belt, a packaging, a shoe, a boot, a footwear, a glove, a clothing, a luggage, a bag, a clutch, a purse, a backpack, a wallet, a saddle, a harness, a whip, or any combination thereof.

6. The method of claim 1, wherein said scaffold comprises said bamboo.

7. The method of claim 1, wherein said scaffold comprises said polyethylene, wherein said polyethylene comprises a polyethylene terephthalate.

8. The method of claim 1, wherein the method further comprises removing at least a portion of said immortalized cell from said cell layer prior to said tanning.

9. The method of claim 1, wherein the method further comprises performing further processing on said cell layer.

10. The method of claim 9, wherein said further processing comprises a member selected from the group consisting of: a preserving, a soaking, a bating, a pickling, a depickling, a thinning, a retanning, a lubricating, a crusting, a wetting, a sammying, a shaving, a rechroming, a neutralizing, a dyeing, a fatliquoring, a filling, a stripping, a stuffing, a whitening, a fixating, a setting, a drying, a conditioning, a milling, a staking, a buffing, a finishing, an oiling, a brushing, a padding, an impregnating, a spraying, a roller coating, a curtain coating, a polishing, a plating, an embossing, an ironing, a glazing, a tumbling, and any combination thereof.

11. The method of claim 1, wherein said tanning comprises a vegetable tanning, a chrome tanning, an aldehyde tanning, a syntan tanning, a bacterial dyeing, or any combination thereof.

12. The method of claim 1, wherein said collagen comprises a type I collagen, a type III collagen, or a combination thereof.

13. The method of claim 1, wherein a thickness of said cell layer ranges from about 0.02 mm to about 5 mm.

14. The method of claim 1, wherein said tanned leather further comprises a member selected from the group consisting of a keratin, an elastin, a gelatin, a proteoglycan, a dermatan sulfate proteoglycan, a glycosoaminoglycan, a fibronectin, a laminin, a dermatopontin, a lipid, a fatty acid, a carbohydrate, or any combination thereof.

15. The method of claim 1, wherein said cell layer is cultured in vitro.

16. The method of claim 1, wherein said scaffold further comprises a polylactic acid (PLA).

17. A composition comprising a cell layer comprising an isolated immortalized cell in contact with a scaffold
   a) wherein said scaffold comprises a polycaprolactone, a polyethylene, a polypropylene, a polyvinyl alcohol, a zein, an alginate, a starch, a cellulose, a cotton, an acetate, an acrylic, a fiber, a linen, a nylon, a rayon, a velvet, a modacrylic, an olefin polyester, a saran, a vinyon, a wool, a jute, a hemp, a bamboo, a flax, or any combination thereof, and
   b) wherein said cell layer comprises a collagen.

18. The composition of claim 17, wherein said collagen comprises a type I collagen, a type III collagen, or a combination thereof.

19. The composition of claim 17, wherein said composition further comprises an extracellular matrix.

20. The composition of claim 17, wherein said scaffold further comprises a polylactic acid (PLA).

* * * * *